(12) United States Patent
Afriat Herskovits et al.

(10) Patent No.: US 9,976,149 B2
(45) Date of Patent: May 22, 2018

(54) MODIFIED LISTERIA BACTERIA AND USES THEREOF

(71) Applicant: Ramot at Tel-Aviv University Ltd., Tel-Aviv (IL)

(72) Inventors: Anat Afriat Herskovits, Kfar-Saba (IL); Millie Kaplan Zeevi, Hod-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 46 days.

(21) Appl. No.: 14/706,178

(22) Filed: May 7, 2015

(65) Prior Publication Data
US 2015/0368654 A1    Dec. 24, 2015

Related U.S. Application Data

(60) Provisional application No. 61/990,220, filed on May 8, 2014.

(51) Int. Cl.
*A61K 39/02* (2006.01)
*A61K 39/00* (2006.01)
*C12N 15/74* (2006.01)

(52) U.S. Cl.
CPC .......... *C12N 15/74* (2013.01); *A61K 39/0208* (2013.01); *A61K 2039/52* (2013.01); *A61K 2039/522* (2013.01)

(58) Field of Classification Search
CPC .......... A61K 2039/52; A61K 2039/522; A61K 39/0208; A61K 2039/58; A61K 2039/585; A61K 39/00; A61K 39/02; C12N 15/74
See application file for complete search history.

(56) References Cited

U.S. PATENT DOCUMENTS

| 2010/0285067 A1* | 11/2010 | Portnoy | A61K 39/02 424/234.1 |
| 2011/0027319 A1 | 2/2011 | Portnoy et al. | |
| 2012/0164107 A1* | 6/2012 | Portnoy | A61K 35/74 424/93.2 |

FOREIGN PATENT DOCUMENTS

WO    WO 2008/066774    6/2008

OTHER PUBLICATIONS

Crimmins et al. PNAS 105: 10191-10196, 2008).*
Yamamoto et al. Infect. Immun. 80: 2323-2332, 2012.*
Schwartz et al. Infect. Immun. 80: 1537-1545, 2012.*
Crimmins et al. PNAS 105: 10191-10196, 2008.*
Ratani SS. Heavy Metal and Epidemic Clonal Characteristics among Listeria monocytogenes from a "Historical" Collection and Other Sources, Thesis submitted for Master of Science, pp. 1-87, 2012.*
Archer et al. "STING-Dependent. Type I IFN Production Inhibits Cell-Mediated Immunity to Listeria Monocytogenes", PLOS Pathogenes, 10(1): e1003861-1-e1003861-14, Jan. 2, 2014.
Kaplan Zeevi et al, "Listeria Monocytogenes Multidrug Resistance Transporters and Cyclic Di-AMP, Which Contribute to Type I Interferon Induction, Play a Role in Cell Wall Stress", Journal of Bacteriology, 195(23): 5250-5261, Dec. 2013.
Woodward et al. "C-Di-AMP Secreted by Intracellular Listeria Monocytogenes Activates a Host Type I Interferon Response", Supporting Online Material, Science Express, p. 1-15, May 27, 2010.

* cited by examiner

*Primary Examiner* — S. Devi

(57) ABSTRACT

A *Listeria* bacterium is disclosed which comprises a first mutation in the multidrug resistance transporter M (MdrM) gene which causes a decrease in interferon-β production in macrophages as compared to wild-type *Listeria* bacterium and a second mutation in the multidrug resistance transporter T (MdrT) gene which causes a decrease in interferon-β production in macrophages as compared to the wild-type *Listeria* bacterium.

18 Claims, 18 Drawing Sheets
(1 of 18 Drawing Sheet(s) Filed in Color)

FIGs. 1A-D

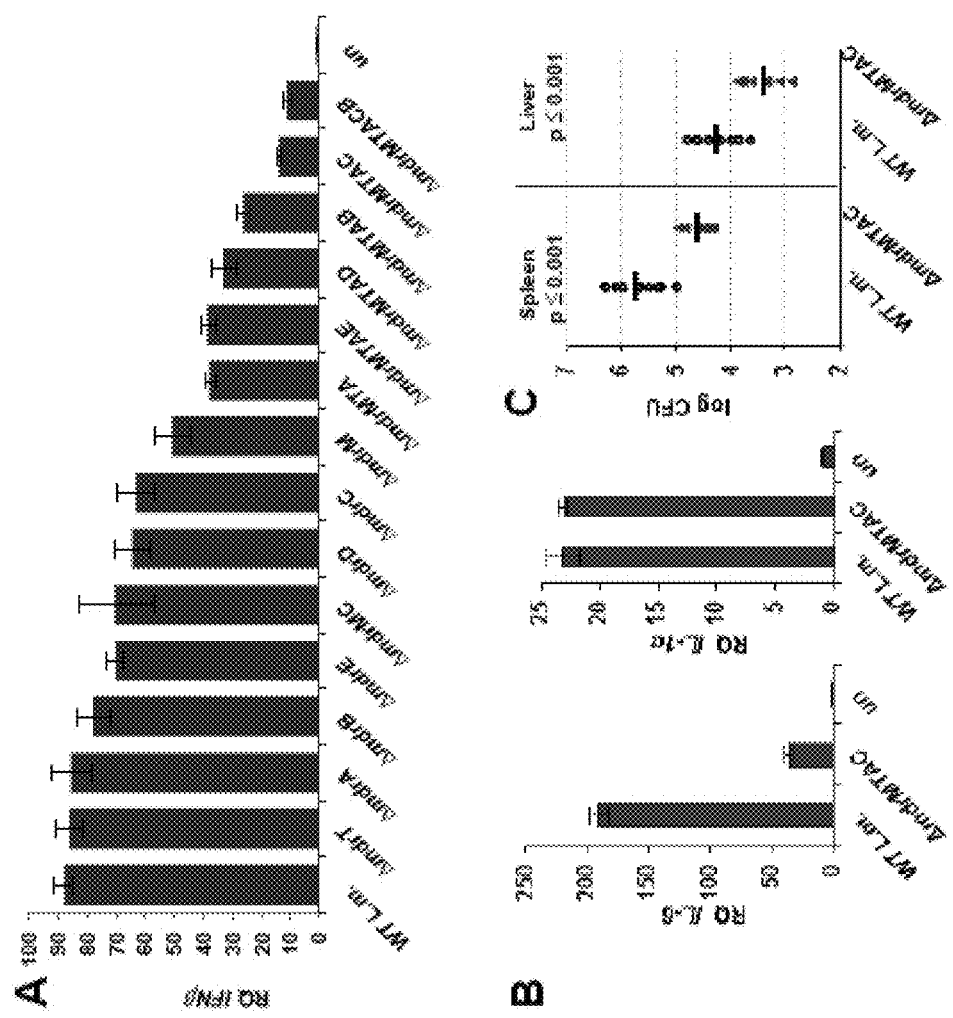
FIGs. 3A-C

FIGs. 4A-C
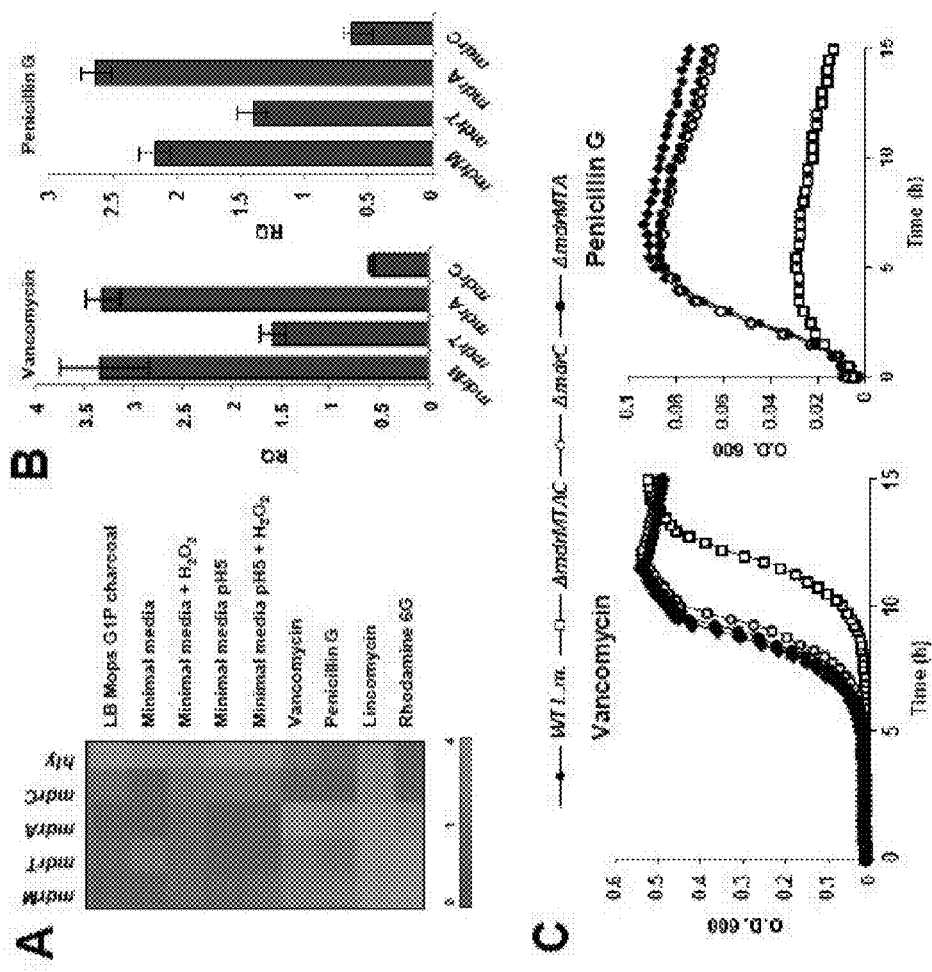

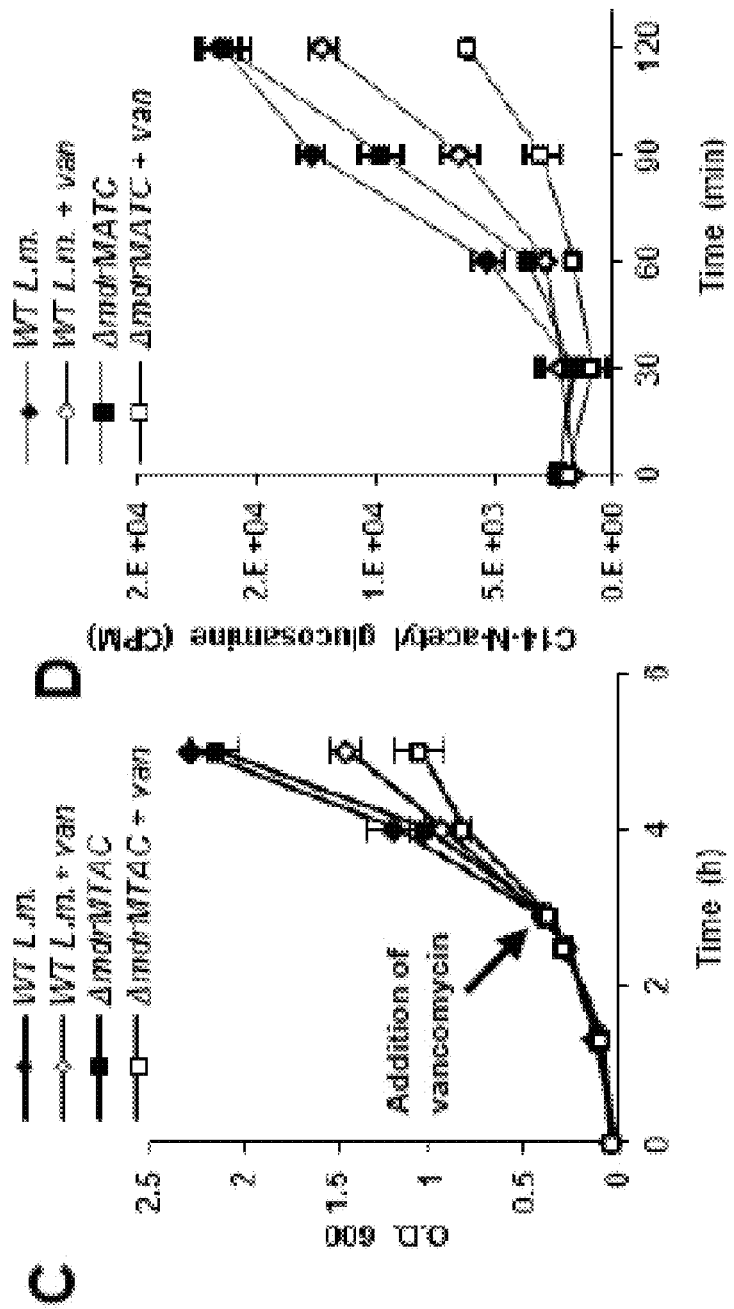
FIGs. 5C-D

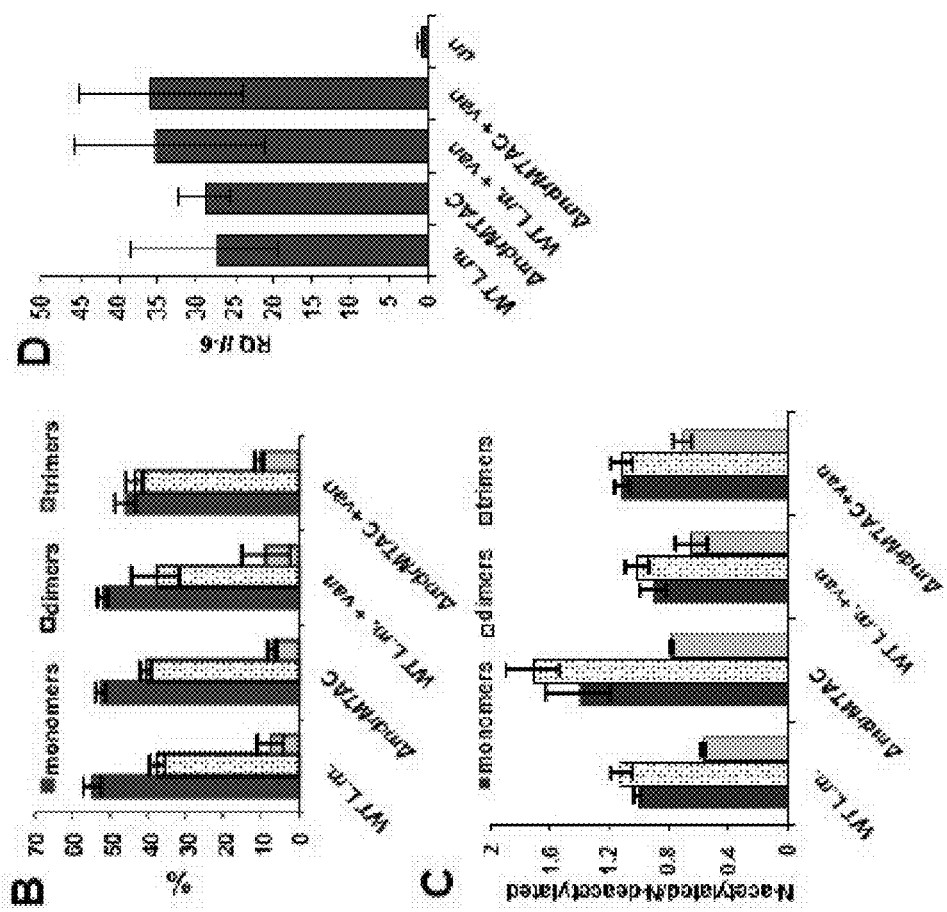

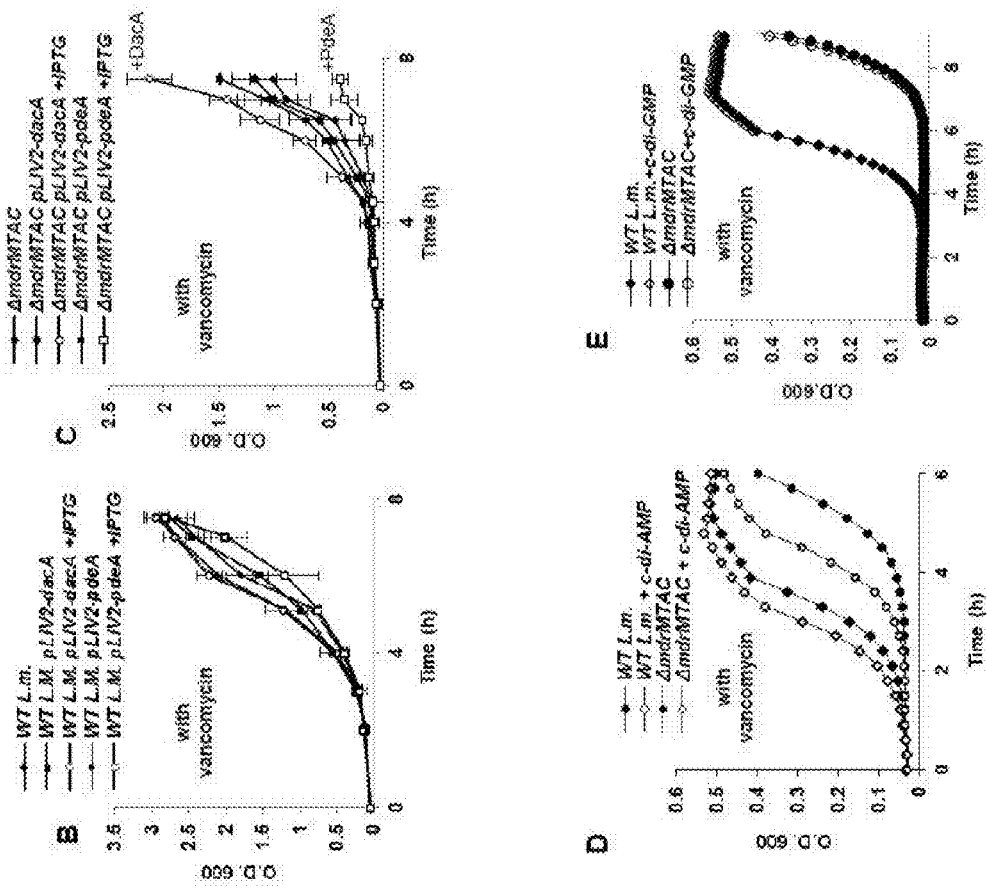
FIGS. 7B-E

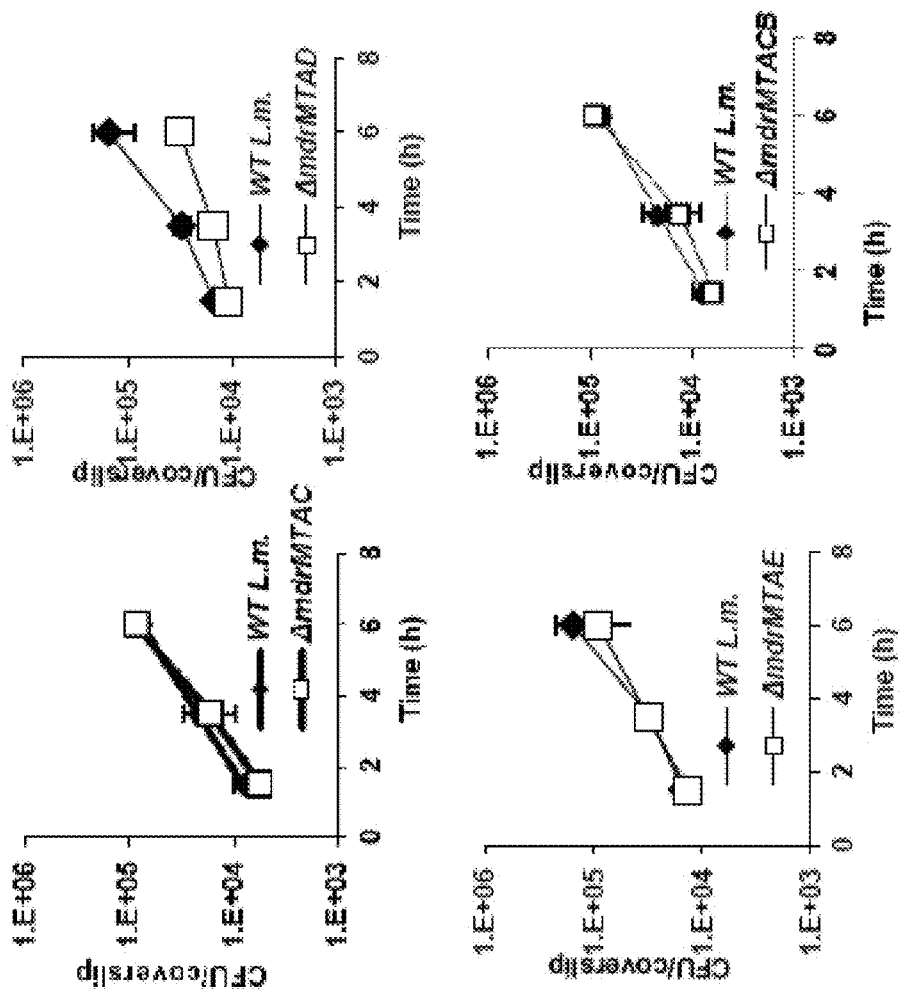

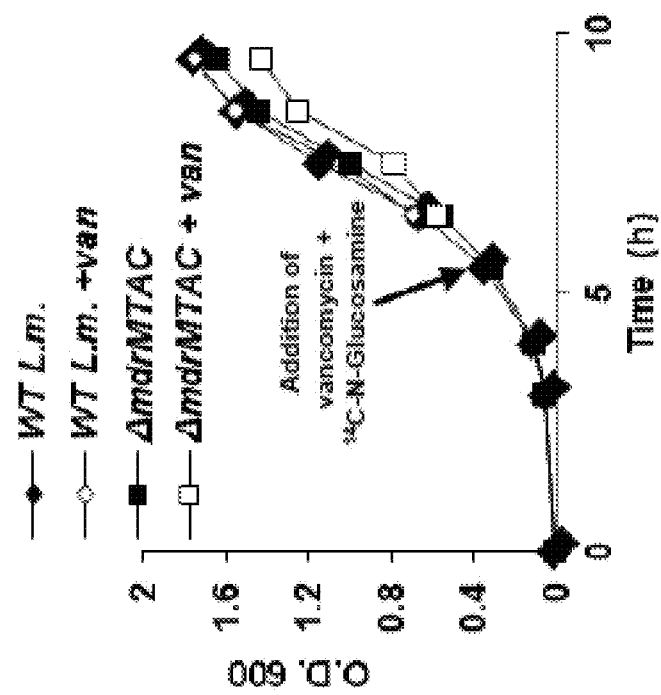

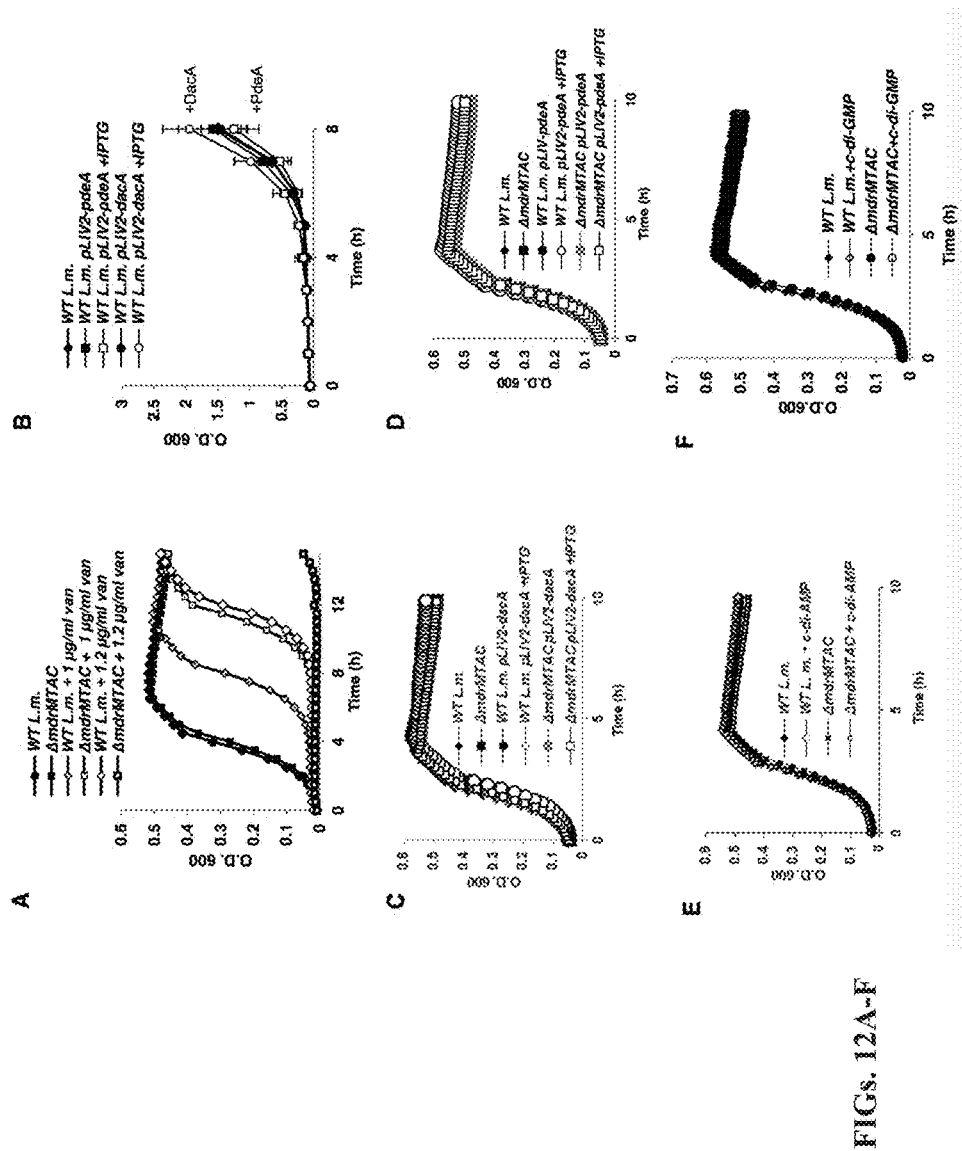
FIGS. 12A-F

US 9,976,149 B2

MODIFIED LISTERIA BACTERIA AND USES THEREOF

RELATED APPLICATION

This application claims the benefit of priority under 35 USC 119(e) of U.S. Provisional Patent Application No. 61/990,220 filed May 8, 2014, the contents of which are incorporated herein by reference in their entirety.

SEQUENCE LISTING STATEMENT

The ASCII file, entitled 62127SequenceListing.txt, created on May 7, 2015, comprising 56,799 bytes, submitted concurrently with the filing of this application is incorporated herein by reference.

FIELD AND BACKGROUND OF THE INVENTION

The present invention, in some embodiments thereof, relates to Listeria bacteria having mutations in their multidrug resistance transporters. In some embodiments, the bacteria can be used as vaccines, adjuvants and as DNA delivery vehicles.

Strains of Listeria monocytogenes have recently been developed as intracellular delivery vehicles of heterologous proteins providing delivery of antigens to the immune system to induce an immune response to clinical conditions that do not permit injection of the disease-causing agent, such as cancer (U.S. Pat. No. 6,051,237; U.S. Pat. No. 6,565,852) and HIV (U.S. Pat. No. 5,830,702). Since L. monocytogenes is a Gram-positive, food-borne human and animal pathogen responsible for serious infections in immunocompromised individuals and pregnant women, strains of these bacteria must be attenuated in a manner that reduces toxicity to the host, while maintaining immunogenicity of the vaccine.

As a facultative intracellular bacterium, L. monocytogenes elicits both humoral and cell-mediated bacterial antigen-specific immune responses. Following entry of the Listeria into a cell of the host organism, the Listeria produces Listeria-specific proteins that enable it to escape from the phagolysosome of the engulfing host cell into the cytosol of that cell. In the cell, L. monocytogenes proliferates, expressing proteins necessary for survival, but also expressing heterologous genes operably linked to Listeria promoters. Presentation of peptides of these heterologous proteins on the surface of the engulfing cell by MHC proteins permit the development of a T cell response. During infection, L. monocytogenes triggers a robust type I interferon response, as manifested by enhanced expression and secretion of the cytokine beta interferon (IFN-β).

A previous study aimed at identifying L. monocytogenes determinants involved in IFN-β activation identified multidrug resistance (MDR) transporters as modulators of the type I interferon response in vivo (Crimmins et al., Proc. Natl. Acad. Sci. U.S.A. 105:10191-10196). Specifically, overexpression in bacteria of two closely related MDR transporters, MdrM and MdrT, was found to trigger enhanced induction of IFN-β by infected macrophages. However, only deletion of the mdrM gene resulted in reduced levels of IFN-β secreted by infected macrophages. This observation indicated that MdrM plays an active role during bacterial cytosolic growth that leads to induction of the type I interferon response.

It was recently proposed that MdrM and MdrT transporters extrude cyclic-di-adenosine monophosphate (c-di-AMP) during L. monocytogenes intracellular growth, which in turn activates infected macrophages to elicit the IFN-β response (11, 12). Indeed, c-di-AMP activates a robust type I interferon response when added exogenously, however, a physiological association between c-di-AMP and the MDR transporters was not established. Notably, several reports had indicated that c-di-AMP serves as a second messenger molecule that influences central cellular processes of bacteria e.g., genome surveillance, response to cell wall stresses and, more recently, peptidoglycan homeostasis (13-17). In bacteria c-di-AMP is synthesized by diadenylate cyclase (DAC) using ATP as a substrate and conversely, linearized to 5'pApA by a specific c-di-AMP phosphodiesterase (PDE) (15). While it was shown that the level of c-di-AMP is largely dependent on the expression levels of DAC and PDE enzymes (15, 18), the mechanism coordinating the activity of these enzymes is not known. The prevalence of DAC domains among bacteria and archaea strengthens the premise that this c-di-AMP is fundamentally involved in microbial physiology (13). L. monocytogenes genome encodes both c-di-AMP dac and pde genes (dacA: lmo2120 and pdeA: lmo0052). dacA gene was shown to be essential for growth and the one responsible for c-di-AMP production, while pdeA was shown to degrade c-di-AMP (11, 18).

Additional background art includes WO 2008/066774 and U.S. Patent Application No. 20110027319.

SUMMARY OF THE INVENTION

According to an aspect of some embodiments of the present invention there is provided a Listeria bacterium comprising a first mutation in the multidrug resistance transporter M (MdrM) gene which causes a decrease in interferon-β production in macrophages as compared to wild-type Listeria bacterium and a second mutation in the multidrug resistance transporter T (MdrT) gene which causes a decrease in interferon-β production in macrophages as compared to the wild-type Listeria bacterium.

According to an aspect of some embodiments of the present invention there is provided a vaccine comprising the Listeria bacterium described herein.

According to an aspect of some embodiments of the present invention there is provided a method of eliciting or boosting a cellular immune response in a subject comprising administering to the subject an effective amount of the vaccine described herein, thereby eliciting or boosting the cellular immune response.

According to an aspect of some embodiments of the present invention there is provided an article of manufacture comprising the Listeria bacterium described herein and an immunogen.

According to an aspect of some embodiments of the present invention there is provided a method of eliciting or boosting a cellular immune response in a subject comprising administering to the subject an effective amount of the article of manufacture described herein, thereby eliciting or boosting the cellular immune response.

According to an aspect of some embodiments of the present invention there is provided a method of expressing a molecule of interest in a cell comprising infecting the cell with the Listeria bacterium described herein, wherein the molecule of interest is encoded by the heterologous nucleic acid.

According to some embodiments of the invention, the Listeria bacterium decreases interferon-β production in macrophages as compared to a *Listeria* bacterium having the first mutation in the MdrM gene, but not having the second mutation in the MdrT gene.

According to some embodiments of the invention, the *Listeria* bacterium decreases interferon-β production in macrophages as compared to a *Listeria* bacterium having the first mutation in the MdrT gene, but not having the second mutation in the to MdrM gene.

According to some embodiments of the invention, the decrease in interferon-β production is measured by PCR.

According to some embodiments of the invention, the bacteria further comprise at least one additional mutation in a multidrug resistance transporter gene selected from the group consisting of MdrA gene, MdrB gene, MdrC gene, MdrD gene and MdrE gene.

According to some embodiments of the invention, the bacterium further comprise at least one additional mutation in a multidrug resistance transporter gene selected from the group consisting of MdrA gene and MdrC gene.

According to some embodiments of the invention, the *Listeria* bacterium further comprises at least one additional mutation in the MdrA gene and at least one additional mutation in the MdrC gene, wherein each of the additional mutation causes a decrease in interferon-β production in macrophages as compared to wild-type *Listeria* bacterium as measured by PCR.

According to some embodiments of the invention, the *Listeria* bacterium further comprises at least one additional mutation in the MdrB gene.

According to some embodiments of the invention, the additional mutation causes a decrease in interferon-β production in macrophages as compared to wild-type *Listeria* bacterium as measured by PCR.

According to some embodiments of the invention, the mutation is a deletion mutation.

According to some embodiments of the invention, the first mutation is a point mutation.

According to some embodiments of the invention, the point mutation is a phenylalanine to valine substitution at position 58.

According to some embodiments of the invention, the point mutation is in the substrate binding pocket of the multidrug resistance transporter M.

According to some embodiments of the invention, the point mutation is effected at a position which comprises the residues W49, W141, W166 and F58.

According to some embodiments of the invention, the *Listeria* bacterium is *Listeria monocytogenes*.

According to some embodiments of the invention, the *Listeria* bacterium is attenuated.

According to some embodiments of the invention, the *Listeria* bacterium further comprises a heterologous nucleic acid.

According to some embodiments of the invention, the heterologous nucleic acid is integrated into the *Listeria* chromosome.

According to some embodiments of the invention, the heterologous nucleic acid encodes at least one polypeptide product.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D. MdrM transporter function is required for activation of the IFN-β response during macrophage infection. (A) Western blot analysis of bacterial membrane fraction probed for 6His-tagged MdrM and MdrM-F58V (using HisProb-HPR) expressed from the IPTG inducible vector pLIV2, with and without IPTG. (B) Growth in the presence of R6G (3.5 μM) of WT *L. monocytogenes*, ΔmdrM mutant and ΔmdrM mutant harboring pLIV2 expressing MdrM-6His or MdrM-F58V-6His, to with and without IPTG (1 mM) in BHI. Experiment was performed in a 96-well format in a Synergy HT Biotek® plate reader. Growth curves from one representative experiment are shown. Error bars representing standard deviation of a triplicate are hidden by the symbols. (C) Intracellular growth curves of WT *L. monocytogenes*, ΔmdrM mutant or ΔmdrM mutant harboring pLIV2 expressing MdrM-6His or MdrM-F58V-6His, with and without IPTG, in RAW264 macrophage cells. Representative growth curves are shown. Error bars represent standard deviation of 3 biological repeats. (D) RT-qPCR analysis of IFN-β transcriptional levels in macrophages infected with WT *L. monocytogenes*, ΔmdrM mutant or ΔmdrM mutant harboring pLIV2 expressing MdrM-6His or MdrM-F58V-6His, with and without IPTG, at 6 hours post infection (h.p.i.). Transcription levels are represented as relative quantity (RQ), relative to levels in uninfected cells (un). The data is an average of 3 independent experiments. Error bars represent 95% confidence interval. * $P<0.01$ compared to all the rest of the samples. The data in A-C are representative of at least 3 independent biological repeats.

FIG. 2. Transcription of MdrM transporter homologs is induced during *L. monocytogenes* intracellular growth. Transcription analysis of mdrM-like transporter genes during *L. monocytogenes* 10403S intracellular growth in BMD macrophage cells at 6 h.p.i. in comparison to their levels during exponential growth in BHI medium using RT-qPCR analysis. Transcription levels are represented as relative quantity (RQ), relative to the transcription levels during growth in BHI. If the transcript levels are equal in both conditions the RQ=1. Transcription levels were normalized to the levels of 16S rRNA as a reference gene. The data is representative of 3 independent biological repeats (N=3). Error bars represent 95% confidence interval (as described in materials and methods).

FIGS. 3A-C. MdrM-like transporters are responsible for most of the type I interferon induction upon *L. monocytogenes* infection. (A) RT-qPCR analysis of IFN-β transcriptional levels in BMD macrophages infected with WT *L.*

Figure 1:
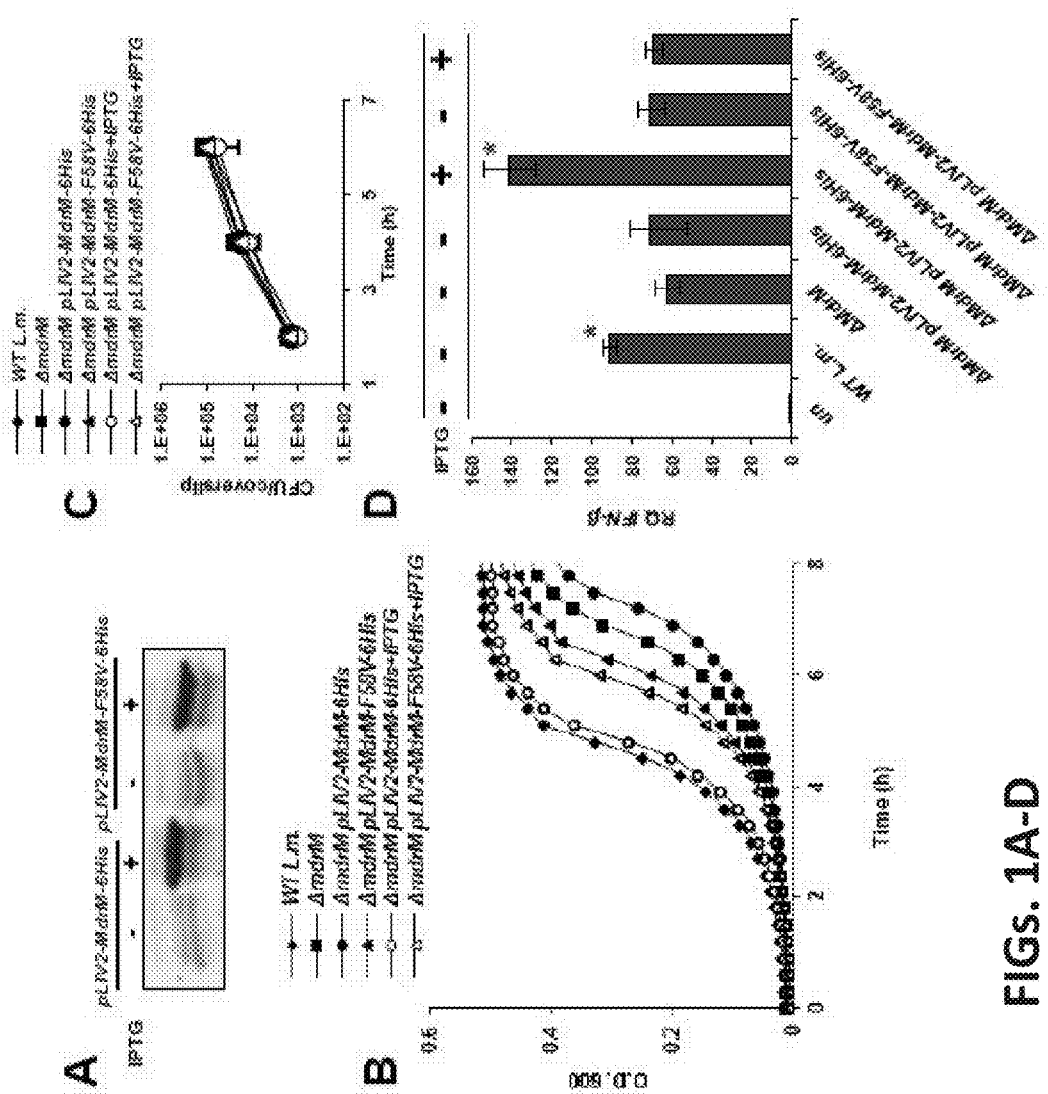

*monocytogenes* or MDR deletion mutants. (B) RT-qPCR analysis of IL-6 and IL-1α induction in BMD macrophages infected with WT *L. monocytogenes* in comparison to ΔmdrMTAC mutant. Transcription levels are represented as relative quantity (RQ), relative to uninfected cells (un). Data in (A) and (B) represents at least 3 biological repeats. Error bars represent 95% confidence interval (as described in materials and methods). (C) Intravenous infection of C57BL/6 mice with WT *L. monocytogenes* and ΔmdrMTAC mutant. Bacterial colony forming units (CFUs) were numerated at 72 h.p.i. from livers and spleens taken from 10 infected mice for each strain. The results are mean of 2 independent experiments in which 5 mice were infected in each group. Horizontal bars represent the mean. P value was calculated using student's t test.

FIGS. 4A-C. MdrM-like transporters are required for cell wall stress responses. (A) RT-qPCR analysis, presented as a heat map, of transcriptional levels of mdrM, mdrT, mdrA, mdrC, and hly genes in WT *L. monocytogenes* grown under different in vitro conditions: BHI supplemented with vancomycin (1 µg ml$^{-1}$), penicillin G (0.08 µg ml$^{-1}$), lincomycin (3 µg ml$^{-1}$), or rhodamine 6G (50 µM); LB Mops G1P charcoal, minimal media pH 7, minimal media pH 5, or minimal media with $H_2O_2$ at pH 5. Transcription levels are represented as relative quantity (RQ), relative to the levels in BHI or in minimal media pH 7, respectively. Data represents 3 biological repeats. In all samples statistical deviation did not exceed 15% with 95% confidence level. (B) RT-qPCR analysis of transcriptional levels of mdrM, mdrT, mdrA, and mdrC genes in WT *L. monocytogenes* grown in BHI supplemented with vancomycin (1 µg ml$^{-1}$) or penicillin G (0.08 µg ml$^{-1}$) for 2 h. Transcription levels (RQ) are relative to the levels in BHI without drugs. Data represents 3 biological repeats. Error bars represent 95% confidence interval. (C) Growth curve of WT *L. monocytogenes* and MDR mutants in BHI media supplemented with vancomycin (1 µg ml$^{-1}$) or penicillin G (0.08 µg ml$^{-1}$). Data represents 3 biological repeats. Experiment was performed in a 96-well format in a Synergy HT Biotek® plate reader. Representative growth curves are shown. Error bars representing standard deviation of the triplicate are hidden by the symbols. Growth curves were performed in at least 3 independent biological repeats.

FIGS. 5A-D. ΔmdrMTAC mutant does not over-produce peptidoglycan in response to vancomycin stress. (A) Negative staining TEM images of WT *L. monocytogenes* and ΔmdrMTAC mutant grown with and without vancomycin treatment. Growth curves presented in panel C. (B) TEM section images of WT *L. monocytogenes* and ΔmdrMTAC mutant grown with and without vancomycin treatment. Growth curves presented in panel C. Images in (A) and (B) represents 3 independent biological repeats, a total of 35 frames were taken for each strain and to condition. (C) Growth curves of bacteria taken to TEM analysis (panel A-B). Vancomycin (1 µg ml$^{-1}$) was added at O.D.$_{600}$ 0.4 and bacteria were harvested 2 hours later for fixation and staining. The data is a mean of 3 independent biological experiments. Error bars represent standard deviation. (D) Analysis of peptidoglycan synthesis rate in WT *L. monocytogenes* and ΔmdrMTAC mutant, grown with and without vancomycin (0.8 µg ml$^{-1}$) treatment, as measured by incorporation of [$^{14}$C]—N-acetylglucosamine. Vancomycin and N-acetylglucosamine were added during bacterial growth at O.D.$_{600}$ 0.4 and incorporation of [$^{14}$C]—N-acetylglucosamine was analyzed at 30 min intervals upon addition (growth curves presented in FIG. 11). Error bar represents standard deviation of triplicate samples. The data represents 2 biological repeats.

FIGS. 6A-D. MdrM-like transporters do not impact peptidoglycan composition. (A) HPLC analysis of cell wall derived muropeptides of WT *L. monocytogenes* and ΔmdrMTAC bacteria, grown with and without vancomycin (van) treatment. HPLC peaks associated with N-acetylated muropeptides are marked as Ac, and peaks associated with N-deacetylated muropeptides are marked as Deac. The peak highlighted with a "*" corresponds to O-acetylated monomer. The data represents 5 biological repeats. (B) Degree of muropeptide cross-linking, presented as the percentage of monomer, dimer and trimer muropeptides (based on integrated area of the corresponding peaks in the HPLC analysis) of WT *L. monocytogenes* or ΔmdrMTAC mutant grown with and without vancomycin treatment. The data is a mean of 5 biological repeats. Error bar represents standard deviation of the independent samples. (C) The degree of peptidoglycan N-acetylation in muropeptides derived from WT *L. monocytogenes* or ΔmdrMTAC mutant grown with and without vancomycin treatment, presented as the ratio of the integrated area of peaks corresponding to N-acetylated/N-deacetylated muropeptides for monomeric, dimeric and trimeric units in the HPLC analysis. The data is a mean of 5 biological repeats. Error bar represents standard deviation of the independent samples. (D) RT-qPCR analysis of IL-6 transcriptional levels in BMD macrophages treated for 6 h with cell wall extracts derived from WT *L. monocytogenes* and ΔmdrMTAC bacteria, grown with and without vancomycin (van, 1 µg ml$^{-1}$). Transcription levels are represented as relative quantity (RQ), relative to levels in untreated cells (un). The data represents 3 biological repeats. Error bars represent 95% confidence interval (as described in to materials and methods).

FIGS. 7A-E. Mdr-MTAC transporters and c-di-AMP are functionally associated in the response to cell wall stress. (A) RT-qPCR analysis of transcriptional levels of dacA gene in WT *L. monocytogenes* and ΔmdrMTAC bacteria grown in BHI or supplemented with vancomycin (van, 1 µg ml$^{-1}$ for 2 hours or 20 µg ml$^{-1}$ for 10 minutes). Transcription levels are represented as relative quantity (RQ), relative to the levels in BHI alone. Data represents 3 biological independent repeats. Error bars represent 95% confidence interval (as described in materials and methods). (B) Growth curves of WT *L. monocytogenes* strains harboring the pLIV2 plasmid with an IPTG inducible promoter, expressing dacA or pdeA genes in BHI supplemented with vancomycin (1 µg ml$^{-1}$) with or without IPTG. Experiment was performed in flasks. The data is a mean of 3 independent biological experiments. Error bars represent standard deviation. (C) Growth curves of ΔmdrMTAC bacteria harboring the pLIV2 plasmid with an IPTG inducible promoter, expressing dacA or pdeA genes in BHI supplemented with vancomycin with or without IPTG. Experiment was performed in flasks. The data is a mean of 3 independent biological experiments. Error bars represent standard deviation. (D) Growth curve of WT *L. monocytogenes* or ΔmdrMTAC mutant in BHI supplemented with vancomycin with and without addition of 3 µg ml$^{-1}$ c-di-AMP. This experiment was performed in 3 biological repeats in a 96-well format in a Synergy HT BIOTEK® plate reader. Growth curves from one representative experiment are shown. Error bars representing standard deviation of a triplicate are hidden by the symbols. (E) Growth curve of WT *L. monocytogenes* or ΔmdrMTAC mutant in BHI supplemented with vancomycin with and without addition of 3 µg ml$^{-1}$ c-di-GMP. The experiment was performed in 3 biological repeats in a 96-well format in a Synergy HT BIOTEK® plate reader. Growth curves from one representative experiment are shown. Error bars representing standard deviation of a triplicate are hidden by the symbols.

Figure 8A:
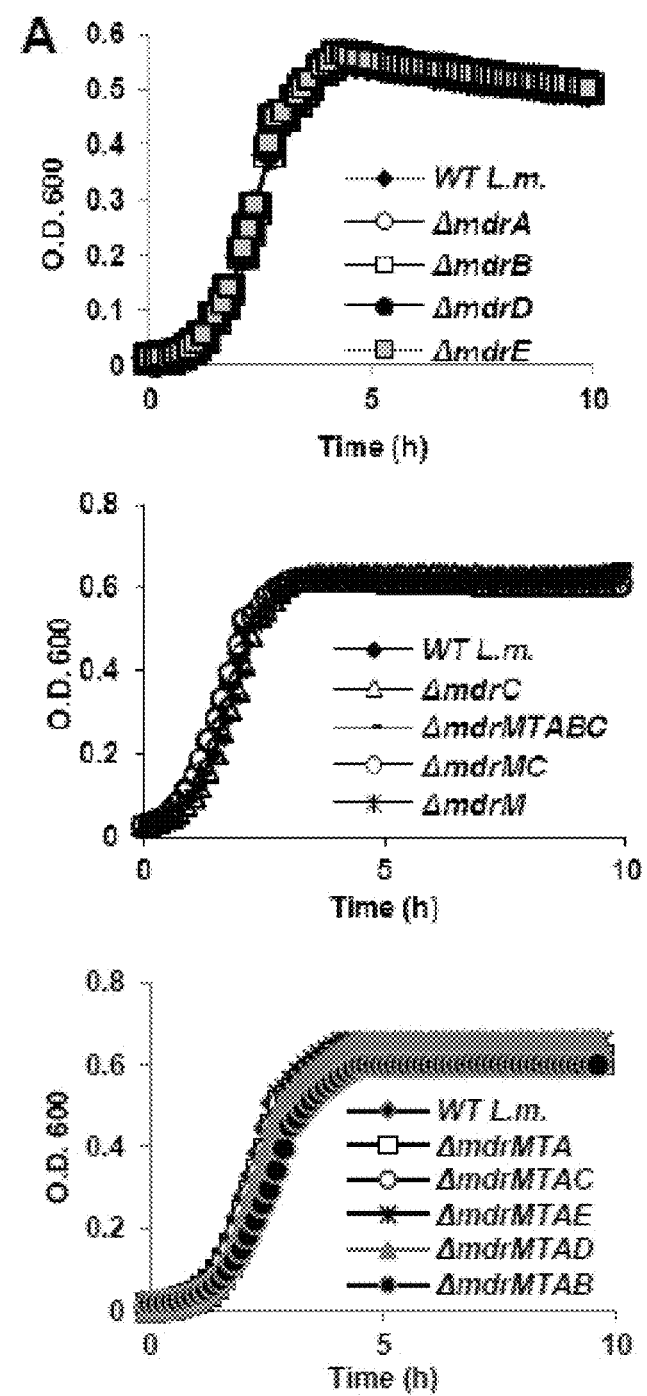
Figure 8B:
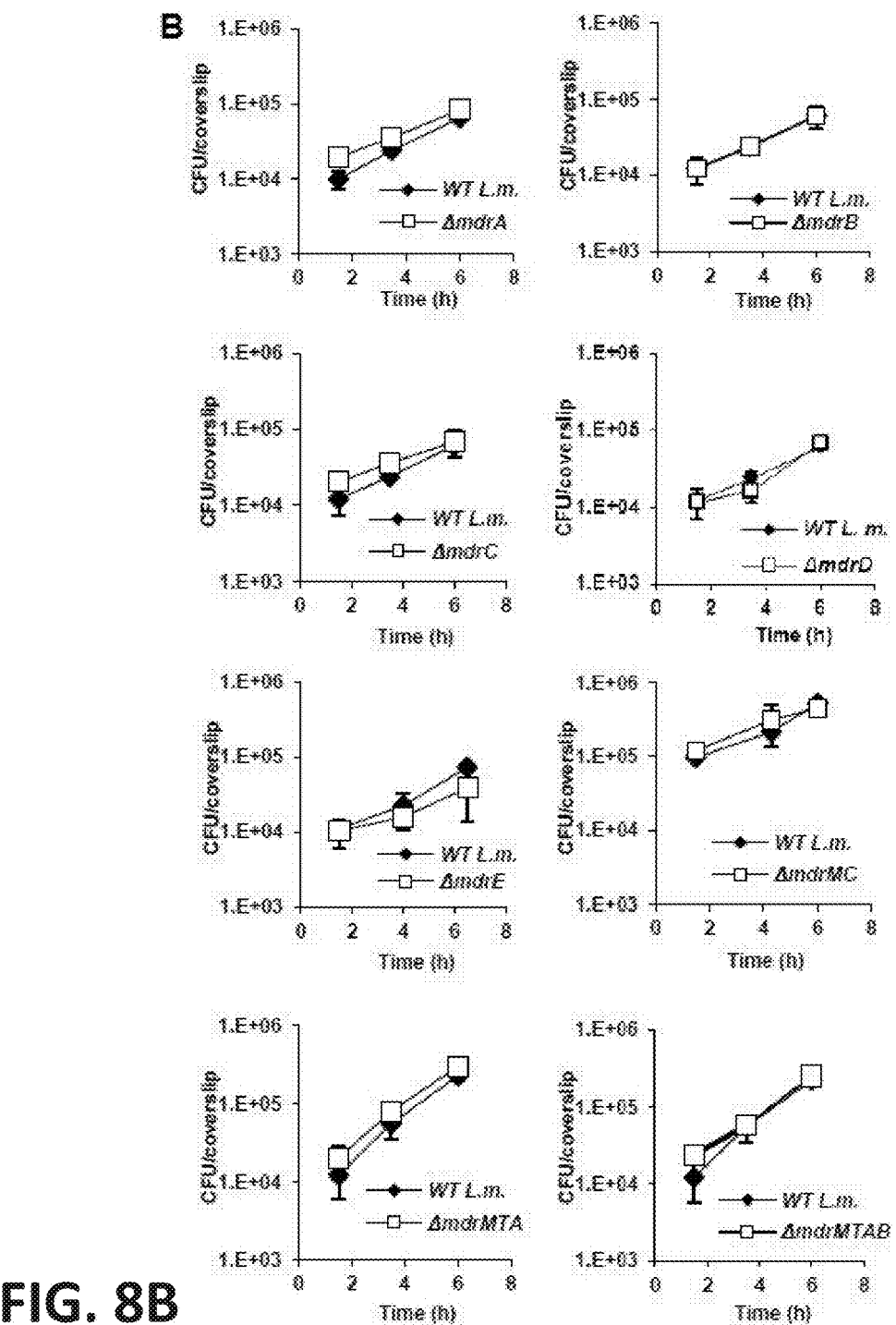

FIGS. 8A-B. Growth analysis of MDR deletion mutants. (A) Growth curves of WT *L. monocytogenes* and MDR mutants in BHI broth. (B) Intracellular growth curves of WT *L. monocytogenes* and MDR mutants in BMD macrophage cells. The growth curves represent 3 biological independent repeats. Error bars represent standard deviation of a triplicate (hidden by the symbols in panel A).

Figure 9:
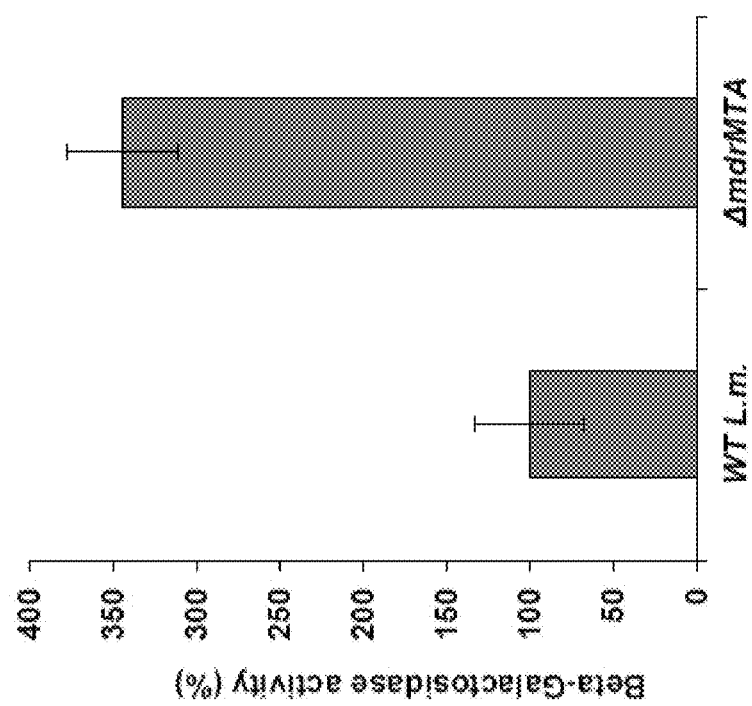

FIG. 9. Transcription analysis of mdrC gene in ΔmdrMTA and WT bacteria. The relative activity of mdrC promoter was assayed in WT and ΔmdrMTA *L. monocytogenes* bacteria using the lacZ reporter gene. mdrC promoter region was cloned up-stream the lacZ gene in the integrative plasmid pPL2. Beta-galactosidase activity of WT bacteria was set as 100%.

Figure 10:
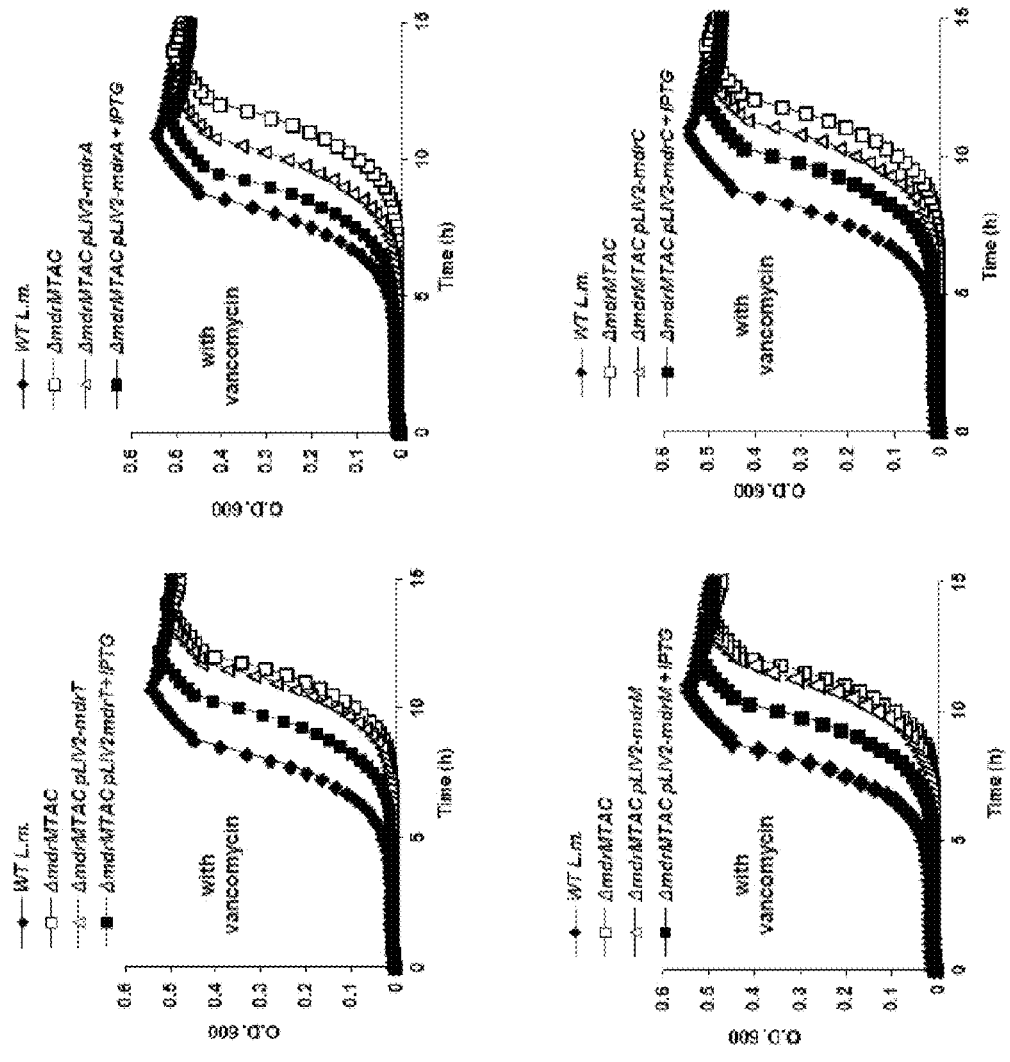

FIG. 10. Complementation experiments of ΔmdrMTAC mutant. Growth analysis of WT *L. monocytogenes*, ΔmdrMTAC mutant and ΔmdrMTAC mutant complemented with pLIV2 plasmid expressing each one of the MTAC transporters (with and without IPTG). Experiments were performed in a 96-well format in a Synergy HT BIOTEK® plate reader. Error bars representing standard deviation of the triplicate are hidden by the symbols. Growth curves from one representative experiment are shown. Experiment was repeated independently 3 times.

FIG. 11. Growth curves of WT *L. monocytogenes* and ΔmdrMTAC mutant in BHI media, with and without 0.8 μg ml$^{-1}$ of vancomycin (van). The vancomycin concentration used in this experiment was lower than the one used in FIG. 5C. Arrow indicates addition of [$^{14}$C]—N-acetylglucosamine and vancomycin.

FIGS. 12A-F. Effect of c-di-AMP on *L. monocytogenes* growth with and without vancomycin stress. (A) Growth curves of WT *L. monocytogenes* and ΔmdrMTAC mutant with and without vancomycin. Two vancomycin concentrations were used: 1 and 1.2 μg ml$^{-1}$. Bacteria were grown in a 96 well microplate reader. (B) Growth curves of WT *L. monocytogenes* strains harboring the pLIV2 plasmid with an IPTG inducible promoter, expressing dacA or pdeA genes in BHI supplemented with vancomycin (1.2 μg ml$^{-1}$) with or without IPTG. Experiment was performed in flasks. The data is a mean of 3 independent biological experiments. Error bars represent standard deviation. (C) Growth curves of WT *L. monocytogenes* and ΔmdrMTAC mutant harboring pLIV2-dacA plasmid in BHI with and without IPTG addition. (D) Growth curves of WT *L. monocytogenes* and ΔmdrMTAC mutant harboring pLIV2-pdeA plasmid in BHI with and without IPTG addition. (E) Growth curves of WT *L. monocytogenes* or ΔmdrMTAC mutant in BHI with and without addition of 3 μg ml$^{-1}$ of purified c-di-AMP or c-di-GMP (F). Experiments were performed in a 96-well format in a Synergy HT BIOTEK® plate reader. Error bars representing standard deviation of the triplicate are hidden by the symbols. Growth curves from one representative experiment are shown. Experiment was repeated independently 3 times.

DESCRIPTION OF SPECIFIC EMBODIMENTS OF THE INVENTION

The present invention, in some embodiments thereof, relates to *Listeria* bacteria having mutations in their multidrug resistance transporters. In some embodiments, the bacteria can be used as vaccines, adjuvants and as DNA delivery vehicles.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As a facultative intracellular bacterium, *L. monocytogenes* elicits both humoral and cell-mediated bacterial antigen-specific immune responses.

Strains of *Listeria monocytogenes* have been developed as intracellular delivery vehicles of heterologous proteins providing delivery of antigens to the immune system to induce an immune response to clinical conditions such as cancer and HIV.

Since *L. monocytogenes* is a Gram-positive, food-borne human and animal pathogen responsible for serious infections in immunocompromised individuals and pregnant women, strains of these bacteria must be attenuated in a manner that reduces toxicity to the host, while maintaining immunogenicity of the vaccine.

WO2008066774 teaches attenuated *L. monocytogenes* bacteria strains that include a mutation, which modulates the expression of one of the multidrug resistance transporters (MdrL, MdrT gene or MdrM). These strains elicit a decreased interferon-β production in macrophages. It was shown that only deletion of the mdrM gene resulted in reduced levels of IFN-β secreted by infected macrophages.

The present inventors have now discovered that not only MdrM, but also a set of related putative MDR transporters together mediate IFN-β induction in infected macrophages. Specifically, the present inventors show that four homologous *L. monocytogenes* MDR transporters not only trigger IFN-β induction during infection but also are novel players in the response to cell wall stress. Remarkably, the ΔmdrMTAC mutant lacking the four transporters failed to trigger enhanced production of PGN in response to vancomycin stress, a mechanism known to facilitate to vancomycin resistance.

Overall, it was observed that the greater the number of transporters that were deleted, the lower the IFN-β levels expressed by infected cells (FIG. 3A). Notably, macrophages infected with the quadruple mutant named ΔmdrMTAC (deleted of mdrM, mdrT, mdrA and mdrC genes) exhibited the lowest IFN-β level among the tested mutants, approximately 15% the amount of IFN-β relative to macrophages infected with WT bacteria. Thus, the present inventors propose that mutants which contain a mutation in mdrM and at least one other multidrug resistance transporter will be more effective at lowering the level of IFN-β in macrophages than a bacterium that has a mutation in mdrM alone.

The subject bacteria find use in a variety of applications, where representative applications of interest include, but are not limited to: (a) use of the subject bacteria as adjuvants; (b) use of the subject bacteria as delivery vectors for introducing macromolecules into a cell; (c) use of the subject bacteria as vaccines for eliciting or boosting a cellular immune response; etc.

Thus, according to a first aspect of the present invention there is provided a *Listeria* bacterium comprising a first mutation in the multidrug resistance transporter M (mdrM) gene which causes a decrease in interferon-β production in macrophages as compared to wild-type *Listeria* bacterium and a second mutation in the multidrug resistance transporter T (mdrT) gene which causes a decrease in interferon-β production in macrophages as compared to the wild-type *Listeria* bacterium.

The *Listeria* bacterium of this aspect of the present invention may be any of the 10 species of the *Listeria* genus. According to a particular embodiment, the *Listeria* bacterium is *L. monocytogenes*.

Exemplary strains of *Listeria* bacteria contemplated by the present invention are provided in U.S. Pat. No. 8,580,939, incorporated herein by reference.

The *Listeria* bacterium of this aspect of the present invention comprise at least two mutations, a first mutation in the multidrug resistance transporter M (mdrM) gene and a second mutation in the mdrT gene. The mutation in the mdrM gene is such that it causes a decrease in interferon-β production in macrophages as compared to a wild-type *Listeria* bacterium and the mutation in the mdrT gene is such that it causes a decrease in interferon-β production in macrophages as compared to the wild-type *Listeria* bacterium.

In some embodiments, the mutant *Listeria* bacteria decrease interferon-β production as compared to the same species of *Listeria* bacteria that do not include the mutations (i.e. wild-type). Wild type *Listeria* bacteria are those that do not have any mutations in the genes encoding multidrug resistance transporters and preferably do not have mutations in other genes which affect interferon-β production. Thus, wild-type *listeria* typically express the genes:

mdrM gene, mdrT gene, mdrA gene, mdrB gene, mdrC gene, mdrD gene and mdrE.

mdrM gene, Gene ID: 12553832 SEQ ID NO: 1; protein SEQ ID NO: 2 WP_003723582.1 mdrT gene, Gene ID: 12554851 SEQ ID NO: 3; protein SEQ ID NO: 4WP_014601165.1 mdrA gene, Gene ID: 12552738 SEQ ID NO: 5; protein SEQ ID NO: 6 WP_014600553.1 mdrB gene, Gene ID: 12555124 SEQ ID NO: 7; protein SEQ ID NO: 8 WP_014601249.1 mdrC gene, Gene ID: 12555097 SEQ ID NO: 9; protein SEQ ID NO: 10 WP_003722177.1 mdrD gene, Gene ID: 12553093 SEQ ID NO: 11; protein SEQ ID NO: 12 WP_014600663.1 mdrE gene, Gene ID: 12555105 SEQ ID NO: 13; protein SEQ ID NO: 14 WP_014601241.1

According to another embodiment, the mutant *Listeria* bacteria reduce interferon-β production in macrophages to a greater extent than *Listeria* bacteria (of the same species) that have the identical first mutation in the mdrM gene, but are lacking the second mutation in the mdrT gene (and in all other respects are identical to the mutant *Listeria* bacteria described herein).

According to still another embodiment, the mutant *Listeria* bacteria reduce interferon-β production in macrophages to a greater extent than *Listeria* bacteria (of the same species) that have the identical second mutation in the mdrT gene, but are lacking the first mutation in the mdrM gene, (and in all other respects are identical to the mutant *Listeria* bacteria described herein).

In such embodiments, the decrease in interferon-β production in macrophages to is from about 1.5-fold decrease to about 50-fold decrease or more, including about 2-fold decrease to about 45-fold decrease, about 5-fold decrease to about 40-fold decrease, about 10-fold decrease to about 35-fold decrease, about 15-fold decrease to about 30-fold decrease, about 20-fold decrease to about 30-fold decrease, and the like.

Analyzing the effect of the mutants on interferon-β production in macrophages may be carried out on isolated macrophages (e.g. macrophage cell culture). Macrophages may be obtained from the bone marrow. According to another embodiment, the macrophages are comprised in a bone marrow cell culture. The macrophages are typically derived from a mammalian source—e.g. mouse, rat, human etc.

Methods of measuring interferon-β are known in art and include measuring on the RNA level and/or the protein level.

The protein sequence of human interferon-β is set forth in SEQ ID NO: 16; AAC41702.1.

The protein sequence of mouse interferon-β is set forth in SEQ ID NO: 18; NP_034640.1.

The mRNA sequence of human interferon-β is set forth in SEQ ID NO: 15; M25460.1.

The mRNA sequence of mouse interferon-β is set forth in SEQ ID NO: 17; NM_010510.1.

Methods of Detecting the Expression Level of RNA

The expression level of the interferon-β RNA in the cells of some embodiments of the invention can be determined using methods known in the arts.

Northern Blot Analysis:

This method involves the detection of a particular RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, colorimetric reaction or chemiluminescence. This method allows to both quantitation of an amount of particular RNA molecules and determination of its identity by a relative position on the membrane which is indicative of a migration distance in the gel during electrophoresis.

RT-PCR Analysis:

First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA In Situ Hybridization Stain:

In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the bound probe is detected using known methods. For example, if a radio-labeled probe is used, then the slide is subjected to a photographic emulsion which reveals signals generated using radio-labeled probes; if the probe was labeled with an enzyme then the enzyme-specific substrate is added for the formation of a colorimetric reaction; if the probe is labeled using a fluorescent label, then the bound probe is revealed using a fluorescent microscope; if the probe is labeled using a tag (e.g., digoxigenin, biotin, and the like) then the bound probe can be detected following interaction with a tag-specific antibody which can be detected using known methods.

In Situ RT-PCR Stain:

This method is described in Nuovo G J, et al. to [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

Methods of Detecting Expression and/or Activity of Proteins

Expression and/or activity level of proteins expressed in the cells of the cultures of some embodiments of the invention can be determined using methods known in the arts. Typically, antibodies which specifically recognize interferon-β are used.

Enzyme Linked Immunosorbent Assay (ELISA):

This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot:

This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane to which is indicative of a migration distance in the acrylamide gel during electrophoresis.

Radio-Immunoassay (RIA):

In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence Activated Cell Sorting (FACS):

This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical Analysis:

This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

In Situ Activity Assay:

According to this method, a chromogenic substrate is applied on the cells containing an active enzyme and the enzyme catalyzes a reaction in which the substrate is decomposed to produce a chromogenic product visible by a light or a fluorescent microscope.

In Vitro Activity Assays:

In these methods the activity of a particular enzyme is measured in a protein mixture extracted from the cells. The activity can be measured in a spectrophotometer well using colorimetric methods or can be measured in a non-denaturing acrylamide gel (i.e., activity gel). Following electrophoresis the gel is soaked in a solution containing a substrate and colorimetric reagents. The resulting stained band corresponds to the enzymatic activity of the protein of interest. If well calibrated and within the linear range of response, the amount of enzyme present in the sample is proportional to the amount of color produced. An enzyme standard is generally employed to improve quantitative accuracy.

According to a particular embodiment, interferon-β production is measured by infecting macrophages with the test and reference, e.g., wild-type, strains of bacteria. Following a period of time, e.g., 4 to 18 hours, the macrophage culture media is collected and the amount of Type I interferon secreted by the macrophages is detected using a reporter gene such as luciferase cloned under regulation of a Type I interferon promoter.

The mutant *Listeria* bacteria of the present invention may comprise mutations in additional genes. According to one embodiment the mutation to at least one of the additional genes serves to further reduce the interferon-β production in macrophages. According to another embodiment the mutations to each of the additional genes serve to further reduce the interferon-β production in macrophages. According to still another embodiment, the additional mutations are effected on Multidrug resistance (Mdr) transporter genes. According to still another embodiment, the mutations to each of the Mdr transporter genes serve to further reduce the interferon-β production in macrophages.

A "multidrug resistance transporter" as used herein refers to a protein (or polypeptide) which participates in conferring to a cell resistance to multiple cytotoxic insults. A multidrug resistance transporter may refer to a single polypeptide, one or more polypeptides acting sequentially or in concert, or a complex of polypeptides. In addition, a multidrug resistance transporter may participate, directly or indirectly, in the catalysis of energy-dependent extrusion of molecules or compounds out of a cell or their partitioning into a specific intracellular compartment.

According to a particular embodiment, the additional mutation is effected in the mdrA gene and/or the mdrC gene.

According to a particular embodiment, the additional mutation is effected in the mdrA gene and/or the mdrC gene and/or the mdrB gene.

According to another embodiment, the additional mutation is effected in the mdrA gene, mdrB gene, mdrC gene, mdrD gene and/or the mdrE gene.

According to yet another embodiment, the mutant *Listeria* bacteria carries a mutation in each of the genes mdrM, mdrT, mdrA and mdrC.

Generation of the subject mutant bacteria may be accomplished in a number of ways that are well known to those of skill in the art, including deletion mutagenesis, insertion mutagenesis, and mutagenesis which results in the generation of frameshift mutations, mutations which effect premature termination of a protein, or mutation of regulatory sequences which affect gene expression. Mutagenesis can be accomplished using recombinant DNA techniques or using traditional mutagenesis technology using mutagenic chemicals or radiation and subsequent selection of mutants. Representative protocols of different ways to generate mutant bacteria according to the present invention are provided in the Experimental Section, below.

According to a particular embodiment, the mutation in the mdrM gene is a point mutation. Preferably the point mutation is effected in the substrate binding pocket of the transporter e.g. at position W49, W141, W166 or F58.

An exemplary point mutation on the mdrM gene is a phenylalanine to valine substitution at position 58.

Exemplary mutations on the mdrA gene, mdrB gene, mdrC gene, mdrD gene and/or the mdrE are deletions of at least 50%, 60%, 70%, 80%, 90%, 95% or 100% of the sequence.

In certain embodiments, the mutant *Listeria* bacteria are attenuated.

The term "attenuation," as used herein, refers to a diminution in the ability of the bacterium to cause disease in an animal. In other words, the pathogenic characteristics of the attenuated *Listeria* strain have been lessened compared with wild-type *Listeria*, although the attenuated *Listeria* is capable of growth and maintenance in culture. Using as an example the intravenous inoculation of Balb/c mice with an attenuated *Listeria*, the lethal dose at which 50% of inoculated animals survive ($LD_{50}$) is preferably increased above the $LD_{50}$ of wild-type *Listeria* by at least about 10-fold, more preferably by at least about 100-fold, more preferably at least about 1,000 fold, even more preferably at least about 10,000 fold, and most preferably at least about 100,000-fold. An attenuated strain of *Listeria* is thus one which does not kill an animal to which it is administered, or is one which kills the animal only when the number of bacteria administered is vastly greater than the number of wild type non-attenuated bacteria which would be required to kill the to same animal. An attenuated bacterium should also be construed to mean one which is incapable of replication in the general environment because the nutrient required for its growth is not present therein. Thus, the bacterium is limited to replication in a controlled environment wherein the required nutrient is provided. The attenuated strains of the present invention are therefore environmentally safe in that they are incapable of uncontrolled replication.

In certain embodiments, the attenuated mutant *Listeria* bacteria according to the subject invention are ones that exhibit a decreased virulence compared to their corresponding wild type strain in the Competitive Index Assay as described in Auerbach et al., "Development of a Competitive Index Assay To Evaluate the Virulence of *Listeria monocytogenes* actA Mutants during Primary and Secondary Infection of Mice." Infection and Immunity. September 2001. p. 5953-5957. Vol. 69, No. 9. In this assay, mice are inoculated with test and reference, e.g., wild-type, strains of bacteria. Following a period of time, e.g., 48 to 60 hours, the inoculated mice are sacrificed and one or more organs, e.g., liver, spleen, are evaluated for bacterial abundance. In these embodiments, a given bacterial strain is considered to be less virulent if its abundance in the spleen is at least about 50-fold, or more, such as 70-fold or more less than that observed with the corresponding wild-type strain, and/or its abundance in the liver is at least about 10-fold less, or more, such as 20-fold or more less than that observed with the corresponding wild-type strain.

In yet other embodiments, bacteria are considered to be less virulent if they show abortive replication in less than about 8 hours, such as less than about 6 hours, including less than about 4 hours, as determined using the assay described in Jones and Portnoy, Intracellular growth of bacteria. (1994b) Methods Enzymol. 236:463-467. In yet other embodiments, bacteria are considered to be attenuated or less virulent if, compared to wild-type, they form smaller plaques in the plaque assay employed in the Experimental Section, below, where cells, such as murine L2 cells, are grown to confluency, e.g., in six-well tissue culture dishes, and then infected with bacteria. Subsequently, DME-agar containing gentamicin is added and plaques are grown for a period of time, e.g., 3 days. Living cells are then visualized by adding an additional DME-agar overlay, e.g., containing neutral red (GIBCO BRL) and incubated overnight. In such an assay, the magnitude in reduction in plaque size observed with the attenuated mutant as compared to the wild-type is, in certain embodiments, 10%, including 15%, such as 25% or more.

In certain embodiments, the mutant *Listeria* bacteria are killed but metabolically active (KBMA). The term "KBMA" or "killed but metabolically active" refers to bacteria that are attenuated for entry into non-phagocytic cells and attenuated with respect to cell-to-cell spread resulting in bacteria that have greatly reduced toxicity and yet the immunogenicity of the bacteria is maintained. Such *Listeria* bacteria may also comprise mutations in one or all uvr genes, i.e. uvrA, uvrB, uvrC, and uvrD genes as well as recA genes, or functionally equivalent genes, depending on the genus and species of the microbe. These mutations result in attenuation in the activity of the corresponding enzymes UvrA (an ATPase), UvrB (a helicase). UvrC (a nuclease), UvrD (a helicase II) and RecA (a recombinase). These mutants would typically be used in conjunction with a crosslinking compound, such as a psoralen. In one embodiment, there are attenuating mutations, such as deletions, in both uvrA and uvrB (uvrAB). KBMA mutations are further described in Brockstedt et al, Nature Med. 11, 853-860 (2005) and in U.S. Published Patent Application No. 2004/0228877.

Additional mutations contemplated by the inventors include those detailed in U.S. Pat. Nos. 8,926,993, 8,580,939, 8,287,883, 7,927,606 and 7,842,289, the contents of all being incorporated herein by reference.

In certain embodiments, mutant bacteria according to the subject invention express at least one heterologous product—e.g. a protein, peptide, polypeptide, glycoprotein, lipoprotein, or other macromolecule.

According to one embodiment, the product is a mammalian product, e.g. a human product.

According to another embodiment, the product is a bacterial product.

The nature of the heterologous product/products depends on the use of the mutant Listeria bacteria, e.g., to study Listeria species, to produce Listeria species vaccines, for cytosolic delivery of macromolecules, etc. For example, where the bacteria are employed in the production of Listeria vaccines, the product may be a heterologous antigen, where representative heterologous antigens of interest include, but are not limited to: (a) viral antigens, e.g., influenza np protein, HIV gag protein, HIV env protein or parts thereof, e.g., gp120 and gp41, HIV nef protein, HIV pol proteins, HIV reverse transcriptase, HIV protease, herpes virus proteins, etc., (b) to malarial antigens; (c) fungal antigens; (d) bacterial antigens; (e) tumor and tumor related antigens; and the like.

Heterologous antigens therefore include those specified by infectious agents, wherein an immune response directed against the antigen serves to prevent or treat disease caused by the agent. Such heterologous antigens include, but are not limited to, viral, bacterial, fungal or parasite surface proteins and any other proteins, glycoproteins, lipoprotein, glycolipids, and the like. Heterologous antigens also include those which provide benefit to a host organism which is at risk for acquiring or which is diagnosed as having a tumor that expresses the heterologous antigen(s). The host organism is preferably a mammal and most preferably, is a human.

The term "heterologous antigen," refers to a protein or peptide, a lipoprotein or lipopeptide, or any other macromolecule which is not normally expressed in Listeria, which substantially corresponds to the same antigen in an infectious agent, a tumor cell or a tumor-related protein. The heterologous antigen is expressed by a strain of Listeria according to the subject invention, and is processed and presented to cytotoxic T-cells upon infection of mammalian cells by the strain. The heterologous antigen expressed by Listeria species need not precisely match the corresponding unmodified antigen or protein in the tumor cell or infectious agent so long as it results in a T-cell response that recognizes the unmodified antigen or protein which is naturally expressed in the mammal. In other examples, the tumor cell antigen may be a mutant form of that which is naturally expressed in the mammal, and the antigen expressed by the Listeria species will conform to that tumor cell mutated antigen. By the term "tumor-related antigen," as used herein, is meant an antigen which affects tumor growth or metastasis in a host organism. The tumor-related antigen may be an antigen expressed by a tumor cell, or it may be an antigen which is expressed by a non-tumor cell, but which when so expressed, promotes the growth or metastasis of tumor cells. The types of tumor antigens and tumor-related antigens, which may be introduced into Listeria by way of incorporating DNA encoding the same, include any known or heretofore unknown tumor antigen. In other examples, the "'NM tumor-related antigen" has no effect on tumor growth or metastasis, but is used as a component of the Listeria vaccine because it is expressed specifically in the tissue (and tumor) from which the tumor is derived. In still other examples, the "tumor-related antigen" has no effect on tumor growth or metastasis, but is used as a component of the Listeria vaccine because to it is selectively expressed in the tumor cell and not in any other normal tissues. The heterologous antigen useful in vaccine development may be selected using knowledge available to the skilled artisan, and many antigenic proteins which are expressed by tumor cells or which affect tumor growth or metastasis or which are expressed by infectious agents are currently known. For example, viral antigens which may be considered as useful as heterologous antigens include but are not limited to the nucleoprotein (NP) of influenza virus and the gag protein of HIV. Other heterologous antigens include, but are not limited to, HFV env protein or its component parts gp120 and gp41, HIV nef protein, and the HIV pol proteins, reverse transcriptase and protease. Still other heterologous antigens can be those related to hepatitis C virus (HCV), including but not limited to the E1 and E2 glycoproteins, as well as non-structural (NS) proteins, for example NS3. In addition, other viral antigens such as herpes virus proteins may be useful. The heterologous antigens need not be limited to being of viral origin. Parasitic antigens, such as, for example, malarial antigens, are included, as are fungal antigens, bacterial antigens and tumor antigens.

As noted herein, a number of proteins expressed by tumor cells are also known and are of interest as heterologous antigens which may be inserted into the vaccine strain of the invention. These include, but are not limited to, the bcr/abl antigen in leukemia, HPVE6 and E7 antigens of the oncogenic virus associated with cervical cancer, the MAGE1 and MZ2-E antigens in or associated with melanoma, and the MVC-I and HER-2 antigens in or associated with breast cancer. Other coding sequences of interest include, but are not limited to, costimulatory molecules, immunoregulatory molecules, and the like.

Where the subject vectors are employed in the preparation of Listeria delivery vehicles, e.g., as described in PCT publication no. WO 00/09733 (the priority application of which is herein incorporated by reference); and Dietrich et al., Nature Biotechnology (1998) 16: 181-185, the heterologous polypeptide coding sequence may be a cytolysin, e.g., phospholipase, pore forming toxin, listeriolysin O, streptolysin O, perfringolysin O, acid activated cytolysins, phage lysins, etc. Other coding sequences of interest include, but are not limited to: cytokines, costimulatory molecules, and the like. As indicated above, the mutant bacteria of this invention may express two or more heterologous products, where the products act concurrently to provide a desired result.

Exemplary heterologous antigens contemplated by the present invention are presented herein below:

Mesothelin GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). Wilms' tumor-1 WT-1 isoform A (GenBank Acc. Nos. NM_000378; NP_000369). associated protein WT-1 isoform B (GenBank Acc. Nos. NM_024424; NP_077742). (Wt-1), including WT-1 isoform C (GenBank Acc. Nos. NM_024425; NP_077743). isoform A; isoform B; WT-1 isoform D (GenBank Acc. Nos. NM_024426; NP_077744). isoform C; isoform D. Stratum corneum GenBank Acc. No. NM_005046; NM_139277; AF332583. See also, chymotryptic enzyme e.g., Bondurant, et al. (2005) Clin. Cancer Res. 11: 3446-3454; Santin, (SCCE), and variants et al. (2004) Gynecol. Oncol. 94: 283-288; Shigemasa, et al. (2001) thereof. Int. J. Gynecol. Cancer 11: 454-461; Sepehr, et al. (2001) Oncogene 20: 7368-7374. MHC class I See, e.g., Groh, et al. (2005) Proc. Natl. Acad. Sci. USA 102: 6461-6466; chain-related protein A GenBank Acc. Nos. NM_000247; BC_016929; AY750850; (MICA); MHC class I NM_005931. chain-related protein A (MICB). Gastrin and peptides Harris, et al. (2004) Cancer Res. 64: 5624-5631; Gilliam, et al. (2004) derived from gastrin; Eur. J. Surg. Oncol. 30: 536-543; Laheru and Jaffee (2005) Nature gastrin/CCK-2 receptor Reviews Cancer 5: 459-467. (also known as CCK-B). Glypican-3 (an antigen GenBank Acc. No. NM_004484. Nakatsura, et al. (2003) Biochem. of, e.g., hepatocellular Biophys. Res. Commun 306: 16-25; Capurro, et al. (2003) carcinoma and Gasteroenterol. 125: 89-97; Nakatsura, et al. (2004) Clin. Cancer Res. melanoma). 10: 6612-6621). Coactosin-like protein. Nakatsura, et al. (2002) Eur. J. Immunol. 32: 826-836; Laheru and Jaffee (2005) Nature Reviews Cancer 5: 459-467. Prostate stem cell GenBank Acc. No. AF043498; AR026974; AR302232 (see also, e.g., antigen (PSCA). Argani, et al. (2001) Cancer Res. 61: 4320-4324; Christiansen, et al. (2003) Prostate 55: 9-19; Fuessel, et al. (2003) 23: 221-228). Prostate acid Small, et al. (2000) J. Clin. Oncol. 18: 3894-3903; Altwein and phosphatase (PAP); Luboldt (1999) Urol. Int. 63: 62-71; Chan, et al. (1999) Prostate 41: 99-109; prostate-specific Ito, et al. (2005) Cancer 103: 242-250; Schmittgen, et al. (2003) antigen (PSA); PSM; Int. J. Cancer 107: 323-329; Millon, et al. (1999) Eur. to Urol. 36: 278-285. PSMA. Six-transmembrane See, e.g., Machlenkin, et al. (2005) Cancer Res. 65: 6435-6442; epithelial antigen of GenBank Acc. No. NM_018234; NM_001008410; NM_182915; prostate (STEAP). NM_024636; NM_012449; BC011802. Prostate carcinoma See, e.g., Machlenkin, et al. (2005) Cancer Res. 65: 6435-6442; tumor antigen-1 GenBank Acc. No. L78132. (PCTA-1). Prostate See, e.g., Machlenkin, et al. (2005) Cancer Res. 65: 6435-6442). tumor-inducing gene-1 (PTI-1). Prostate-specific gene See, e.g., Machlenkin, et al. (2005) Cancer Res. 65: 6435-6442). with homology to G protein-coupled receptor. Prostase (an antrogen See, e.g., Machlenkin, et al. (2005) Cancer Res. 65: 6435-6442; regulated serine GenBank Acc. No. BC096178; BC096176; BC096175. protease). Proteinase 3. GenBank Acc. No. X55668. Cancer-testis antigens, GenBank Acc. No. NM_001327 (NY-ESO-1) (see also, e.g., Li, et al. e.g., NY-ESO-1; SCP—(2005) Clin. Cancer Res. 11: 1809-1814; Chen, et al. (2004) Proc. 1; SSX-1; SSX-2; SSX—Natl. Acad. Sci. USA. 101(25): 9363-9368; Kubuschok, et al. (2004) 4; GAGE, CT7; CTB; Int. J. Cancer. 109: 568-575; Scanlan, et al. (2004) Cancer Immun. CT10; MAGE-1; 4: 1; Scanlan, et al. (2002) Cancer Res. 62: 4041-4047; Scanlan, et al. MAGE-2; MAGE-3; (2000) Cancer Lett. 150: 155-164; Dalerba, et al. (2001) Int. J. Cancer MAGE-4; MAGE-6; 93: 85-90; Ries, et al. (2005) Int. J. Oncol. 26: 817-824. LAGE-1. MAGE-A1, Otte, et al. (2001) Cancer Res. 61: 6682-6687; Lee, et al. (2003) Proc. MAGE-A2; Natl. Acad. Sci. USA 100: 2651-2656; Sarcevic, et al. (2003) MAGE-A3; Oncology 64: 443-449; Lin, et al. (2004) Clin. Cancer Res. 10: 5708-5716. MAGE-A4; MAGE-A6; MAGE-A9; MAGE-A10; MAGE-A12; GAGE-3/6; NT-SAR-35; BAGE; CA125. GAGE-1; GAGE-2; De Backer, et al. (1999) Cancer Res. 59: 3157-3165; Scarcella, et al. GAGE-3; GAGE-4; (1999) Clin. Cancer Res. 5: 335-341. GAGE-5; GAGE-6; GAGE-7; GAGE-8; GAGE-65; GAGE-11; GAGE-13; GAGE-7B. HIP1R; LMNA; Scanlan, et al. (2002) Cancer Res. 62: 4041-4047. KIAA1416; Seb4D; KNSL6; TRIP4; MBD2; HCAC5; MAGEA3. DAM family of genes, Fleishhauer, et al. (1998) Cancer Res. 58: 2969-2972. e.g., DAM-1; DAM-6. RCAS1. Enjoji, et al. (2004) Dig. Dis. Sci. 49: 1654-1656. RU2. Van Den Eynde, et al. (1999) J. Exp. Med. 190: 1793-1800. CAMEL. Slager, et al. (2004) J. Immunol. 172: 5095-5102; Slager, et al. (2004) Cancer Gene Ther. 11: 227-236. Colon cancer associated Scanlan, et al. (2002) Cancer Res. 62: 4041-4047. antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. N-Acetylglucosaminyl-Dosaka-Akita, et al. (2004) Clin. Cancer Res. 10: 1773-1779. tranferase V (GnT-V). Elongation factor 2 Renkvist, et al. (2001) Cancer Immunol Immunother. 50: 3-15. mutated (ELF2M). HOM-MEL-40/SSX2 Neumann, et al. (2004) Int. J. Cancer 112: 661-668; Scanlan, et al. (2000) Cancer Lett. 150: 155-164. BRDT. Scanlan, et al. (2000) Cancer Lett. 150: 155-164. SAGE; HAGE. Sasaki, et al. (2003) Eur. J. Surg. Oncol. 29: 900-903. RAGE. See, e.g., Li, et al. (2004) Am. J. Pathol. 164: 1389-1397; Shirasawa, et al. (2004) Genes to Cells 9: 165-174. MUM-1 (melanoma Gueguen, et al. (1998) J. Immunol. 160: 6188-6194; Hirose, et al. ubiquitous mutated); (2005) Int. J. Hematol. 81: 48-57; Baurain, et al. (2000) J. Immunol. MUM-2; MUM-2 Arg-164: 6057-6066; Chiari, et al. (1999) Cancer Res. 59: 5785-5792. Gly mutation; MUM-3. LDLR/FUT fusion Wang, et al. (1999) J. Exp. Med. 189: 1659-1667. protein antigen of melanoma. NY-REN series of renal Scanlan, et al. (2002) Cancer Res. 62: 4041-4047; Scanlan, et al. cancer antigens. (1999) Cancer Res. 83: 456-464. NY-BR series of breast Scanlan, et al. (2002) Cancer Res. 62: 4041-4047; Scanlan, et al. cancer antigens, e.g., (2001) Cancer Immunity 1: 4. NY-BR-62; NY-BR-75; NY-BR-85; NY-BR-62; NY-BR-85. BRCA-1; BRCA-2. Stolier, et al. (2004) Breast J. 10: 475-480; Nicoletto, et al. (2001) Cancer Treat Rev. 27: 295-304. DEK/CAN fusion Von Lindern, et al. (1992) Mol. Cell. Biol. 12: 1687-1697. protein. Ras, e.g., wild type ras, GenBank Acc. Nos. P01112; P01116; M54969; M54968; P01111; ras with mutations at P01112; K00654. See also, e.g., GenBank Acc. Nos. M26261; codon 12, 13, 59, or 61, M34904; K01519; K01520; BC006499; NM_006270; NM_002890; e.g., mutations G12C; NM_004985; NM_033360; NM_176795; NM_005343. G12D; G12R; G12S; G12V; G13D; A59T; Q61H. K-RAS; H-RAS; N-RAS. BRAF (an isoform of Tannapfel, et al. (2005) Am. J. Clin. Pathol. 123: 256-2601; Tsao and RAF). Sober (2005) Dermatol. Clin. 23: 323-333. Melanoma antigens, GenBank Acc. No. NM_206956; NM_206955; NM_206954; including HST-2 NM_206953; NM_006115; NM_005367; NM_004988; AY148486; melanoma cell U10340; U10339; M77481. See, eg., Suzuki, et al. (1999) J. antigens. Immunol. 163: 2783-2791. Survivin GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). MDM-2 NM_002392; NM_006878 (see also, e.g., Mayo, et al. (1997) Cancer Res. 57: 5013-5016; Demidenko and Blagosklonny (2004) Cancer Res. 64: 3653-3660). Methyl-CpG-binding Muller, et al. (2003) Br. J. Cancer 89: 1934-1939; Fang, et al. (2004) proteins (MeCP2; World J. Gastreenterol. 10: 3394-3398. MBD2). NA88-A. Moreau-Aubry, et al. (2000) J. Exp. Med. 191: 1617-1624. Histone deacetylases Waltregny, et al. (2004) Eur. J. Histochem. 48: 273-290; Scanlan, et (HDAC), e.g., HDAC5. al. (2002) Cancer Res. 62: 4041-4047. Cyclophilin B (Cyp-B). Tamura, et al. (2001) Jpn. J. Cancer Res. 92: 762-767. CA 15-3; CA 27.29. Clinton, et al. (2003) Biomed. Sci. Instrum.

39: 408-414. Heat shock protein Hsp70. GAGE/PAGE family, e.g., PAGE-1; PAGE-2; PAGE-3; PAGE-4; XAGE-1; XAGE-2; XAGE-3. MAGE-A, B, C, and D families. MAGE-B5; MAGE-B6; MAGE-C2; MAGE-C3; MAGE-3; MAGE-6. Kinesin 2; TATA element modulatory factor 1; tumor protein D53; NY Alpha-fetoprotein (AFP) SART1; SART2; SART3; ART4. Preferentially expressed antigen of melanoma (PRAME). Carcinoembryonic antigen (CEA), e.g., CAP1-6D enhancer agonist peptide. HER-2/neu. Cdk4; cdk6; p16 (INK4); Rb protein. TEL; AML1; TEL/AML1. Telomerase (TERT). 707-AP. Annexin, e.g., Annexin II. BCR/ABL; BCR/ABL p210; BCR/ABL p190; CML-66; CML-28. BCL2; BLC6; CD10 protein. CDC27 (this is a melanoma antigen). Sperm protein 17 (SP17); 14-3-3-zeta; MEMD; KIAA0471; TC21. Tyrosinase-related proteins 1 and 2 (TRP-1 and TRP-2). Gp100/pmel-17. TARP. Tyrosinase-related proteins 1 and 2 (TRP-1 and TRP-2). Melanocortin 1 receptor (MC1R); MAGE-3; gp100; tyrosinase; dopachrome tautomerase (TRP-2); MART-1. MUC-1; MUC-2. Spas-1. U.S. Published Pat. Appl. No. 20020150588 of Allison, et al. CASP-8; FLICE; MACH. CEACAM6; CAP-1. HMGB1 (a DNA Faure, et al. (2004) Int. J. Cancer 108: 863-870. Brinkmann, et al. (1999) Cancer Res. 59: 1445-1448. Lucas, et al. (2000) Int. J. Cancer 87: 55-60; Scanlan, et al. (2001) Cancer Immun. 1: 4. Scanlan, et al. (2001) Cancer Immun 30: 1-4. Grimm, et al. (2000) Gastroenterol. 119: 1104-1112. Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. Matsushita, et al. (2003) Leuk. Lymphoma 44: 439-444; Oberthuer, et al. (2004) Clin. Cancer Res. 10: 4307-4313. GenBank Acc. No. M29540; E03352; X98311; M17303 (see also, Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). Disis, et al. (2004) J. Clin. Immunol. 24: 571-578; Disis and Cheever (1997) Adv. Cancer Res. 71: 343-371. Ghazizadeh, et al. (2005) Respiration 72: 68-73; Ericson, et al. (2003) Mol. Cancer Res. 1: 654-664. Stams, et al. (2005) Clin. Cancer Res. 11: 2974-2980. Nair, et al. (2000) Nat. Med. 6: 1011-1017. Takahashi, et al. (1997) Clin. Cancer Res. 3: 1363-1370. Zimmerman, et al. (2004) Virchows Arch. 445: 368-374. Cobaldda, et al. (2000) Blood 95: 1007-1013; Hakansson, et al. (2004) Leukemia 18: 538-547; Schwartz, et al. (2003) Semin Hematol. 40: 87-96; Lim, et al. (1999) Int. J. Mol. Med. 4: 665-667. Iqbal, et al. (2004) Am. J. Pathol. 165: 159-166. Wang, et al. (1999) Science 284: 1351-1354. Arora, et al. (2005) Mol. Carcinog. 42: 97-108. GenBank Acc. No. NM_001922. (see also, e.g., Bronte, et al. (2000) Cancer Res. 60: 253-258). GenBank Acc. Nos. AH003567; U31798; U31799; U31807; U31799 (see also, e.g., Bronte, et al. (2000) Cancer Res. 60: 253-258). See, e.g., Clifton, et al. (2004) Proc. Natl. Acad. Sci. USA 101: 10166-10171; Virok, et al. (2005) Infection Immunity 73: 1939-1946. GenBank Acc. No. NM_001922. (see also, e.g., Bronte, et al. (2000) Cancer Res. 60: 253-258). Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. See, e.g., Davies, et al. (1994) Cancer Lett. 82: 179-184; Gambus, et al. (1995) Int. J. Cancer 60: 146-148; McCool, et al. (1999) Biochem. J. 341: 593-600. Mandruzzato, et al. (1997) J. Exp. Med. 186: 785-793. Duxbury, et al. (2004) Biochem. Biophys. Res. Commun 317: 837-843; Morse, et al. (1999) Clin. Cancer Res. 5: 1331-1338. Brezniceanu, et al. (2003) FASEB J. 17: 1295-1297. binding protein and cytokine). ETV6/AML1. Codrington, et al. (2000) Br. J. Haematol. 111: 1071-1079. Mutant and wild type forms of adenomatous polyposis coli (APC); beta-catenin; c-met; p53; E-cadherin; cyclooxygenase-2 (COX-2). Renal cell carcinoma antigen bound by mAB G250. EphA2 See, e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 (chicken). *Francisella tularensis* antigens *Francisella tularensis* Complete genome of subspecies Schu S4 (GenBank Acc. No. A and B. of subspecies Schu 4 (GenBank Acc. No. NC_006570). Outer membrane protein (43 kDa). Antigenic components of *F. tularensis* include, e.g., 80 antigens, including 10 kDa and 60 kDa chaperonins, nucleoside diphosphate kinase, isocitrate dehydrogenase, RNA-binding protein Hfq, the chaperone ClpB. Malarial antigens Circumsporozoite protein (CSP); SSP2; HEP17; Exp-1 orthologs found in 96: 221-227. CSP (see, e.g., GenBank Acc. No. AB121024). SSP2 *P. falciparum*; and (see, e.g., GenBank Acc. No. AF249739). LSA-1 See, e.g., GenBank LSA-1. Acc. No. Z30319). Ring-infected erythrocyte survace protein (RESA); merozoite surface protein 2 (MSP2); MSP1; RESA (see, Spf66; merozoite surface protein 1 (MSP1); 195A; BVp42. Apical membrane antigen 1 (AMA1). AMA1 (see, e.g., GenBank Acc. No. A'13; AJ494905; AJ490565). Viruses and viral antigens Hepatitis A GenBank Acc. Nos., e.g., NC_001489; AY644670; X83302; K02990; M14707. Hepatitis B Complete genome (see, e.g., GenBank Acc. Nos. AB214516; NC_003977; AB205192; AB205191; AB205190; AJ748098; AB198079; AB198078; AB198076; AB074756). Hepatitis C Complete genome (see, e.g., GenBank Acc. Nos. NC_004102; AJ238800; AJ238799; AJ132997; AJ132996; AJ000009; D84263). Hepatitis D GenBank Acc. Nos, e.g. NC_001653; AB118847; AY261457. Human papillomavirus, See, e.g., Trimble, et Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. Mulders, et al. (2003) Urol. Clin. North Am. 30: 455-465; Steffens, et al. (1999) Anticancer Res. 19: 1197-1200. Bevanger, et al. (1988) J. Clin. Microbiol. 27: 922-926; Porsch-Ozcurumez, et al. (2004) Clin. Diagnostic. Lab. Immunol. 11: 1008-1015). (Havlasova, et al. (2002) Proteomics 2: 857-86), (Havlasova, et al. (2005) Proteomics 5: 2090-2103). See also, e.g., Oyston and Quarry (2005) Antonie Van Leeuwenhoek 87: 277-281; Isherwood, et al. (2005) Adv. Drug Deliv. Rev. 57: 1403-1414; Biagini, et al. (2005) Anal. Bioanal. Chem. 382: 1027-1034. See, e.g., Haddad, et al. (2004) Infection Immunity 72: 1594-1602; Hoffman, et al. (1997) Vaccine 15: 842-845; Oliveira-Ferreira and Daniel-Ribeiro (2001) Mem. Inst. Oswaldo Cruz, Rio de Janeiro Stirnadel, et al. (2000) Int. J. Epidemiol. 29: 579-586; Krzych, et al. (1995) J. Immunol. 155: 4072-4077. See also, Good, et al. (2004) Immunol. Rev. 201: 254-267; Good, et al. (2004) Ann. Rev. Immunol. 23: 69-99. (see, e.g., GenBank Acc. No. X96399; X96397). MSP1 (see, e.g., GenBank Acc. No. X03371). (see, e.g., GenBank Acc. No. X05181; X05182). See, e.g., Gupta, et al. (2005) Protein Expr. Purif. 41: 186-198.

(2003) Vaccine 21: 4036-4042; Kim, et al. including all 200+(2004) Gene Ther. 11: 1011-1018; Simon, et al. (2003) Eur. J. Obstet. subtypes (classed in Gynecol. Reprod. Biol. 109: 219-223; Jung, et al. (2004) J. Microbiol. 16 groups), such as the 42: 255-266; Damasus-Awatai and Freeman-Wang (2003) Curr. Opin. high risk subtypes 16, Obstet. Gynecol. 15: 473-477; Jansen and Shaw (2004) Annu. Rev. 18, 30, 31, 33, 45. Med. 55: 319-331; Roden and Wu (2003) Expert Rev. Vaccines 2: 495-516; de Villiers, et al. (2004) Virology 324: 17-24; Hussain and Paterson (2005) Cancer Immunol. Immunother. 54: 577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). Human T-cell See, e.g., Capdepont, et al. (2005) AIDS Res. Hum. Retrovirus 21: 28-42; lymphotropic virus Bhigjee, et al. (1999) AIDS Res. Hum. Restrovirus 15: 1229-1233; (HTLV) types I and II, Vandamme, et al. (1998) J. Virol. 72: 4327-4340; Vallejo, et al. (1996) including the J. Acquir. Immune Defic. Syndr. Hum. Retrovirol. 13: 384-391. HTLV type I subtypes HTLV type I (see, e.g., GenBank Acc. Nos. AY563954; AY563953. Cosmopolitan, Central HTLV type II (see, e.g., GenBank Acc. Nos. L03561; Y13051; African, and AF139382). Austro-Melanesian, and the HTLV type II subtypes ha, Iib, Iic, and Iid. Coronaviridae, See, e.g., Brian and Baric (2005) Curr. Top. Microbiol. Immunol. including 287: 1-30; Gonzalez, et al. (2003) Arch. Virol. 148: 2207-2235; Smits, Coronaviruses, such as et al. (2003) J. Virol. 77: 9567-9577; Jamieson, et al. (1998) J. Infect. SARS-coronavirus Dis. 178: 1263-1269 (GenBank Acc. Nos. AY348314; NC_004718; (SARS-CoV), and AY394850). Toroviruses. Rubella virus. GenBank Acc. Nos. NC_001545; AF435866. Mumps virus, including See, e.g., Orvell, et al. (2002) J. Gen. Virol. 83: 2489-2496. See, e.g., the genotypes A, C, D, GenBank Acc. Nos. AY681495; NC_002200; AY685921; AF201473. G, H, and I. Coxsackie virus A See, e.g., Brown, et al. (2003) J. Virol. 77: 8973-8984. GenBank Acc. including the serotypes Nos. AY421768; AY790926: X67706. 1, 11, 13, 15, 17, 18, 19, 20, 21, 22, and 24 (also known as Human enterovirus C; HEV-C). Coxsackie virus B, See, e.g., Ahn, et al. (2005) J. Med. Virol. 75: 290-294; Patel, et al. including subtypes 1-6. (2004) J. Virol. Methods 120: 167-172; Rezig, et al. (2004) J. Med. Virol. 72: 268-274. GenBank Acc. No. X05690. Human enteroviruses See, e.g., Oberste, et al. (2004) J. Virol. 78: 855-867. Human including, e.g., human enterovirus A (GenBank Acc. Nos. NC_001612); human enterovirus A (HEV-A, enterovirus B (NC_001472); human enterovirus C (NC_001428); CAV2 to CAVE, human enterovirus D (NC_001430). Simian enterovirus A (GenBank CAV10, CAV12, Acc. No. NC_003988). CAV14, CAV16, and EV71) and also including HEV-B (CAV9, CBV1 to CBV6, E1 to E7, E9, E11 to E21, E24 to E27, E29 to E33, and EV69 and E73), as well as HEV. Polioviruses including See, e.g., He, et al. (2003) J. Virol. 77: 4827-4835; Hahsido, et al. PV1, PV2, and PV3. (1999) Microbiol. Immunol. 43: 73-77. GenBank Acc. No. AJ132961 (type 1); AY278550 (type 2); X04468 (type 3). Viral encephalitides See, e.g., Hoke (2005) Mil. Med. 170: 92-105; Estrada-Franco, et al. viruses, including (2004) Emerg. Infect. Dis. 10: 2113-2121; Das, et al. (2004) Antiviral equine encephalitis, Res. 64: 85-92; Aguilar, et al. (2004) Emerg. Infect. Dis. 10: 880-888; Venezuelan equine Weaver, et al. (2004) Arch. Virol. Suppl. 18: 43-64; Weaver, et al. encephalitis (VEE) (2004) Annu. Rev. Entomol. 49: 141-174. Eastern equine encephalitis (including subtypes IA, (GenBank Acc. No. NC_003899; AY722102); Western equine IB, IC, ID, IIIC, IIID), encephalitis (NC_003908). Eastern equine encephalitis (EEE), Western equine encephalitis (WEE), St. Louis encephalitis, Murray Valley (Australian) encephalitis, Japanese encephalitis, and tick-born encephalitis. Human herpesviruses, See, e.g., Studahl, et al. (2000) Scand. J. Infect. Dis. 32: 237-248; including Padilla, et al. (2003) J. Med. Virol. 70 (Suppl. 1) S103-S110; cytomegalovirus Jainkittivong and Langlais (1998) Oral Surg. Oral Med. 85: 399-403. (CMV), Epstein-Barr GenBank Nos. NC_001806 (herpesvirus 1); NC_001798 virus (EBV), human (herpesvirus 2); X04370 and NC_001348 (herpesvirus 3); herpesvirus-1 (HHV-1), NC_001345 (herpesvirus 4); NC_001347 (herpesvirus 5); X83413 HHV-2, HHV-3, and NC_000898 (herpesvirus 6); NC_001716 (herpesvirus 7). HHV-4, HHV-5, Human herpesviruses types 6 and 7 (HHV-6; HHV-7) are disclosed HHV-6, HHV-7, by, e.g., Padilla, et al. (2003) J. Med. Virol. 70 (Suppl. 1) S103-S110. HHV-8, herpes B virus, Human herpesvirus 8 (HHV-8), including subtypes A-E, are disclosed herpes simplex virus in, e.g., Treumicht, et al. (2002) J. Med. Virol. 66: 235-240. types 1 and 2 (HSV-1, HSV-2), and varicella zoster virus (VZV). HIV-1 including group See, e.g., Smith, et al. (1998) J. Med. Virol. 56: 264-268. See also, M (including subtypes e.g., GenBank Acc. Nos. DQ054367; NC_001802; AY968312; A to J) and group 0 DQ011180; DQ011179; DQ011178; DQ011177; AY588971; (including any AY588970; AY781127; AY781126; AY970950; AY970949; distinguishable AY970948; X61240; AJ006287; AJ508597; and AJ508596. subtypes) (HIV-2, including subtypes A-E. Epstein-Ban virus See, e.g., Peh, et al. (2002) Pathology 34: 446-450. (EBV), including Epstein-Barr virus strain B95-8 (GenBank Acc. No. V01555). subtypes A and B. Reovirus, including See, e.g., Barthold, et al. (1993) Lab. Anim Sci. 43: 425-430; Roner, serotypes and strains 1, et al. (1995) Proc. Natl. Acad. Sci. USA 92: 12362-12366; Kedl, et al. 2, and 3, type 1 Lang, (1995) J. Virol. 69: 552-559. GenBank Acc. No. K02739 (sigma-3 type 2 Jones, and type 3 gene surface protein). Dearing. Cytomegalovirus See, e.g., Chern, et al. (1998) J. Infect. Dis. 178: 1149-1153; Vilas (CMV) subtypes Boas, et al. (2003) J. Med. Virol. 71: 404-407; Trincado, et al. (2000) include CMV subtypes J. Med. Virol. 61: 481-487. GenBank Acc. No. X17403. I-VII. Rhinovirus, including Human rhinovirus 2 (GenBank Acc. No. X02316); Human all serotypes. rhinovirus B (GenBank Acc. No. NC_001490); Human rhinovirus 89 (GenBank Acc. No. NC_001617); Human rhinovirus 39 (GenBank Acc. No. AY751783). Adenovirus, including AY803294; NC_004001; AC_000019; AC_000018; AC_000017; all serotypes. AC_000015; AC_000008; AC000007; AC000006; AC_000005; AY737798; AY737797; NC_003266; NC_002067; AY594256; AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. Varicella-zoster virus, See, e.g., Loparev, et al. (2004) J. Virol. 78: 8349-8358; Carr, et al. including strains and (2004) J. Med. Virol. 73: 131-136; Takayama and Takayama (2004) J. genotypes Oka, Dumas, Clin. Virol. 29: 113-119. European, Japanese, and Mosaic. Filoviruses, including See, e.g., Geisbert and Jahrling (1995) Virus Res. 39: 129-150; Marburg virus and Hutchinson, et al. (2001) J. Med. Virol. 65: 561-566. Marburg virus Ebola virus, and strains (see, e.g., GenBank Acc. No. NC_001608). Ebola virus (see, e.g., such as Ebola-Sudan GenBank Acc. Nos. NC_006432; AY769362; NC_002549; (EBO-S), Ebola-Zaire AF272001; AF086833). (EBO-Z), and Ebola-Reston (EBO-R). Arenaviruses, including Junin virus, segment S (GenBank Acc. No. NC_005081); Junin virus, lymphocytic segment L (GenBank Acc. No. NC_005080). choriomeningitis (LCM) virus, Lassa virus, Junin virus, and Machupo virus. Rabies virus. See, e.g., GenBank Acc. Nos. NC_001542; AY956319; AY705373; AF499686; AB128149; AB085828; AB009663. Arboviruses, including Dengue virus type 1 (see, e.g., GenBank Acc. Nos. AB195673; West Nile virus, AY762084). Dengue virus type 2 (see, e.g., GenBank Acc. Nos. Dengue viruses 1 to 4, NC_001474; AY702040; AY702039; AY702037). Dengue virus type Colorado tick fever 3 (see, e.g., GenBank Acc. Nos. AY923865; AT858043). Dengue virus, Sindbis virus, virus type 4 (see, e.g., GenBank Acc. Nos. AY947539; AY947539; Togaviraidae, AF326573). Sindbis virus (see, e.g., GenBank Acc. Nos. Flaviviridae, NC_001547; AF429428; J02363; AF103728). West Nile virus (see, Bunyaviridae, e.g., GenBank Acc. Nos. NC_001563; AY603654). Reoviridae, Rhabdoviridae, Orthomyxoviridae, and the like. Poxvirus including Viriola virus (see, e.g., GenBank Acc. Nos. NC_001611; Y16780; orthopoxvirus (variola X72086; X69198). virus, monkeypox virus, vaccinia virus, cowpox virus), yatapoxvirus (tanapox virus, Yaba monkey tumor virus), parapoxvirus, and molluscipoxvirus. Yellow fever. See, e.g., GenBank Acc. No. NC_002031; AY640589; X03700. Hantaviruses, including See, e.g., Elgh, et al. (1997) J. Clin. Microbiol. 35: 1122-1130; serotypes Hantaan Sjolander, et al. (2002) Epidemiol. Infect. 128: 99-103; Zeier, et al. (HTN), Seoul (SEO), (2005) Virus Genes 30: 157-180. GenBank Acc. No. NC_005222 and Dobrava (DOB), Sin NC_005219 (Hantavirus). See also, e.g., GenBank Acc. Nos. Nombre (SN), Puumala NC_005218; NC_005222; NC_005219. (PUU), and Dobrava-like Saaremaa (SAAV). Flaviviruses, including See, e.g., Mukhopadhyay, et al. (2005) Nature Rev. Microbiol. 3: 13-22. Dengue virus, Japanese GenBank Acc. Nos NC_001474 and AY702040 (Dengue). encephalitis virus, West GenBank Acc. Nos. NC_001563 and AY603654. Nile virus, and yellow fever virus. Measles virus. See, e.g., GenBank Acc. Nos. AB040874 and AY486084. Human parainfluenza virus 2 (see, e.g., GenBank Acc. Nos. parainfluenzaviruses AB176531; NC003443). Human parainfluenza virus 3 (see, e.g., (HPV), including HPV GenBank Acc. No. NC_001796). types 1-56. Influenza virus, Influenza nucleocapsid (see, e.g., GenBank Acc. No. AY626145). including Influenza hemagglutinin (see, e.g., GenBank Acc. Nos. AY627885; virus types A, B, and C. AY555153). Influenza neuraminidase (see, e.g., GenBank Acc. Nos. AY555151; AY577316). Influenza matrix protein 2 (see, e.g., GenBank Acc. Nos. AY626144. (Influenza basic protein 1 (see, e.g., GenBank Acc. No. AY627897). Influenza polymerase acid protein (see, e.g., GenBank Acc. No. AY627896). Influenza nucleoprotein (see, e.g., GenBank Acc. No. AY627895). to Influenza A virus Hemagglutinin of H1N1 (GenBank Acc. No. S67220). Influenza A subtypes, e.g., swine virus matrix protein (GenBank Acc. No. AY700216). Influenza virus viruses (SIV): H1N1 A H5H1 nucleoprotein (GenBank Acc. No. AY646426). H1N1 influenza A and swine haemagglutinin (GenBank Acc. No. D00837). See also, GenBank influenza virus. Acc. Nos. BD006058; BD006055; BD006052. See also, e.g., Wentworth, et al. (1994) J. Virol. 68: 2051-2058; Wells, et al. (1991) J.A.M.A. 265: 478-481. Respiratory syncytial Respiratory syncytial virus (RSV) (see, e.g., GenBank Acc. Nos. virus (RSV), including AY353550; NC_001803; NC001781). subgroup A and subgroup B. Rotaviruses, including Human rotavirus C segment 8 (GenBank Acc. No. AJ549087); human rotaviruses A to Human rotavirus G9 strain outer capsid protein (see, e.g., GenBank E, bovine rotavirus, Acc. No. DQ056300); Human rotavirus B strain non-structural protein rhesus monkey 4 (see, e.g., GenBank Acc. No. AY548957); human rotavirus A strain rotavirus, and major inner capsid protein (see, e.g., GenBank Acc. No. AY601554). human-RVV reassortments. Polyomavirus, See, e.g., Engels, et al. (2004) J. Infect. Dis. 190: 2065-2069; Vilchez including simian and Butel (2004) Clin. Microbiol. Rev. 17: 495-508; Shivapurkar, et virus 40 (SV40), JC al. (2004) Cancer Res. 64: 3757-3760; Carbone, et al. (2003) virus (JCV) and BK Oncogene 2: 5173-5180; Barbanti-Brodano, et al. (2004) Virology virus (BKV). 318: 1-9) (SV40 complete genome in, e.g., GenBank Acc. Nos. NC_001669; AF168994; AY271817; AY271816; AY120890; AF345344; AF332562). Coltiviruses, including Attoui, et al. (1998) J. Gen. Virol. 79: 2481-2489. Segments of Eyach Colorado tick fever virus (see, e.g., GenBank Acc. Nos. AF282475; AF282472; virus, Eyach virus. AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). Caliciviruses, including Snow Mountain virus (see, e.g., GenBank Acc. No. AY134748). the genogroups Norwalk, Snow Mountain group (SMA), and Saaporo. Parvoviridae, including See, e.g., Brown (2004) Dev. Biol. (Basel) 118: 71-77; Alvarez-dependovirus, Lafuente, et al. (2005) Ann Rheum. Dis. 64: 780-782; Ziyaeyan, et al. parvovirus (including (2005) Jpn. J. Infect. Dis. 58: 95-97; Kaufman, et al. (2005) Virology parvovirus B19), and 332: 189-198. erythrovirus.

Other exemplary heterologous antigens are provided in U.S. Pat. No. 8,580,939, the contents of which are incorporated herein by reference.

The introduction of DNA encoding a heterologous product into a strain of *Listeria* may be accomplished, for example, by the creation of a recombinant *Listeria* in which DNA encoding the heterologous product is harbored on a vector, such as a plasmid for example, which plasmid is maintained and expressed in the *Listeria* species, and in whose product expression is under the control of prokaryotic promoter/regulatory sequences. Alternatively, DNA encoding the heterologous product may be stably integrated into the *Listeria* chromosome by employing, for example, transposon mutagenesis, homologous recombination, plasmid integration, or integrase mediated site-specific integration (as described in U.S. patent application Ser. No. 10/136,860 and US Patent Application No. 20150037369, the disclosure of both being incorporated herein by reference).

Several approaches may be employed to express the heterologous antigen in *Listeria* species as will be understood by one skilled in the art once armed with the present disclosure. In certain embodiments, genes encoding heterologous products are designed to either facilitate secretion of the heterologous product from the bacterium or to facilitate expression of the heterologous product on the *Listeria* cell surface.

In certain embodiments, a fusion protein which includes the desired heterologous product and a secreted or cell surface protein of *Listeria* is employed. *Listeria* proteins which are suitable components of such fusion proteins include, but are not limited to, ActA, listeriolysin 0 (LLO) and phosphatidylinositol-specific phospholipase (PI-PLC).

A fusion protein may be generated by ligating the genes which encode each of the components of the desired fusion protein, such that both genes are in frame with each other.

Thus, expression of the ligated genes results in a protein comprising both the heterologous product and the *Listeria* protein.

Expression of the ligated genes may be placed under the transcriptional control of a Listerial promoter/regulatory sequence such that expression of the gene is effected during growth and replication of the organism. Signal sequences for cell surface expression and/or secretion of the fused protein may also be added to genes encoding heterologous products in order to effect cell surface expression and/or secretion of the fused protein. When the heterologous product is used alone (i.e., in the absence of fused *Listeria* sequences), it may be advantageous to fuse thereto signal sequences for to cell surface expression and/or secretion of the heterologous product. The procedures for accomplishing this are well know in the art of bacteriology and molecular biology.

The DNA encoding the heterologous product which is expressed is in many embodiments, preceded by a suitable promoter to facilitate such expression. The appropriate promoter/regulator)' and signal sequences to be used will depend on the type of Listerial protein desired in the fusion protein and will be readily apparent to those skilled in the art of *Listeria* molecular biology. For example, suitable *L. monocytogenes* promoter/regulatory and/or signal sequences which may be used to direct expression of a fusion protein include, but are not limited to, sequences derived from the *Listeria* hly gene which encodes LLO, the *Listeria* p60 (iap) gene, and the *Listeria* actA gene which encodes a surface protein necessary for *L. monocytogenes* actin assembly. Other promoter sequences of interest include the plcA gene which encodes PI-PLC, the *Listeria* mpl gene, which encodes a metalloprotease, and the *Listeria* inlA gene which encodes internalin, a *Listeria* membrane protein. The heterologous regulatory elements such as promoters derived from phage and promoters or signal sequences derived from other bacterial species may be employed for the expression of a heterologous antigen by the *Listeria* species.

In certain embodiments, the mutant *Listeria* include a vector. The vector may include DNA encoding a heterologous antigen. Typically, the vector is a plasmid that is capable of replication in *Listeria*. The vector may encode a heterologous antigen, wherein expression of the antigen is under the control of eukaryotic promoter/regulatory sequences, e.g., is present in an expression cassette. Typical plasmids having suitable promoters that are of interest include, but are not limited to, pCMV-β comprising the immediate early promoter/enhancer region of human cytomegalovirus, and those which include the SV40 early promoter region or the mouse mammary tumor virus LTR promoter region. [0079] As such, in certain embodiments, the subject bacteria include at least one coding sequence for heterologous polypeptide/protein, as described above. In many embodiments, this coding sequence is part of an expression cassette, which provides for expression of the coding sequence in the *Listeria* cell for which the vector is designed. The term "expression cassette" as used herein refers to an expression module or expression construct made up of a recombinant DNA molecule containing at least one desired coding sequence and appropriate nucleic acid sequences necessary for the expression of the operably linked coding sequence in a particular host organism, i.e. the *Listeria* cell for which the vector is designed, such as the promoter/regulatory/signal sequences identified above, where the expression cassette may include coding sequences for one, two or more different polypeptides, or multiple copies of the same coding sequence, as desired.

According to a particular embodiment, the size of the coding sequence and/or expression cassette is between about 25-30 to about 6000 bp, e.g. from about 50 to about 2000 bp. As such, the size of the encoded product may vary greatly, and a broad spectrum of different products may be encoded by the expression cassettes present in the vectors of this embodiment.

Adjuvant Compositions:

The subject mutant bacterial strains also find use as immunopotentiating agents, i.e., as adjuvants. In such applications, the subject attenuated bacteria may be administered in conjunction with an immunogen, e.g., a tumor antigen, modified tumor cell, etc., according to methods known in the art where live bacterial strains are employed as adjuvants. See, e.g., Berd et al, Vaccine 2001 Mar. 21; 19(17-19):2565-70.

In some embodiments, the mutant bacterial strains are employed as adjuvants by chemically coupling to a sensitizing antigen. The sensitizing antigen can be any antigen of interest, where representative antigens of interest include, but are not limited to: viral agents, e.g., Herpes simplex virus; malaria parasite; bacteria, e.g., *staphylococcus aureus* bacteria, diphtheria toxoid, tetanus toxoid, shistosomula; tumor cells, e.g. $CAD_2$ mammary adenocarcinomia tumor cells, and hormones such as thyroxine $T_4$, triiodothyronine $T_3$, and Cortisol. The coupling of the sensitizing antigen to the immunopotentiating agent can be accomplished by means of various chemical agents having two reactive sites such as, for example, bisdiazobenzidine, glutaraldehyde, di-iodoacetate. and diisocyanates, e.g. m-xylenediisocyanate and toluene-2,4-diisocyanate. Use of *Listeria* spp. as adjuvants is further described in U.S. Pat. No. 4,816,253.

Vaccines:

The subject attenuated mutant bacteria also find use as vaccines. The vaccines of the present invention are administered to a vertebrate by contacting the vertebrate with a sublethal dose of an attenuated mutant *Listeria* vaccine, where contact typically includes administering the vaccine to the host. In many embodiments, the attenuated bacteria are provided in a pharmaceutically acceptable formulation. to Administration can be oral, parenteral, intranasal, intramuscular, intradermal, intraperitoneal, intravascular, subcutaneous, direct vaccination of lymph nodes, administration by catheter or any one or more of a variety of well-known administration routes. In farm animals, for example, the vaccine may be administered orally by incorporation of the vaccine in feed or liquid (such as water). It may be supplied as a lyophilized powder, as a frozen formulation or as a component of a capsule, or any other convenient, pharmaceutically acceptable formulation that preserves the antigenicity of the vaccine. Any one of a number of well known pharmaceutically acceptable diluents or excipients may be employed in the vaccines of the invention. Suitable diluents include, for example, sterile, distilled water, saline, phosphate buffered solution, and the like. The amount of the diluent may vary widely, as those skilled in the art will recognize. Suitable excipients are also well known to those skilled in the art and may be selected, for example, from A. Wade and PJ. Weller, eds., Handbook of Pharmaceutical Excipients (1994) The Pharmaceutical Press: London. The dosage administered may be dependent upon the age, health and weight of the patient, the type of patient, and the existence of concurrent treatment, if any. The vaccines can be employed in dosage forms such as capsules, liquid solutions, suspensions, or elixirs, for oral administration, or sterile liquid for formulations such as solutions or suspensions for parenteral, intranasal intramuscular, or intravascular use. In accordance with the invention, the vaccine may be employed, in combination with a pharmaceutically acceptable diluent, as a vaccine composition, useful in immunizing a patient against infection from a selected organism or virus or with respect to a tumor, etc Immunizing a patient means providing the patient with at least some degree of therapeutic or prophylactic immunity against selected pathogens, cancerous cells, etc.

The subject vaccines find use in methods for eliciting or boosting a cellular immune response, e.g., a helper T cell or a cytotoxic T-cell response to a selected agent, e.g., pathogenic organism, tumor, etc., in a vertebrate, where such methods include administering an effective amount of the *Listeria* vaccine. The subject vaccines find use in methods for eliciting in a vertebrate an innate immune response that augments the antigen-specific immune response. Furthermore, the vaccines of the present invention may be used for treatment post-exposure or post diagnosis. In to general, the use of vaccines for post-exposure treatment would be recognized by one skilled in the art, for example, in the treatment of rabies and tetanus. The same vaccine of the present invention may be used, for example, both for immunization and to boost immunity after exposure. Alternatively, a different vaccine of the present invention may be used for post-exposure treatment, for example, such as one that is specific for antigens expressed in later stages of exposure. As such, the subject vaccines prepared with the subject vectors find use as both prophylactic and therapeutic vaccines to induce immune responses that are specific for antigens that are relevant to various disease conditions.

According to a specific embodiment, the bacteria of the present invention may be used for enhancing an immune response in a mammal to an antigen (i.e. as a boost). According to this aspect the subject has been previously administered with a prime dose of a target antigen (e.g. tumor cell or inactivated tumor cell). According to a specific embodiment, the prime dose does not comprise *Listeria* bacteria. The bacteria of the present invention which is used in the boost encodes and expresses an immunologically active portion of the target antigen which was administered in the priming vaccine.

The priming vaccine may contain either the target antigen itself, for example, a protein with or without an adjuvant, a tumor cell lysate, an irradiated tumor cell, an antigen-presenting cell pulsed with peptides of the target antigen (e.g. a dendritic cell), or it may contain an agent that provides the target antigen. Suitable agents that provide a target antigen include recombinant vectors, for example, bacteria, viruses, and naked DNA. Recombinant vectors are prepared using standard techniques known in the art, and contain suitable control elements operably linked to the nucleotide sequence encoding the target antigen. See, for example, Plotkin, et al. (eds.) (2003) Vaccines, 4.sup.th ed., W.B. Saunders, Co., Phila., Pa.; Sikora, et al. (eds.) (1996) Tumor Immunology Cambridge University Press, Cambridge, UK; Hackett and Ham (eds.) Vaccine Adjuvants, Humana Press, Totowa, N.J.; Isaacson (eds.) (1992) Recombinant DNA Vaccines, Marcel Dekker, NY, N.Y.; Morse, et al. (eds.) (2004) Handbook of Cancer Vaccines, Humana Press, Totowa, N.J.), Liao, et al. (2005) Cancer Res. 65:9089-9098; Dean (2005) Expert Opin. Drug Deliv. 2:227-236; Arlen, et al. (2003) Expert Rev. Vaccines 2:483-493; Dela Cruz, et al. (2003) Vaccine 21:1317-1326; Johansen, et al. (2000) Eur. J. Pharm. Biopharm. 50:413-417; Excler (1998) Vaccine 16:1439-1443; Disis, et al. (1996) J. Immunol. 156:3151-3158). Peptide vaccines are described (see, e.g., McCabe, et al. (1995) Cancer Res. 55:1741-1747; Minev, et al. (1994) Cancer Res. 54:4155-4161; Snyder, et al. (2004) J. Virology 78:7052-7060. Virus-derived vectors include viruses, modified viruses, and viral particles (see, e.g., U.S. Pat. No. 8,926,993, incorporated herein by reference). The virus-derived vectors can be administered directly to a mammalian subject, or can be introduced ex vivo into an antigen presenting cell (APC), where the APC is then administered to the subject.

Viral vectors may be based on, e.g., Togaviruses, including alphaviruses and flaviviruses; alphaviruses, such as Sindbis virus, Sindbis strain SAAR86, Semliki Forest virus (SFV), Venezuelan equine encephalitis (VEE), Eastern equine encephalitis (EEE), Western equine encephalitis, Ross River virus, Sagiyami virus, O'Nyong-nyong virus, Highlands J virus. Flaviviruses, such as Yellow fever virus, Yellow fever strain 17D, Japanese encephalitis, St. Louis encephalitis, Tick-borne encephalitis, Dengue virus, West Nile virus, Kunjin virus (subtype of West Nile virus); arterivirus such as equine arteritis virus; and rubivirus such as rubella virus, herpesvirus, modified vaccinia Ankara (MVA); avipox viral vector; fowlpox vector; vaccinia virus vector; influenza virus vector; adenoviral vector, human papilloma virus vector; bovine papilloma virus vector, and so on. Viral vectors may be based on an orthopoxvirus such as variola virus (smallpox), vaccinia virus (vaccine for smallpox), Ankara (MVA), or Copenhagen strain, camelpox, monkeypox, or cowpox. Viral vectors may be based on an avipoxvirus virus, such as fowlpox virus or canarypox virus.

Adenoviral vectors and adeno-associated virus vectors (AAV) are available, where adenoviral vectors include adenovirus serotype 5 (adeno5; Ad5), adeno6, adeno11, and adeno35. Available are at least 51 human adenovirus serotypes, classified into six subgroups (subgroups A, B, C, D, E, and F). Adenovirus proteins useful, for example, in assessing immune response to an "empty" advenoviral vector, include hexon protein, such as hexon 3 protein, fiber protein, and penton base proteins, and human immune responses to adenoviral proteins have been described (see, e.g., Wu, et al. (2002) J. Virol. 76:12775-12782; Mascola (2006) Nature 441:161-162; Roberts, et al. (2006) Nature 441:239-243).

According to another specific embodiment, the prime dose comprises Adenovirus or Vaccinia virus.

The patient may be any human and non-human animal susceptible to infection with the selected organism. The subject vaccines will find particular use with vertebrates such as man, and with domestic animals. Domestic animals include domestic fowl, bovine, porcine, ovine, equine, caprine, Leporidate (such as rabbits), or other animal which may be held in captivity.

In general, the subject vaccines find use in vaccination applications as described U.S. Pat. Nos. 5,830,702 and 6,051,237, as well as PCT publication no WO 99/25376.

Methods:

The present invention also provides methods for down-regulating interferon-$\beta$ production in a subject, by administering to a subject an effective amount of the *Listeria* bacterium of the present invention.

As used herein "therapeutically effective amount" or "efficacious amount" means the amount of an organism or compound that, when administered to a mammal or other subject for treating a disease, is sufficient to effect such treatment for the disease. The "therapeutically effective amount" will vary depending on the organism or compound, the disease and its severity and the age, weight, etc., of the subject to be treated.

In some embodiments, subjects suitable for treatment with a method of the present invention include individuals having a cellular proliferative disease, such as a neoplastic disease (e.g., cancer). Cellular proliferative disease is characterized by the undesired propagation of cells, including, but not limited to, neoplastic disease conditions, e.g., cancer. Examples of cellular proliferative disease include, but not limited to, abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying, for example, rheumatoid arthritis, psoriasis, diabetic retinopathy, other ocular angiogenic diseases such as retinopathy of prematurity (retrolental fibroplastic), macular degeneration, corneal graft rejection, neurovascular glaucoma and Oster Webber syndrome, psoriasis, restenosis, fungal, parasitic and viral infections such cytomegaloviral infections. Subjects to be treated according to the methods of the invention include any individual having any of the above-mentioned disorders.

In other embodiments, subjects suitable for treatment with a method of the present invention include individuals who have been clinically diagnosed as infected with a hepatitis virus (e.g., HAV, HBV, HCV, delta, etc.), particularly HCV, are suitable for treatment with the methods of the instant invention. Individuals who are infected with HCV are identified as having HCV RNA in their blood, and/or having anti-HCV antibody in their serum. Such individuals include naive individuals (e.g., individuals not previously treated for HCV, particularly those who have not previously received IFN-α-based or ribavirin-based therapy) and individuals who have failed prior treatment for HCV.

In other embodiments, subjects suitable for treatment with a method of the present invention include individuals having multiple sclerosis. Multiple sclerosis refers to an autoimmune neurodegenerative disease, which is marked by inflammation within the central nervous system with lymphocyte attack against myelin produced by oligodendrocytes, plaque formation and demyelization with destruction of the myelin sheath of axons in the brain and spinal cord, leading to significant neurological disability over time. Typically, at onset an otherwise healthy person presents with the acute or sub acute onset of neurological symptomatology (attack) manifested by unilateral loss of vision, vertigo, ataxia, dyscoordination, gait difficulties, sensory impairment characterized by paresthesia, dysesthesia, sensory loss, urinary disturbances until incontinence, diplopia, dysarthria or various degrees of motor weakness until paralysis. The symptoms are usually painless, remain for several days to a few weeks, and then partially or completely resolve. After a period of remission, a second attack will occur. During this period after the first attack, the patient is defined to suffer from probable MS. Probable MS patients may remain undiagnosed for years. When the second attack occurs the diagnosis of clinically definite MS (CDMS) is made (Poser criteria 1983; C. M. Poser et al, Ann. Neurol. 1983; 13, 227).

The terms "subject" and "patient" refers to a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest. Exemplary mammals which may be treated include, canines; to felines; equines; bovines; ovines; rodentia, etc. and primates, particularly humans. Non-human animal models, particularly mammals, e.g. primate, murine, lagomorpha, etc. may be used for experimental investigations.

The present invention also provides methods for expressing a molecule of interest in a cell comprising infecting the cell with the *Listeria* bacterium of the present invention. The cell which is infected may be part of a cell culture (i.e. in vitro, or ex vivo) or may be comprised in an organism (i.e. in vivo). Examples of molecules of interest are provided herein above.

Combination Therapy:

For use in the subject methods, the subject mutant *Listeria* may be administered in combination with other pharmaceutically active agents, including other agents that treat the underlying condition or a symptom of the condition. In addition, the mutant *Listeria* may be used to provide an increase in the effectiveness of another chemical, such as a pharmaceutical, that is necessary to produce the desired biological effect.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type. Examples of other agents for use in combination therapy of neoplastic disease include, but are not limited to, thalidomide, marimastat, COL-3, BMS-275291, squalamine, 2-ME, SU6668, neovastat, Medi-522, EMD121974, CAI, celecoxib, interleukin-12, IM862, TNP470, AVASTIN®, GLEEVEC®, HERCEPTIN®, and mixtures thereof. Examples of chemotherapeutic agents for use in combination therapy include, but are not limited to, daunorubicin, DAUNOMYCIN®, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, TAXOL®, vincristine, vinblastine, etoposide (VP-16), trimetrexate, irinotecan, topotecan, gemcitabine, teniposide, cisplatin and diethylstilbestrol (DES).

Other antiviral agents can also be delivered in the treatment methods of the invention. For example, compounds that inhibit inosine monophosphate dehydrogenase (IMPDH) may have the potential to exert direct anti viral activity, and such compounds can be administered in combination with the mutant *Listeria*, as described herein. Drugs that are effective inhibitors of hepatitis C NS3 protease may be administered in combination with the mutant *Listeria*, as described herein. Hepatitis C NS3 protease inhibitors inhibit viral replication. Other agents such as inhibitors of HCV NS3 helicase are also attractive drugs for combinational therapy, and are contemplated for use in combination therapies described herein. Ribozymes such as HEPTAZYME™ and phosphorothioate oligonucleotides which are complementary to HCV protein sequences and which inhibit the expression of viral core proteins are also suitable for use in combination therapies described herein.

Examples of other agents for use in combination therapy of multiple sclerosis include, but are not limited to; glatiramer; corticosteroids; muscle relaxants, such as Tizanidine (ZANAFLEX®) and baclofen (LIORESAL®); medications to reduce fatigue, such as amantadine (SYMMETREL®) or modafinil (PROVIGIL®); and other medications that may also be used for depression, pain and bladder or bowel control problems that can be associated with MS.

Other exemplary agents that may be administered in combination therapy are described in U.S. Pat. No. 8,580,939, the contents of which are incorporated herein by reference.

In the context of a combination therapy, combination therapy compounds may be administered by the same route of administration (e.g. intrapulmonary, oral, enteral, etc.) that the mutant *Listeria* are administered. In the alternative, the compounds for use in combination therapy with the mutant *Listeria* may be administered by a different route of administration.

The additional agent can be administered immediately before (or after) the *Listeria*, on the same day as, one day before (or after), one week before (or after), one month before (or after), or two months before (or after) the *Listeria*, and the like.

The *Listeria* and the second reagent can be administered concomitantly, that is, where the administering for each of these reagents can occur at time intervals that partially or fully overlap each other. The *Listeria* and second reagent can be administered during time intervals that do not overlap each other. For example, the first reagent can be administered within the time frame of t=0 to 1 hours, while the second reagent can be administered within the time frame of t=1 to 2 hours. Also, the first reagent can be administered within the time frame of t=0 to 1 hours, while the second reagent can be administered somewhere within the time frame of t=2-3 hours, t=3-4 hours, t=4-5 hours, t=5-6 hours, t=6-7 hours, t=7-8 hours, t=8-9 hours, t=9-10 hours, and the like. Moreover, the second reagent can be administered somewhere in the time frame of t=minus 2-3 hours, t=minus 3-4 hours, t=minus 4-5 hours, t=5-6 minus hours, t=minus 6-7 hours, t=minus 7-8 hours, t=minus 8-9 hours, t=minus 9-10 hours.

To provide another example, the first reagent can be administered within the time frame of t=0 to 1 days, while the second reagent can be administered within the time frame of t=1 to 2 days. Also, the first reagent can be administered within the time frame of t=0 to 1 days, while the second reagent can be administered somewhere within the time frame of t=2-3 days, t=3-4 days, t=4-5 days, t=5-6 days, t=6-7 days, t=7-8 days, t=8-9 days, t=9-10 days, and the like. Moreover, the second reagent can be administered somewhere in the time from of t=minus 2-3 days, t=minus 3-4 days, to t=minus 4-5 days, t=minus 5-6 days, t=minus 6-7 days, t=minus 7-8 days, t=minus 8-9 days, t=minus 9-10 days, and the like.

In another aspect, administration of the *Listeria* can begin at t=0 hours, where the administration results in a peak (or maximal plateau) in plasma concentration of the *Listeria*, and where administration of the second reagent is initiated at about the time that the concentration of plasma *Listeria* reaches said peak concentration, at about the time that the concentration of plasma *Listeria* is 95% said peak concentration, at about the time that the concentration of plasma *Listeria* is 90% said peak concentration, at about the time that the concentration of plasma *Listeria* is 85% said peak concentration, at about the time that the concentration of plasma *Listeria* is 80% said peak concentration, at about the time that the concentration of plasma *Listeria* is 75% said peak concentration, at about the time that the concentration of plasma *Listeria* is 70% said peak concentration, at about the time that the concentration of plasma *Listeria* is 65% said peak concentration, at about the time that the concentration of plasma *Listeria* is 60% said peak concentration, at about the time that the concentration of plasma *Listeria* is 55% said peak concentration, at about the time that the concentration of plasma *Listeria* is 50% said peak concentration, at about the time that the concentration of plasma *Listeria* is 45% said peak concentration, at about the time that the concentration of plasma *Listeria* is 40% said peak concentration, at about the time that the concentration of plasma *Listeria* is 35% said peak concentration, at about the time that the concentration of plasma *Listeria* is 30% said peak concentration, at about the time that the concentration of plasma *Listeria* is 25% said peak concentration, at about the time that the concentration of plasma *Listeria* is 20% said peak concentration, at about the time that the concentration of plasma *Listeria* is 15% said peak concentration, at about the time that the concentration of plasma *Listeria* is 10% said peak concentration, at about the time that the concentration of plasma *Listeria* is 5% said peak concentration, at about the time that the concentration of plasma *Listeria* is 2.0% said peak concentration, at about the time that the concentration of plasma *Listeria* is 0.5% said peak concentration, at about the time that the concentration of plasma *Listeria* is 0.2% said peak concentration, or at about the time that the concentration of plasma *Listeria* is 0.1%, or less than, said peak concentration.

In another aspect, administration of the second reagent can begin at t=0 hours, where the administration results in a peak (or maximal plateau) in plasma concentration of the second reagent and where administration of the *Listeria* is initiated at about the time that the concentration of plasma level of the second reagent reaches said peak concentration, at about the time that the concentration of plasma second reagent is 95% said peak concentration, at about the time that the concentration of plasma second reagent is 90% said peak concentration, at about the time that the concentration of plasma second reagent is 85% said peak concentration, at about the time that the concentration of plasma second reagent is 80% said peak concentration, at about the time that the concentration of plasma second reagent is 75% said peak concentration, at about the time that the concentration of plasma second reagent is 70% said peak concentration, at about the time that the concentration of plasma second reagent is 65% said peak concentration, at about the time that the concentration of plasma second reagent is 60% said peak concentration, at about the time that the concentration of plasma second reagent is 55% said peak concentration, at about the time that the concentration of plasma second reagent is 50% said peak concentration, at about the time that the concentration of plasma second reagent is 45% said peak concentration, at about the time that the concentration of plasma second reagent is 40% said peak concentration, at about the time that the concentration of plasma second reagent is 35% said peak concentration, at about the time that the concentration of plasma second reagent is 30% said peak concentration, at about the time that the concentration of plasma second reagent is 25% said peak concentration, at about the time that the concentration of plasma second reagent is 20% said peak concentration, at about the time that the concentration of plasma second reagent is 15% said peak concentration, at about the time that the concentration of plasma second reagent is 10% said peak concentration, at about the time that the concentration of plasma second reagent is 5% said peak concentration, at about the time that the concentration of plasma reagent is 2.0% said peak concentration, at about the time that the concentration of plasma second reagent is 0.5% said peak concentration, at about the time that the concentration of plasma second reagent is 0.2% said peak concentration, or at about the time that the concentration of plasma second reagent is 0.1%, or less than, said peak concentration. As it is recognized that alteration of the *Listeria* or second reagent may occur in vivo, the above concentrations can be assessed after measurement of intact reagent, or after measurement of an identifiable degradation product of the intact reagent.

Kits:

Kits with unit doses of the subject mutant *Listeria*, e.g., in oral or injectable doses, are provided. In such kits, in addition to the containers containing the unit doses will be an informational package insert describing the use and attendant benefits of the mutant *Listeria* in treating a pathological condition of interest. U.S. Pat. No. 8,679,476 discloses additional mutations, which affect interferon B production, the entire contents of which is incorporated by reference.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Examples

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Bacterial Strains, Cells, Growth Media and Reagents.

*L. monocytogenes* 10403S strain was used as wild type (WT) strain and as parental strain for all mutants generated in this work (Table 1). *E. coli* XL-1 blue strain (Stratagene) and *E. coli* DH12 were used for vector propagation. *E. coli* SM-10 strain (48) was used for conjugative plasmid delivery to *L. monocytogenes*. *L. monocytogenes* strains were grown in brain heart infusion (BHI, BD©) media or minimal media (49) at 37° C. and *E. coli* strains were grown in Luria Bertani (LB, BD©) media at 37° C. For infection experiments *L. monocytogenes* bacteria were grown overnight in BHI at 30° C. without agitation. IPTG (Isopropyl β-D-1-thiogalactopyranoside) was purchased from Bio-Lab Ltd. (Israel), penicillin G, vancomycin hydrochloride and mutanolysin were purchased from Sigma, c-di-AMP and c-di-GMP from BIOLOG Institute (Germany). Primary bone marrow derived (BMD) macrophages were isolated from 6 to 8 weeks old female C57BL/6 mice (Harlan Laboratories Ltd, Israel) and cultured as described (50). RAW264 macrophages were grown and maintained in DMEM based media.

Generation of *L. monocytogenes* in Frame Deletion Mutants.

Deletion mutants were generated by standard techniques using pKSV7oriT vector, as described in (7). pLIV2-mdrM plasmid was used for generation of 6×His tagged MdrM and of F58V mutant (Table 2, herein below).

Protein Analysis by Western Blot.

Overnight cultures were diluted 1:100 and grown to O.D.$_{600}$ of 1 unit, than supplemented with 0.25 mM IPTG when indicated. Bacteria were harvested, treated with 50 units of mutanolysin for 1 hour and sonicated in 20 mM Tris-HCl at pH 8, 0.5 M NaCl, 1 mM EDTA, 1 mM PMSF. After removal of cell debris, membranes were collected by ultracentrifugation. Membrane fractions (50 ng of protein) were then subjected to 12.5% SDS-PAGE and blotted for His-tag detection using INDIA HisProbe-horseradish peroxidase (HRP) (Pierce) and enhanced chemiluminescence reagent (ECL).

Bacterial Growth Curves.

Overnight cultures were adjusted to 0.03 O.D.$_{600}$ in 20 ml fresh BHI broth, supplemented when indicated with 0.25 mM IPTG, 0.08 μg ml$^{-1}$ penicillin G, 1 μg ml$^{-1}$ vancomycin or 3 μg ml$^{-1}$ c-di-AMP. For bacterial RNA extraction, bacteria were grown at 37° C. to O.D.$_{600}$ 0.4, then supplemented with 3 μg ml$^{-1}$ lincomycin, 50 μM rhodamine 6 G (R6G), 1 μg ml$^{-1}$ vancomycin, 0.08 μg ml$^{-1}$ penicillin G for 2 h; or centrifuged and resuspended in minimal media pH 5 (lactic acid), minimal media with 10 mM H$_2$O$_2$, or defined minimal media pH 5 with 10 mM H$_2$O$_2$ for 30 mM For microscopy bacteria were grown similarly and supplemented with 1 μg ml$^{-1}$ vancomycin for 2 h. Growth curves in the presence of drugs were performed in a Synergy HT BIOTEK® plate reader at 37° C. with continuous shaking following O.D.$_{600}$ every 15 min for 24 h. Of note, bacterial growth in the plate reader is different than in flasks in respect to the O.D. levels that are measured. In each experiment, growth conditions are indicated.

*L. Monocytogenes* Intracellular Growth in Cells.

Intracellular growth curves were performed as described previously (51). Briefly, 2×10$^6$ cells were seeded on a petri dish with glass cover slips and infected with 8×10$^6$ bacteria. At 0.5 h.p.i. cells were washed and at 1 h.p.i. gentamicin was added. At each time point, cells from 3 cover slips were lyzed and CFUs were counted. For bacterial gene expression of intracellularly grown *L. monocytogenes*, 25×10$^6$ BMD macrophage cells were infected with 1×10$^8$ bacteria and lyzed in 20 ml of ice-cold water at 6 h.p.i. and the released bacteria were collected on 0.45 μm HA filters (Millipore, Cat. HAWP04700).

Gene Expression Analysis.

RNA was purified from bacteria in mid-log growth in BHI or from infected cells using standard phenol-chloroform extraction methods. RNA from intracellularly grown bacteria was amplified using MESSAGEAMP™ II (AMBION™) bacterial RNA amplification kit according to the manufacturer's instructions. RNA of infected macrophages was extracted using TRIZOL® reagent according to standard protocols. In all cases, one microgram (1 μg) of RNA was reverse transcribed to cDNA using High Capacity reverse transcription kit (APPLIED BIOSYSTEMS™). RT-qPCR was performed on 10 ng of cDNA using SYBR® Green with Step-one Plus RT-PCR system (APPLIED BIOSYSTEMS™). The transcription of bacterial genes was normalized using 16S rRNA or rpoB gene, and of macrophage cytokines using gpdh. Statistical analysis was performed using the STEPONE™ V2.1 software. Error bars represent 95% confidence interval; in a case where the error bars of two samples do not overlap the p value is <<0.01. Primers sequences are described in Table 1 herein below. The complete intracellular expression profile of *L. monocytogenes* 10403S was published separately (21).

Beta-Galactosidase MUG Assay for mdrC Transcription.

Overnight cultures of WT L.m. pPL2-P$_{mdrC}$lacZ and ΔmdrMTA pPL2-P$_{mdrC}$lacZ were adjusted to O.D.$_{600}$ 0.05. Cultures were grown in 96-well black plates (200 μl) with a clear bottom to O.D.$_{600}$~0.4 at 37° C. Next, the plates were centrifuged for 10 min at 3800 rpm, supernatants were aspirated and the cells were washed twice with PBS. 200 μl of ABT buffer (60 mM K$_2$HPO$_4$, 40 mM KH$_2$PO$_4$, 100 mM NaCl, 0.1% TRITON® X-100, pH=7), supplemented with 80 μg/ml of MUG substrate (4-methylumbelliferyl beta-D-galactopyranoside, Sigma) were added to each well. Plates were shaken for 30 sec and incubated at room temperature for 1 hour in the dark. Following incubation, the optical density (600 nm) and the fluorescence intensity (excitation 360 nm, emission 460 nm) were measured using a Synergy HT BIOTEK® plate reader. Beta-Galactosidase activity was normalized to the samples O.D. (52, 53). The experiment was performed in triplicates and was repeated three times independently.

Transmission Electron Microscopy.

Bacteria were grown as described above with and without vancomycin treatment. For negative staining, PBS washed bacteria were adsorbed on formvar/carbon coated grids and stained with 2% aqueous uranyl acetate. For TEM sections, a bacterial pellet from 20 ml of culture was fixed in 2.5% glutaraldehyde in PBS at 4° C. for 20 h, washed three times with PBS and post-fixed in 1% OsO4 in PBS at 4° C. for 2 h. Dehydration was carried out in graded ethanol and embedding in glycid ether. Thin sections were mounted on formvar/carbon-coated grids and stained with uranyl acetate and lead citrate. All images were acquired using Jeol 1200 EX transmission electron microscope (Jeol, Japan). Cell wall thickness measurements were performed from three independent biological repeats, a total of 35 frames were taken for each strain and condition.

Mice Infection.

*L. monocytogenes* bacteria were grown in BHI medium at 30° C. overnight. C57BL/6 (6-8 weeks old) female mice (Harlan Laboratories Ltd, Israel) were infected via tail vein injections with 4×10$^4$ washed bacteria (5 mice in each group). Spleens and livers were harvested 72 h.p.i. and homogenized in 0.2% saponin, and bacterial CFU was determined by plating. The experiment was repeated twice.

Measurement of Peptidoglycan Synthesis Rate.

Overnight bacterial culture was diluted 1:100 into 10 ml of BHI, grown to O.D.$_{600}$ of 0.4, and supplemented with 20 µM of N-acetylglucosamine and 10 µl of 1 µCi µl$^{-1}$ of [$^{14}$C]-N-acetylglucosamine (American Radiolabeled Chemicals). Then the culture was divided in two and 0.8 µg to ml$^{-1}$ of vancomycin was added to one of them. 100 µl aliquots from cultures incubated without agitation at 37° C. were withdrawn in triplicates every 30 min and added to 100 µl of boiling 8% SDS and incubated for 5 min at 95° C. Cell-wall was collected on 0.45 µm pore size membrane filters (Millipore ref: HAWP02500), washed with 15 ml of water and counted using 5 ml of ECOLITE(+)™ liquid scintillation cocktail at PerkinElmer TriCarb 3110TR β-counter.

Peptidoglycan Extraction and Muropeptides Analysis.

Cell wall and peptidoglycan were purified as described (54). Muropeptides were generated from highly purified cell wall and peptidoglycan samples by mutanolysin and then reduced using sodium borohydride. Muropeptides separation was performed by HPLC as previously described for *L. monocytogenes* (55, 56). For activation of cytokines by cell wall samples, lyophilized cell wall extracts were resuspended at a concentration of 1.5 mg ml$^{-1}$, then the pH was adjusted to 7.5 with NaOH, and 20 µl were added to 2*10$^6$ BMD macrophages in 2.5 ml medium. After 6 h, macrophage RNA was harvested and analyzed for cytokines induction.

Results

A Functional MdrM Transporter is Required to Trigger Macrophage Cells to Elicit the IFN-β Response

*L. monocytogenes* bacteria over expressing MdrM transporter have been shown to trigger infected macrophage cells to express enhanced IFN-β levels (7). In order to validate that the enhancement of the IFN-β response requires MdrM to be functional, an mdrM mutant was generated harboring a mutation that inactivates function but preserves expression. Using site-directed mutagenesis, phenylalanine in MdrM at position 58, F58, was substituted with valine. The resulting mdrM-F58V gene construct was tagged with histidine at the 3'-end and cloned into the integrative pLIV2 vector under an IPTG-inducible promoter to generate pLIV2-mdrM-F58V-6His. This plasmid or a control plasmid containing the His-tagged native mdrM gene (pLIV2-mdrM-6His) was conjugated to a ΔmdrM mutant and the expression levels of the native and mutated MdrM compared by Western blot analysis. Indeed, both the native MdrM and MdrM-F58V proteins were expressed and found in the membrane fraction at similar levels upon IPTG addition (FIG. 1A). Next, the ability of MdrM and MdrM-F58V proteins to confer resistance to R6G was tested. As expected, the to ΔmdrM mutant was more sensitive to R6G in comparison to wild type (WT) bacteria and introduction of the native mdrM gene (via pLIV2-mdrM-6His with IPTG induction) rescued the sensitivity. However, introduction of MdrM-F58V did not restore full growth, providing support that the F58V mutation does interfere with MdrM's transport function (FIG. 1B). Next, the capacity of this mutant to enhance the IFN-β response was tested. To this end, macrophage cells were infected with the ΔmdrM mutant harboring pLIV2 plasmid expressing the native or the mutated MdrM. As shown in FIG. 1C, all strains grew to a similar extent intracellularly (FIG. 1C). Notably, only bacteria over-expressing the native MdrM induced an enhanced IFN-β response while bacteria over-expressing the mutated MdrM did not (FIG. 1D). These results indicate that MdrM's function is required for inducing an IFN-β response during infection.

MdrM Transporter and Several MDR Homologs are Transcriptionally Induced During Intracellular Growth MDR transporters are known to exhibit functional redundancy due to overlapping substrate specificity (9, 20). Since MdrM was shown to be responsible for a third of the IFN-β induction by infected macrophage cells (7), the present inventors examined if additional transporters are involved in mediating the IFN-β response. A search of the *L. monocytogenes* strain 10403S genome for mdrM homologs revealed several genes encoding putative MDR transporters, among them the previously identified mdrT (Table 1, herein below).

TABLE 1

Genes similar to mdrM in *L. monocytogenes* 10403S strain (based on protein sequence)

| Gene name | Induced intracelu-llarly* | % identity, % similarity a. a. sequence | *L.m.* EDGe gene identifier | *L.m.* 10403S Gene |
|---|---|---|---|---|
| mdrM | Yes | — | lmo1617 | LMRG_02976.6 |
| mdrT | Yes | 45%, 65% | lmo2588 | LMRG_02679.6 |
| mdrA | Yes | 35%, 60% | lmo0519 | LMRG_00200.6 |
| — | No | 25%, 46% | lmo0981 | LMRG_02080.6 |
| mdrB | Yes | 23%, 44% | lmo2845 | LMRG_01853.6 |
| mdrC | Yes | 22%, 41% | lmo2818 | LMRG_01880.6 |
| mdrD | Yes | 20%, 38% | lmo0872 | LMRG_02296.6 |
| mdrE | Yes | 16%, 33% | lmo2826 | LMRG_01872.6 |

Figure 2:
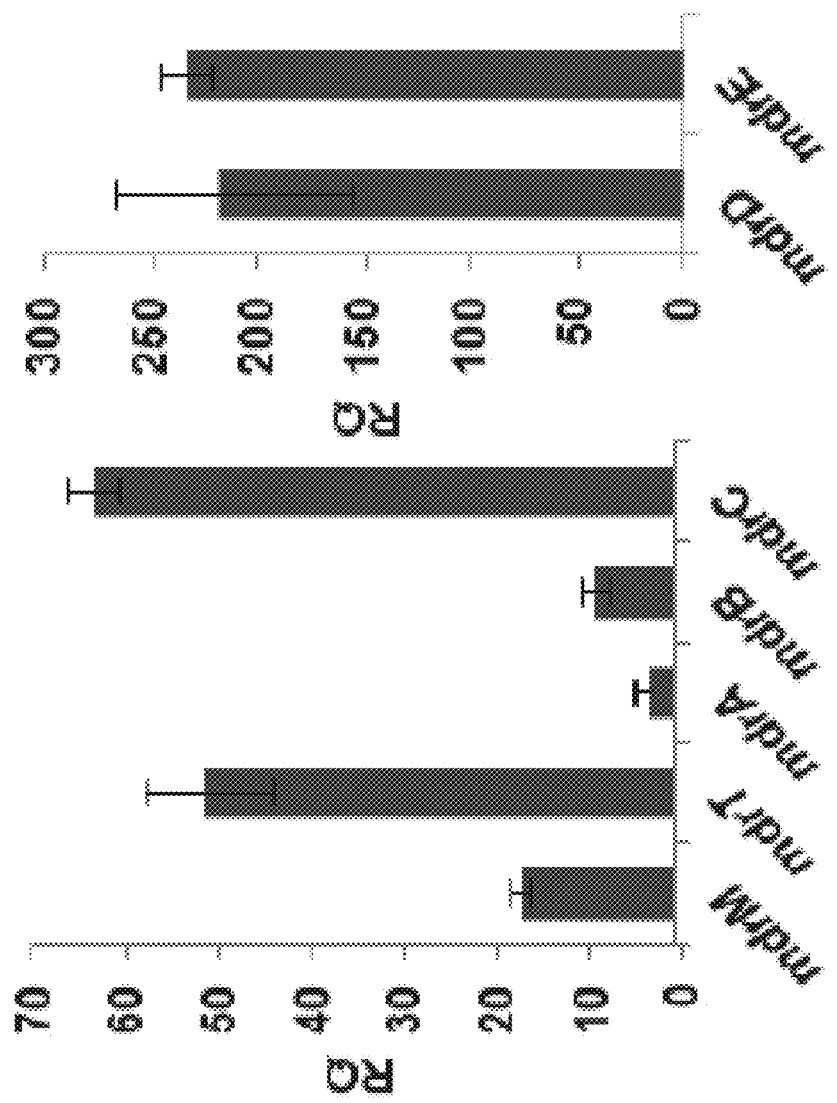

Included in this list, the LMRG 00200.6 gene (an ortholog of lmo0519 in EGD-e), named here mdrA, was highly similar to mdrM and mdrT with 60% similarity and 45% identity in protein sequence, whereas the other proteins exhibited only 33-44% sequence similarity (Table 1). To gain insight into the potential requirement for these transporters during *L. monocytogenes* infection, their transcription levels was analyzed during intracellular growth in macrophage cells. to Transcriptomic data of intracellularly grown bacteria indicated that all of these transporters are induced during infection of macrophage cells, except for LMRG_02080.6 (using microarray analysis (21) (Table 1). Accordingly, the transcription levels of the induced MDR transporters were compared by real-time quantitative PCR (RT-qPCR) analysis. As shown in FIG. 2, all of the transporters were transcriptionally up-regulated during intracellular growth in macrophage cells, at least 4-fold, over their levels in BHI. These results suggest that each of the transporters might play an active role during *L. monocytogenes* infection.

A Set of MdrM-Like Transporters Control Most of the Type I Interferon Response to *L. monocytogenes* Infection and Virulence To examine whether MdrM-homologs contribute to IFN-β induction during infection, a series of in-frame deletion mutants, harboring single or multiple (double, triple, quadruple and quintuple) MDR gene deletions were generated (Table 2, herein below).

TABLE 2

Bacterial strains

| Strain | Genotype | Reference |
|---|---|---|
| *Listeria monocytogenes* | | |
| 10403S | Wild type, Str r (WT) | Portnoy, DA lab stock |
| ΔmdrM | ΔmdrM | (Crimmins et al., 2008) |
| ΔmdrA | ΔmdrA | This study |
| ΔmdrC | ΔmdrC | This study |
| ΔmdrB | ΔmdrB | This study |
| ΔmdrD | ΔmdrD | This study |
| ΔmdrE | ΔmdrE | This study |
| ΔmdrMC | ΔmdrM ΔmdrC | This study |
| ΔmdrMTA | ΔmdrM ΔmdrT ΔmdrA | This study |
| ΔmdrMTAC | ΔmdrM ΔmdrT ΔmdrA ΔmdrC | This study |
| ΔmdrMTAB | ΔmdrM ΔmdrT ΔmdrA ΔmdrB | This study |
| ΔmdrMTAD | ΔmdrM ΔmdrT ΔmdrA ΔmdrD | This study |
| ΔmdrMTAE | ΔmdrM ΔmdrT ΔmdrA ΔmdrE | This study |
| ΔmdrMTABC | ΔmdrM ΔmdrT ΔmdrA ΔmdrB ΔmdrC | This study |
| ΔmdrM pLIV2-mdrM-6His | ΔmdrM [pLIV2:mdrM-6His] | (Crimmins et al., 2008) |
| ΔmdrM pLIV2-mdrM-F58V-6His | ΔmdrM [pLIV2:mdrMF58V-6His] | This study |
| ΔmdrMTAC pLIV2-mdrM-6His | ΔmdrMTAC [pLIV2:mdrM-6His] | This study |
| ΔmdrMTAC pLIV2-mdrT | ΔmdrMTAC [pLIV2:mdrT] | This study |
| ΔmdrMTAC pLIV2-mdrA | ΔmdrMTAC [pLIV2:mdrA] | This study |
| ΔmdrMTAC pLIV2-mdrC | ΔmdrMTAC [pLIV2:mdrC] | This study |
| WT *L.m.* pLIV2-pdeA | [pLIV2:pdeA] | This study |
| ΔmdrMTAC pLIV2-pdeA | ΔmdrM ΔmdrT ΔmdrA ΔmdrC [pLIV2:pdeA] | This study |
| WT *L.m.* pLIV2-dacA | [pLIV2:dacA] | This study |
| ΔmdrMTAC pLIV2-dacA | ΔmdrM ΔmdrT ΔmdrA ΔmdrC [pLIV2:dacA] | This study |
| ΔmarR | ΔmarR (LMRG_01348.6, lmo1618) | (Crimmins et al., 2008) |
| pPL2-P$_{mdrC}$lacZ | WT *L.m.* harboring the integrative plasmid pPL2 encoding lacZ gene under promoter of mdrC. | This study |
| ΔmdrMTA pPL2-P$_{mdrC}$lacZ | ΔmdrMTA *L.m.* harboring the integrative plasmid pPL2 encoding lacZ gene under promoter of mdrC. | This study |
| *Escherichia coli* | | |
| DH12s | 80dlacZΔM15 mcrA Δ(mrr-hsdRMS-mcrBC) araD139 Δ(ara, leu)7697 Δ(lacX74 galU galK rpsL (Strr) nupG recA1/F' proAB+ lacIqZΔM15 | (Lin et al., 1992) |
| XL-1b | recA1 endA1 gyrA96 thi-1 hsdR17 supE44 relA1 lac [F' proAB lacIqZΔM15 Tn10 (Tetr)]. | Stratagene |
| SM-10 | Conjugation donor; F-thi-1 thr-1 leuB6 recA tonA21 lacY1 supE44 (Muc+) λ-[RP4-2(Tc::Mu)] Kmr Tra+ | (Simon et al., 1983) |

TABLE 3 primer sequences

| Name | Sequence (5'-3') | SEQ ID NO: |
|---|---|---|
| mdrD-F | TGAATGTGTCTGGTTTGCAACTTTAT | 19 |
| mdrD-R | AAGCCATGCTAACCGTTTCTG | 20 |
| mdrC-F | GGCCGTGCAATCTGACCTT | 21 |
| mdrC-R | CCTGAGAATAGCGCGGTTAAA | 22 |
| mdrB-F | CGCAAATCAACGCCACAAT | 23 |
| mdrB-R | CAGAGCCAAGAATTCCGAAGA | 24 |
| mdrM-F | CAGCAAGTACATCAGTGAAGCGTAA | 25 |
| mdrM-R | GGTAGCGCGACATTCATCAA | 26 |
| mdrT-F | CCGTGCGGTTCTTCGGTAT | 27 |
| mdrT-R | TTTACTGCCGAACCGTGGTT | 28 |
| mdrA-F | GCAACAGGTGGGCAGAAAAT | 29 |
| mdrA-R | GCGCCATGTTAAGAGCAGTTT | 30 |
| hly-F | TAAAAACAATGTATTAGTATACCACGG | 31 |
| hly-R | GATTCACAACTTGAATGTCTGC | 32 |

TABLE 3-continued primer sequences

| Name | Sequence (5'-3') | SEQ ID NO: |
|---|---|---|
| rpoB-F | GCGGATGAAGAGGATAATTACG | 33 |
| rpoB-R | TAGTCAATACGTTCTTTTTCTACC | 34 |
| mdrE-F | GTGGAACGCAAATGGAAGCT | 35 |
| mdrE-R | TTCCAACTCCCAGCAATCG | 36 |
| 16S rRNA-F | CCTGGTAGTCCACGCCGT | 37 |
| 16S rRNA-R | TGCGTTAGCTGCAGCACTAAG | 38 |
| dacA-RT-F | CGTGAACAGCATCATTTAATCGA | 39 |
| dacA-RT-R | GTATCGCGTGCCACTGAAATC | 40 |
| pdeA-F | CCAACTGGGCTAGGGAACATC | 41 |
| pdeA-R | CCTCCGTCAAAAAGGCCATA | 42 |
|  |  | 43 |
| Ifnβ-F | CCAAGAAAGGACGAACATTCG | 44 |
| Ifnβ-R | CCGCCCTGTAGGTGAGGTT | 45 |
| gapDH-F | TTGTGGAAGGGCTCATGACC | 46 |
| gapDH-R | TCTTCTGGGTGGCAGTGATG | 47 |
| IL1α-F | AGGAGAGCCGGGTGACAGTA | 48 |
| IL1α-R | TCAGAATCTTCCCGTTGCTTG | 49 |
| IL6-F | TTCCATCCAGTTGCCTTCTTG | 50 |
| IL6-R | GAAGGCCGTGGTTGTCACC | 51 |
| A-SalI-F-mdrB | ACTATGTCGACGCAGTAATCACGTTCTTGCGCA | 52 |
| mdrB-B-R | TCGGTAACCGGAATACAAGTAGGTATTACGTTTATTCGTCTGTTCCATGA | 53 |
| mdrB-C-F | TCATGGAACAGACGAATAAACGTAATACCTACTTGTATTCCGGTTACCGA | 54 |
| mdrB-D-PstI-R | ATTACCTGCAGAGCTTGCTGGCAAGTATTTCTT | 55 |
| mdrE-A2-KPNI-F | ATACTGGTACCCTTTGTAATTATCTGGAATCTCCATC | 56 |
| mdrE-B-R | GACAAGACTTTGGACGAAGGACAATAGCTAACATCTCTTGTGAAGTG | 57 |
| mdrE-C-F | CACTTCACAAGAGATGTTAGCTATTGTCCTTCGTCCAAAGTCTTGTC | 58 |
| mdrE-D2-Pst-R | ATAACCTGCAGTAACGAGTCCGC\CAGAAGTGG | 59 |
| mdrC-A-SalI-F | ATTATGTCGACTCAGAAATGCCCGTTAGGTACT | 60 |
| mdrC-B-R | AGAATAACTAATGACTTCAACAGCGTAGCGCTCGAATTAAAAGCCGCA | 61 |
| mdrC-C-F | TGCGGCTTTTAATTCGAGCGCTACGCTGTTGAAGTCATTAGTTATTCT | 62 |
| mdrD-A-SalI-F | ATTATGTCGACTCTCATTTATGCGCTAGATTATCC | 63 |
| mdrD-B-R | AAGGCCTATTATTTGAACTATTTATCTTTTCATATCCACATTGTTTCCCCCTA | 64 |
| mdrD-C-F | TAGGGGGAAACAATGTGGATATGAAAAGATAAATAGTTCAAATAATAGGCCTT | 65 |
| mdrD-D-PstI-R | ATTATCTGCAGTTTCTAGCGCCTTATCGAGCT | 66 |
| mdrA-A-SalI-F | ATTATGTCGACCACGGTCAGTTGTGTTTAGCATTG | 67 |
| mdrA-B-R | TCGCTTTATTATTTAGCTTTACGACCTGTTGCTTCTTGTTGCAT | 68 |
| mdrA-C-F | ATGCAACAAGAAGCAACA | 69 |

All the MDR mutants grew similarly to WT bacteria both in BHI broth and intracellularly in macrophage cells, except for mdrMTAD mutant that exhibited a moderate intracellular growth defect (FIGS. 8A-B). The IFN-β response elicited by macrophages after infection with each one of the mutants was evaluated using RT-qPCR analysis of IFN-β transcript levels. Overall, it was observed that the greater the number of transporters that were deleted, the lower the IFN-β levels expressed by infected cells (FIG. 3A). Notably, macrophages infected with the quadruple mutant named ΔmdrMTAC (deleted of mdrM, mdrT, mdrA and mdrC genes) exhibited the to lowest IFN-β level among the tested mutants, approximately 15% the amount of IFN-β relative to macrophages infected with WT bacteria. Infection with the ΔmdrMTAC mutant was also observed to induce macrophages to transcribe low levels of IL-6 but normal levels of IL-1α, indicating that the action of these transporters primarily affects the induction of the type I interferon response (in which both IL-6 and IFN-β are included) (FIG. 3B). The latter observation corroborated previous characterization of the ΔmdrM mutant showing it to particularly modulate the type I interferon response rather than general pro-inflammatory responses (7). In summary, this analysis revealed that several MDR transporters, homologs of MdrM, are functionally involved in the activation of type I interferon response during L. monocytogenes infection.

Since the ΔmdrMTAC mutant grew like WT bacteria in macrophage cells (FIG. 8B) yet triggered a reduced type I interferon response, the present inventors examined if this phenotype influenced virulence in mice. C57BL/6 young female mice were injected intravenously with ΔmdrMTAC mutant or WT bacteria (total of 10 mice for each strain). Seventy-two hours post infection (h.p.i.) a log decrease in the number of bacterial colony forming units (CFU) was observed in the livers and spleens of ΔmdrMTAC-infected mice in comparison to that observed in mice infected with WT bacteria (FIG. 3C). These results further support the premise that the MdrM-like transporters are active in vivo, and play a role in promoting L. monocytogenes virulence.

MdrM-Like Transporters are Expressed and Required During Cell Wall Stress

In order to identify the physiological process that induces the transporters' function in vivo, the transcription profile of four transporter genes was measured using RT-qPCR analysis under a set of in vitro conditions that mimic different physiological environments. In these studies the four transporters MdrM, MdrT, MdrA and MdrC (MTAC transporters) were analyzed, as together these were responsible for most of the IFN-β induction during infection of macrophages. The conditions involved cell wall stresses (growth in the presence of vancomycin or penicillin G), acidic pH (near 5), oxidative stress (using hydrogen peroxide) and growth in minimal media, all representing conditions that likely exist within the phagosome compartment. In additions, growth in the presence of glucose-1P and charcoal was tested as these conditions are known to activate PrfA, the master regulator of *L. monocytogenes* virulence (22). Lincomycin and R6G served as positive controls for MDR substrates known to induce expression of MDR transporters (7, 8). The hly gene (encoding LLO toxin) was used as a reporter for the induction of virulence genes.

To summarize the RT-qPCR results, the data is presented as a heat map (FIG. 4A). In general it was observed that while the transporter genes were largely induced by lincomycin and R6G, they were down regulated under all conditions that triggered hly expression (FIG. 4A). These findings indicate that the transporters and the virulence genes are differentially regulated, suggesting that different signals may induce the MDR transporters in vivo. Notably, among the tested conditions, growth in the presence of vancomycin and penicillin G resulted in up-regulation of most transporter genes, with the exception of mdrC that was down-regulated under these conditions (FIGS. 4A-B). Vancomycin and penicillin G are both inhibitors of peptidoglycan (PGN) synthesis and operate extracellularly on the expanding PGN polymer by blocking PGN-peptides from cross-linking. Vancomycin is a branched tricyclic glycosylated heptapeptide that targets the terminal D-alanyl-D-alanine moiety of PGN-peptides, while penicillin G, a beta-lactam antibiotic, is a structural analogue of D-alanyl-D-alanine that inhibits transpeptidation.

To examine more directly if the transporters play a role in the response to vancomycin and penicillin G treatments, transporter mutants and WT bacteria were grown in the presence of sub-lethal concentrations of these drugs (1 μg ml$^{-1}$ of vancomycin and 0.08 μg ml$^{-1}$ of penicillin G). Interestingly, the quadruple ΔmdrMTAC mutant was more susceptible to these drugs, whereas WT, ΔmdrMTA and ΔmdrC bacteria grew similarly (FIG. 4C). The minimal inhibitory concentrations of penicillin and vancomycin were determined as 0.08 μg ml$^{-1}$ and 1.5 μg ml$^{-1}$ for ΔmdrMTAC and, 0.15 μg ml$^{-1}$ and 2 μg ml$^{-1}$ for WT bacteria, respectively. To assess the contribution of MdrC in the background of ΔmdrMTA mutant, the present inventors analyzed its transcription level in ΔmdrMTA and WT bacteria, using a translational fusion of the lacZ reporter gene to the mdrC promoter region. Notably, they observed that the transcription level of mdrC gene in the ΔmdrMTA mutant was up-regulated (3-fold) in comparison to its level in WT bacteria (FIG. 9). These observations suggest that the Mdr transporters exhibit redundant activities and that they are respectively regulated in order to compensate for each other. Indeed, introducing in trans a copy of each one of the transporter genes to the ΔmdrMTAC mutant (using the pLIV2 inducible plasmid) only partially complemented its growth ability under vancomycin treatment (FIG. 10). Overall, these results indicate that the Mdr transporters play an active, and overlapping role, in response to vancomycin and penicillin G Importantly, since vancomycin and penicillin G operate extracellularly on the PGN polymer and are not expected to cross the cytoplasmic membrane to the bacterial cytosol (particularly vancomycin), a simple drug-efflux mechanism cannot explain the increased sensitivity of the ΔmdrMTAC mutant to these to drugs. In subsequent studies only vancomycin was used, since active efflux has never been reported as a mechanism of resistance for this drug.

The ΔmdrMTAC Mutant Responds Aberrantly to Cell Wall Stress

Figure 5A:
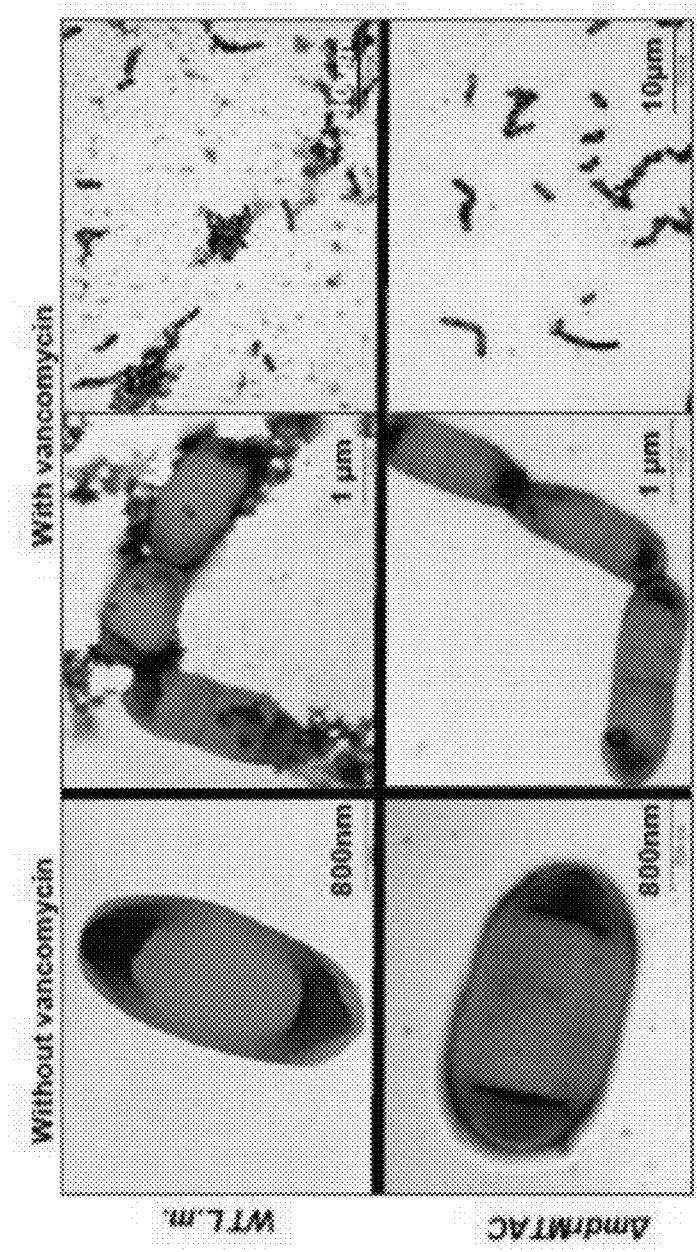
Figure 5B:
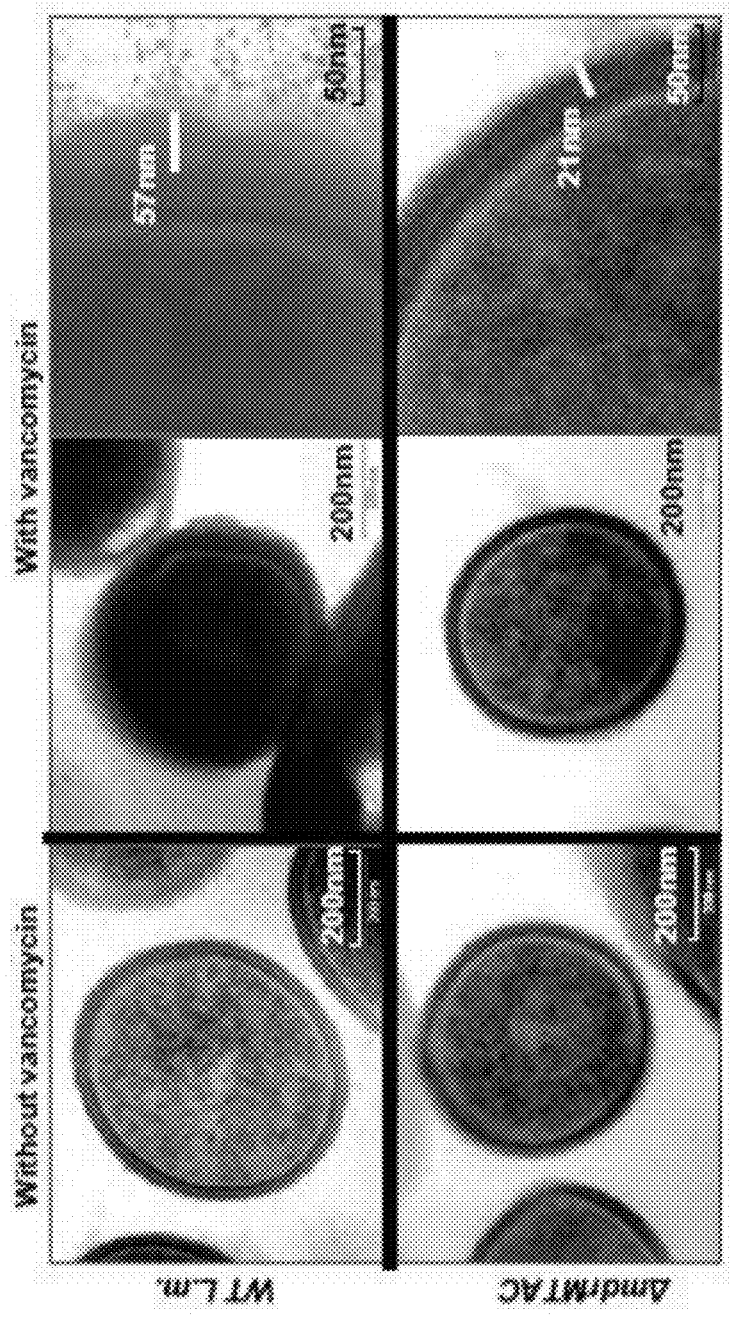

To gain insight into the functional role of the MDR transporters during vancomycin stress, bacteria were examined using transmission electron microscopy (TEM). Changes in cell wall morphology are expected upon inhibition of PGN synthesis, and therefore it was expected that there would be visual differences between ΔmdrMTAC and WT bacteria upon vancomycin treatment. Inspection of TEM images confirmed that when grown without vancomycin treatment both bacterial strains look similar (FIG. 5A). However, two hours subsequent to addition of a sub-lethal concentration of vancomycin, WT bacteria were surrounded by massive extracellular material that was largely lacking around the ΔmdrMTAC mutant (FIG. 5A). Further analysis of TEM sections revealed that without vancomycin treatment WT bacteria and ΔmdrMTAC mutant exhibit a similar defined cell wall structure with an average thickness of 21 nm (p value=0.1, based on 50 measurements) (FIG. 5B). In contrast, under vancomycin treatment WT bacteria and the ΔmdrMTAC mutant were found to be significantly different (p value<0.001, based on 100 measurements). Under these conditions a large population of the WT bacteria exhibited a very thick cell wall layer of up to 63 nm (FIG. 5B). The cell wall thickness ranged from 25 to 63 nm (35 nm average), as opposed to the range of 18 to 26 nm (24 nm average) associated with ΔmdrMTAC mutant bacteria (FIG. 5B). Cell wall thickening in response to vancomycin stress was reported previously for *S. aureus* bacteria, which were shown to respond to vancomycin treatment by accumulating peptidoglycan to facilitate vancomycin trapping (drug-titration) (23, 24). In accordance with this mechanism, WT *L. monocytogenes* that were observed to undergo cell wall thickening in the presence of vancomycin grew better than the ΔmdrMTAC mutant (FIGS. 5C and 4C). These observations suggest that the ΔmdrMTAC mutant might be defective in the ability to produce peptidoglycan upon vancomycin stress.

To further corroborate this hypothesis, 14C-N-acetyl glucosamine incorporation measurements were performed to assess the rate of PGN synthesis during growth with and without vancomycin treatment. Bacteria were grown to mid-log before vancomycin and 14C-N-acetyl glucosamine were added to the cultures. In this experiment even lower concentration of vancomycin was used (0.8 μg ml$^{-1}$) to reduce the growth inhibition of the ΔmdrMTAC mutant (FIG. 11). Every 30 minutes, samples of bacteria were filtrated, washed and counted for 14C-labeling. This analysis demonstrated that upon vancomycin treatment the rate of N-acetyl glucosamine incorporation was significantly slower in the ΔmdrMTAC mutant than that of WT bacteria (FIG. 5D). These differences in PGN synthesis were detectable even before inhibition of ΔmdrMTAC growth by vancomycin was observed (FIG. 11). Taken together, these results suggest that the MTAC transporters play a role in enhancing PGN synthesis upon vancomycin stress.

Figure 6A:
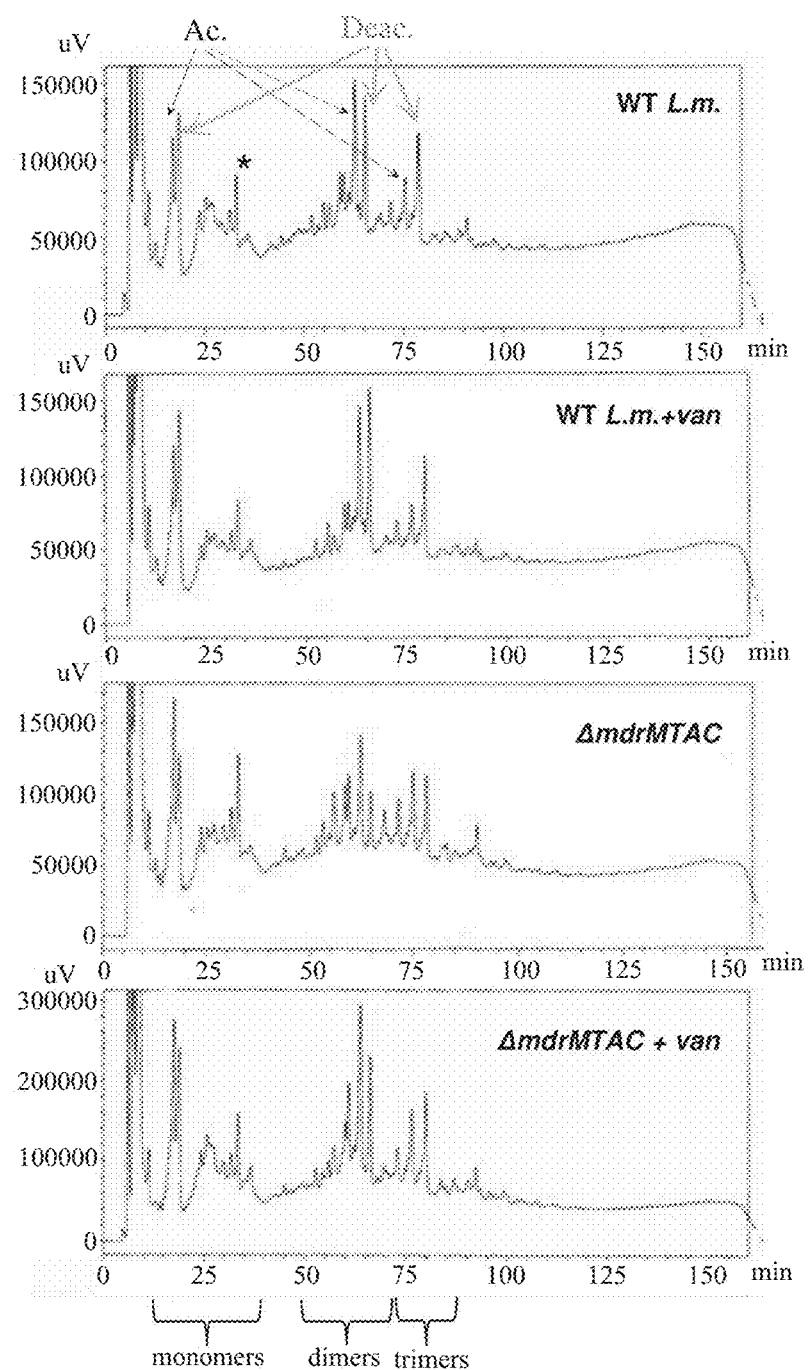

MdrM-Like Transporters are not Involved in PGN Assembly, Structure or its Immunostimulatory Activity To examine if the MTAC transporters are involved in PGN polymer assembly, the PGN structure of the ΔmdrMTAC mutant and WT bacteria were compared with and without vancomycin treatment. Cell wall was extracted from bacteria and digested with mutanolysin to generate a soluble mixture of PGN muropeptides. Muropeptides were separated by reversed-phase high-pressure liquid chromatography (RP-HPLC) and analyzed. Notably, no difference was observed in the muropeptide profile or their cross-linking levels between WT and ΔmdrMTAC bacteria (as evident from the detected peaks in the HPLC profile FIGS. 6A-B). Of note, a moderate difference of ~30% in the peptidoglycan N-acetylation level was observed, with the ΔmdrMTAC mutant displaying more N-acetylated muropeptides than WT bacteria (FIGS. 6A and C). Next, the immunostimulatory property of cell walls derived from each strain was compared. Cell wall extracts from ΔmdrMTAC and WT bacteria grown with and without vancomycin were added to BMD macrophages and IL-6 induction was measured using RT-qPCR analysis. IL-6 was chosen as it is induced by both type I interferon and pro-inflammatory responses. As shown in FIG. 6D, all extracts activated the same level of IL-6, indicating that the immunostimulatory potency of the ΔmdrMTAC cell wall is unchanged, in accordance with the overall similar structure of ΔmdrMTAC PGN to wild type PGN. Taken together these results indicate that the MTAC transporters are probably not involved in PGN polymer assembly, but play a role in the regulation of PGN synthesis during vancomycin stress.

c-di-AMP and Mdr-MTAC Transporters Regulate the Response to Cell Wall Stress

Figure 7A:
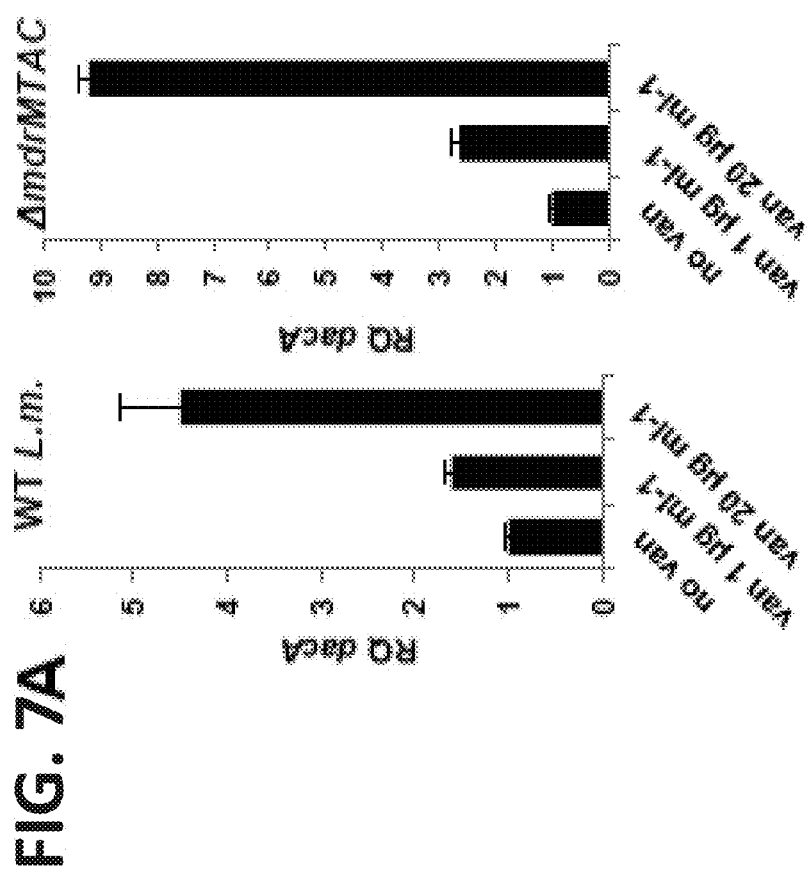

It was recently shown that *L. monocytogenes* MdrM and MdrT facilitate c-di-AMP secretion (11, 12). It was that the MDR transporters might regulate the enhancement of PGN synthesis in response to vancomycin by controlling c-di-AMP secretion. To provide evidence for a physiological association between c-di-AMP and the MTAC transporters, dacA transcription levels (which correlate with c-di-AMP production) were measured upon various vancomycin treatments using RT-qPCR analysis. WT bacteria and ΔmdrMTAC mutant grown in the presence of a sub-lethal concentration of vancomycin (1 μg ml$^{-1}$) or exposed briefly to high concentrations of vancomycin (20 μg ml$^{-1}$ for 10 minutes) were both observed to induce dacA gene transcription in comparison to non-treated bacteria. WT bacteria induced 1.5 and 4.5-fold higher transcription levels of dacA under the respective conditions, while the ΔmdrMTAC mutant induced 3 and 9-fold higher levels, respectively (FIG. 7A). To evaluate the influence of c-di-AMP production on *L. monocytogenes* growth under vancomycin stress, the dacA gene and pdeA (phosphodiesterase) gene were over-expressed in ΔmdrMTAC and WT bacteria from an IPTG inducible promoter (using the pLIV2 integrative plasmid) (Table 2). The over-expression of dacA and pdeA genes had only a moderate effect on the growth of WT bacteria in the presence of sub lethal concentration of vancomycin (1 μg ml$^{-1}$) (FIG. 7B), however the growth of the ΔmdrMTAC mutant under the same condition was seemingly altered upon over expression of these genes (FIG. 7C). Over-expression of the dacA gene suppressed the growth inhibition of ΔmdrMTAC by vancomycin, whereas over-expression of pdeA rendered it more susceptible to this drug (FIG. 7C). In accordance with these observations, an increase in cell wall thickness (by 17%) in the ΔmdrMTAC mutant over-expressing dacA was detected using TEM sections analysis (p value<0.001, based on 30 measurements). Notably, the effect of dacA and pdeA over-expression on the growth of WT bacteria was still moderate, even when the concentration of vancomycin was increased to further inhibit growth (FIGS. 12A-B). Furthermore, since over expression of dacA and pdeA genes had no effect on the growth of WT and ΔmdrMTAC bacteria in the absence of vancomycin stress (FIGS. 12C-D), it may be surmised that c-di-AMP and the MTAC transporters are both involved in the response to the vancomycin stress.

Lastly, the present inventors studied whether exogenous addition of purified c-di-AMP to bacterial cultures could recapitulate the phenotype observed with the dacA over-expressing bacteria. To this end WT and ΔmdrMTAC bacteria were grown in the presence of vancomycin (1 μg ml$^{-1}$) and purified c-di-AMP or c-di-GMP were added to the bacterial cultures. Notably, both ΔmdrMTAC and WT bacteria exhibited a shorter lag phase when c-di-AMP was added, whereas c-di-GMP addition had no effect (FIGS. 7D-E). Similarly to the dacA and pdeA over-expression experiments, c-di-AMP or c-di-GMP addition had no effect on the growth of the bacteria in the absence of vancomycin stress (FIGS. 12E-F). Together these results indicate a possible role for c-di-AMP in the response to vancomycin and further, hint at a physiological association between DacA, PdeA and the MDR transporters in mediating a response to this stress.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Dussurget O, Pizarro-Cerda J, Cossart P. 2004. Molecular determinants of *Listeria monocytogenes* virulence. Annu Rev Microbiol 58:587-610.
2. O'Riordan M, Yi C H, Gonzales R, Lee K D, Portnoy D A. 2002. Innate recognition of bacteria by a macrophage cytosolic surveillance pathway. Proc Natl Acad Sci USA 99:13861-13866.
3. Ishikawa H, Ma Z, Barber G N. 2009. STING regulates intracellular DNA-mediated, type I interferon-dependent innate immunity. Nature 461:788-792.
4. Perry A K, Chen G, Zheng D, Tang H, Cheng G. 2005. The host type I interferon response to viral and bacterial infections. Cell Res 15:407-422.
5. Stockinger S, Reutterer B, Schaljo B, Schellack C, Brunner S, Materna T, Yamamoto M, Akira S, Taniguchi T, Murray P J, Muller M, Decker T. 2004. IFN regulatory factor 3-dependent induction of type I IFNs by intracellular bacteria is mediated by a TLR- and Nod2-independent mechanism J Immunol 173:7416-7425.
6. O'Connell R M, Vaidya S A, Perry A K, Saha S K, Dempsey P W, Cheng G. 2005 Immune activation of type I IFNs by *Listeria monocytogenes* occurs independently of TLR4, TLR2, and receptor interacting protein 2 but involves TNFR-associated N F kappa B kinase-binding kinase 1. J Immunol 174:1602-1607.

7. Crimmins G T, Herskovits A A, Rehder K, Sivick K E, Lauer P, Dubensky T W, Jr., Portnoy D A. 2008. *Listeria monocytogenes* multidrug resistance transporters activate a cytosolic surveillance pathway of innate immunity. Proc Natl Acad Sci USA 105:10191-10196.

8. Brown M H, Skurray R A. 2001. Staphylococcal multidrug efflux protein QacA. J Mol Microbiol Biotechnol 3:163-170.

9. Nikaido H. 2009. Multidrug resistance in bacteria. Annu Rev Biochem 78:119-146.

10. Quillin S J, Schwartz K T, Leber J H. 2011. The novel *Listeria monocytogenes* bile sensor BrtA controls expression of the cholic acid efflux pump MdrT. Mol Microbiol 81:129-142.

11. Woodward J J, Iavarone A T, Portnoy D A. 2010. c-di-AMP secreted by intracellular *Listeria monocytogenes* activates a host type I interferon response. Science (New York, N.Y.) 328:1703-1705.

12. Yamamoto T, Hara H, Tsuchiya K, Sakai S, Fang R, Matsuura M, Nomura T, Sato F, Mitsuyama M, Kawamura I. 2012. *Listeria monocytogenes* strain-specific impairment of the TetR regulator underlies the drastic increase in cyclic di-AMP secretion and interferon beta-inducing ability. Infect Immun 13. Romling U. 2008. Great times for small molecules: c-di-AMP, a second messenger candidate in Bacteria and Archaea. Science signaling 1:pe39.

14. Oppenheimer-Shaanan Y, Wexselblatt E, Katzhendler J, Yavin E, Ben-Yehuda S. 2011. c-di-AMP reports DNA integrity during sporulation in *Bacillus subtilis*. EMB 0 reports 12:594-601.

15. Corrigan R M, Abbott J C, Burhenne H, Kaever V, Grundling A. 2011. c-di-AMP is a new second messenger in *Staphylococcus aureus* with a role in controlling cell size and envelope stress. PLoS pathogens 7:e1002217.

16. Luo Y, Heimann J D. 2012. Analysis of the role of *Bacillus subtilis* sigma(M) in beta-lactam resistance reveals an essential role for c-di-AMP in peptidoglycan homeostasis. Mol Microbiol 83:623-639.

17. Witte G, Hartung S, Buttner K, Hopfner K P. 2008. Structural biochemistry of a bacterial checkpoint protein reveals diadenylate cyclase activity regulated by DNA recombination intermediates. Molecular cell 30:167-178.

18. Witte C E, Whiteley A T, Burke T P, Sauer J D, Portnoy D A, Woodward J J. 2013. Cyclic di-AMP Is Critical for *Listeria monocytogenes* Growth, Cell Wall Homeostasis, and Establishment of Infection. mBio 4.

19. Wu J, Hassan K A, Skurray R A, Brown M H. 2008. Functional analyses reveal an important role for tyrosine residues in the staphylococcal multidrug efflux protein QacA. BMC Microbiol 8:147.

20. Nishino K, Yamaguchi A. 2001. Analysis of a complete library of putative drug transporter genes in *Escherichia coli*. J Bacteriol 183:5803-5812.

21. Lobel L, Sigal N, Borovok I, Ruppin E, Herskovits A A. 2012. Integrative genomic analysis identifies isoleucine and CodY as regulators of *Listeria monocytogenes* virulence. PLoS genetics 8:e1002887.

22. Ripio M T, Brehm K, Lara M, Suarez M, Vazquez-Boland J A. 1997. Glucose-1-phosphate utilization by *Listeria monocytogenes* is PrfA dependent and coordinately expressed with virulence factors. J Bacteriol 179: 7174-7180.

23. Cui L, Ma X, Sato K, Okuma K, Tenover F C, Mamizuka E M, Gemmell C G, Kim M N, Ploy M C, El-Solh N, Ferraz V, Hiramatsu K. 2003. Cell wall thickening is a common feature of vancomycin resistance in *Staphylococcus aureus*. J Clin Microbiol 41:5-14.

24. Kawai M, Yamada S, Ishidoshiro A, Oyamada Y, Ito H, Yamagishi J. 2009. Cell-wall thickness: possible mechanism of acriflavine resistance in meticillin-resistant *Staphylococcus aureus*. J Med Microbiol 58:331-336.

25. Corrigan R M, Campeotto I, Jeganathan T, Roelofs K G, Lee V T, Grundling A. 2013. Systematic identification of conserved bacterial c-di-AMP receptor proteins. Proc Natl Acad Sci USA 110:9084-9089.

26. Neyfakh A A. 1997. Natural functions of bacterial multidrug transporters. Trends Microbiol 5:309-313.

27. Piddock L J. 2006. Multidrug-resistance efflux pumps—not just for resistance. Nat Rev Microbiol 4:629-636.

28. Ren Q, Paulsen I T. 2007. Large-scale comparative genomic analyses of cytoplasmic membrane transport systems in prokaryotes. J Mol Microbiol Biotechnol 12:165-179.

29. Lewinson O, Adler J, Sigal N, Bibi E. 2006. Promiscuity in multidrug recognition and transport: the bacterial MFS Mdr transporters. Mol Microbiol 61:277-284.

30. Paulsen I T. 2003. Multidrug efflux pumps and resistance: regulation and evolution. Current opinion in microbiology 6:446-451.

31. Martinez J L, Sanchez M B, Martinez-Solano L, Hernandez A, Garmendia L, Fajardo A, Alvarez-Ortega C. 2009. Functional role of bacterial multidrug efflux pumps in microbial natural ecosystems. FEMS microbiology reviews 33:430-449.

32. Krulwich T A, Lewinson O, Padan E, Bibi E. 2005. Do physiological roles foster persistence of drug/multidrug-efflux transporters? A case study. Nat Rev Microbiol 3:566-572.

33. Hirakata Y, Srikumar R, Poole K, Gotoh N, Suematsu T, Kohno S, Kamihira S, Hancock R E, Speert D P. 2002. Multidrug efflux systems play an important role in the invasiveness of *Pseudomonas aeruginosa*. J Exp Med 196:109-118.

34. Nishino K, Latifi T, Groisman E A. 2006. Virulence and drug resistance roles of multidrug efflux systems of *Salmonella enterica* serovar *Typhimurium*. Mol Microbiol 59:126-141.

35. Evans K, Passador L, Srikumar R, Tsang E, Nezezon J, Poole K. 1998. Influence of the MexAB-OprM multidrug efflux system on quorum sensing in *Pseudomonas aeruginosa*. J Bacteriol 180:5443-5447.

36. Lee E H, Shafer W M. 1999. The farAB-encoded efflux pump mediates resistance of gonococci to long-chained antibacterial fatty acids. Mol Microbiol 33:839-845.

37. Lewinson O, Padan E, Bibi E. 2004. Alkalitolerance: a biological function for a multidrug transporter in pH homeostasis. Proc Natl Acad Sci USA 101:14073-14078.

38. Lacroix F J, Cloeckaert A, Grepinet O, Pinault C, Popoff M Y, Waxin H, Pardon P. 1996. *Salmonella typhimurium* acrB-like gene: identification and role in resistance to biliary salts and detergents and in murine infection. FEMS Microbiol Lett 135:161-167.

39. Thanassi D G, Cheng L W, Nikaido H. 1997. Active efflux of bile salts by *Escherichia coli*. J Bacteriol 179: 2512-2518.

40. Bengoechea J A, Skurnik M. 2000. Temperature-regulated efflux pump/potassium antiporter system mediates resistance to cationic antimicrobial peptides in *Yersinia*. Mol Microbiol 37:67-80.

41. Pearson J P, Van Delden C, Iglewski B H. 1999. Active efflux and diffusion are involved in transport of *Pseudomonas aeruginosa* cell-to-cell signals. J Bacteriol 181:1203-1210.
42. Aendekerk S, Diggle S P, Song Z, Hoiby N, Cornelis P, Williams P, Camara M. 2005. The MexGHI-OpmD multidrug efflux pump controls growth, antibiotic susceptibility and virulence in *Pseudomonas aeruginosa* via 4-quinolone-dependent cell-to-cell communication. Microbiology 151:1113-1125.
43. Rao F, See R Y, Zhang D, Toh D C, Ji Q, Liang Z X. 2010. YybT is a signaling protein that contains a cyclic dinucleotide phosphodiesterase domain and a GGDEF domain with ATPase activity. J Biol Chem 285:473-482.
44. Zhang L, Li W, He Z G. 2013. DarR, a TetR-like transcriptional factor, is a cyclic di-AMP-responsive repressor in *Mycobacterium smegmatis*. J Biol Chem 288:3085-3096.
45. Banerjee R, Gretes M, Harlem C, Basuino L, Chambers H F. 2010. A mecA-negative strain of methicillin-resistant *Staphylococcus aureus* with high-level beta-lactam resistance contains mutations in three genes. Antimicrob Agents Chemother 54:4900-4902.
46. Gomelsky M. 2011. cAMP, c-di-GMP, c-di-AMP and now cGMP: bacteria use them all! Mol Microbiol 79:562-565.
47. Hengge R. 2009. Principles of c-di-GMP signalling in bacteria. Nat Rev Microbiol 7:263-273.
48. Simon R, Priefer U, Puhler A. 1983. A Broad Host Range Mobilization System for In Vivo Genetic Engineering: Transposon Mutagenesis in Gram Negative Bacteria. Nat Biotech 1:784-791.
49. Phan-Thanh L, Gormon T. 1997. A chemically defined minimal medium for the optimal culture of *Listeria*. Int J Food Microbiol 35:91-95.
50. Portnoy D A, Schreiber R D, Connelly P, Tilney L G. 1989. Gamma interferon limits access of *Listeria monocytogenes* to the macrophage cytoplasm. J Exp Med 170:2141-2146.
51. Herskovits A A, Auerbuch V, Portnoy D A. 2007. Bacterial ligands generated in a phagosome are targets of the cytosolic innate immune system. PLoS pathogens 3:e51.
52. Vidal-Aroca F, Giannattasio M, Brunetti E, Vezzoli A, Plevani P, Muzi-Falconi M, Bertoni G. 2006. One-step high-throughput assay for quantitative detection of beta-galactosidase activity in intact gram-negative bacteria, yeast, and mammalian cells. BioTechniques 40:433-434, 436, 438 passim.
53. Chanda P K, Ganguly T, Das M, Lee C Y, Luong T T, Sau S. 2007. Detection of antistaphylococcal and toxic compounds by biological assay systems developed with a reporter *Staphylococcus aureus* strain harboring a heat inducible promoter—lacZ transcriptional fusion. Journal of biochemistry and molecular biology 40:936-943.
54. Girardin S E, Boneca I G, Viala J, Chamaillard M, Labigne A, Thomas G, Philpott D J, Sansonetti P J. 2003. Nod2 is a general sensor of peptidoglycan through muramyl dipeptide (MDP) detection. J Biol Chem 278: 8869-8872.
55. Boneca I G, Dussurget O, Cabanes D, Nahori M A, Sousa S, Lecuit M, Psylinakis E, Bouriotis V, Hugot J P, Giovannini M, Coyle A, Bertin J, Namane A, Rousselle J C, Cayet N, Prevost M C, Balloy V, Chignard M, Philpott D J, Cossart P, Girardin S E. 2007. A critical role for peptidoglycan N-deacetylation in *Listeria* evasion from the host innate immune system. Proc Natl Acad Sci USA 104:997-1002.
56. Aubry C, Goulard C, Nahori M A, Cayet N, Decalf J, Sachse M, Boneca I G, Cossart P, Dussurget O. 2011. OatA, a peptidoglycan O-acetyltransferase involved in *Listeria monocytogenes* immune escape, is critical for virulence. The Journal of infectious diseases 204:731-740.

---

What is claimed is:

1. A *Listeria monocytogenes* bacterium comprising a first mutation in the multidrug resistance transporter M (MdrM) gene having the gene ID: 12553832, a second mutation in the multidrug resistance transporter T (MdrT) gene having the gene ID: 12554851 and at least one additional mutation in a multidrug resistance transporter gene selected from the group consisting of MdrA gene having the gene ID: 12552738, MdrB gene having the gene ID: 12555124, MdrC gene having the gene ID: 12555097, MdrE gene having the gene ID: 12555105, wherein said *Listeria monocytogenes* bacterium which comprises said first mutation, said second mutation and said at least one additional mutation decreases interferon-β production in macrophages as compared to wild-type *Listeria monocytogenes* bacterium as measured by PCR.

2. The *Listeria monocytogenes* bacterium of claim 1, wherein the *Listeria monocytogenes* bacterium which comprises said first mutation, said second mutation and said at least one additional mutation decreases interferon-β production in macrophages as compared to a *Listeria monocytogenes* bacterium having said first mutation in said MdrM gene, but not having said second mutation in said MdrT gene and said at least one additional mutation in said multidrug resistance transporter gene selected from the group consisting of the MdrA gene, the MdrB gene, the MdrC gene, the MdrD gene, and the MdrE gene.

3. The *Listeria monocytogenes* bacterium of claim 1, wherein the *Listeria monocytogenes* bacterium which comprises said first mutation, said second mutation and said at least one additional mutation decreases interferon-β production in macrophages as compared to a *Listeria monocytogenes* bacterium having said second mutation in said MdrT gene, but not having said first mutation in said MdrM gene and said multidrug resistance transporter gene selected from the group consisting of the MdrA gene, the MdrB gene, the MdrC gene, the MdrD gene, and the MdrE gene.

4. The *Listeria monocytogenes* bacterium of claim 1, wherein said at least one additional mutation in the multidrug resistance transporter gene is selected from the group consisting of said MdrA gene and said MdrC gene.

5. The *Listeria monocytogenes* bacterium of claim 1, wherein said at least one additional mutation in a multidrug resistance transporter gene is in said MdrA gene and in said MdrC gene.

6. The *Listeria monocytogenes* bacterium of claim 1, wherein said at least one additional mutation in a multidrug resistance transporter gene is in said MdrA gene, said MdrC gene and said MdrB gene.

7. The *Listeria monocytogenes* bacterium of claim 1, wherein said mutation is a deletion mutation.

8. The *Listeria monocytogenes* bacterium of claim 1, wherein said first mutation is a point mutation.

9. The *Listeria monocytogenes* bacterium of claim 8, wherein said point mutation is a phenylalanine to valine substitution at position 58.

10. The *Listeria monocytogenes* bacterium of claim 8, wherein said point mutation is in the substrate binding pocket of said multidrug resistance transporter M gene.

11. The *Listeria monocytogenes* bacterium of claim 8, wherein said point mutation is effected at the residues W49, W141, W166 and F58.

12. The *Listeria monocytogenes* bacterium according to claim 1, wherein said *Listeria monocytogenes* bacterium is attenuated.

13. The *Listeria monocytogenes* bacterium of claim 1, further comprising a heterologous nucleic acid.

14. The *Listeria monocytogenes* bacterium according to claim 13, wherein said heterologous nucleic acid is integrated into the *Listeria monocytogenes* chromosome.

15. The *Listeria monocytogenes* bacterium according to claim 13, wherein said heterologous nucleic acid encodes at least one polypeptide.

16. A vaccine comprising the *Listeria monocytogenes* bacterium of claim 1.

17. A method of eliciting or boosting a cellular immune response in a mammalian subject comprising administering to said subject an effective amount of the vaccine of claim 16, thereby eliciting or boosting the cellular immune response in said subject.

18. An article of manufacture comprising the *Listeria monocytogenes* bacterium of claim 1 and an immunogen.

* * * * *

SEQUENCE LISTING

```
<160> NUMBER OF SEQ ID NOS: 69

<210> SEQ ID NO 1
<211> LENGTH: 1464
<212> TYPE: DNA
<213> ORGANISM: Listeria monocytogenes

<400> SEQUENCE: 1
atgaaagcag caagtacatc agtgaagcgt aacggtattt tgattgttat gcttatgggc      60
gcctttgtta ccattctcaa ccaaacgttg atgaatgtcg cgctaccaag tattatgaaa     120
gattttggaa ttacagccag tcaaggacaa tggttatcaa ctggatttat gttagttaat     180
ggtgtcatga ttccaatgac ggccttttta attgaacgat ttacaacgcg tcagctttac     240
ttattcgcga tgattacctt tgcgattggt acagcaattg gcggattcgc cacagattat     300
accatgctga ttgctgggcg tatggtacaa gcaattggtg ctgggattgt tatgccactt     360
cttacagttg tggtattaaa cttattcccg atggaacgaa gagggcgagc gatgggctta     420
attggtcttg ctatgaactt tgccccagca attggtccga cactttcagg ttggattgtt     480
caacaatatg attggcgcaa tttattcttt attattattc cgttcgcgat tcttgatatt     540
gtcgtagcga ttttcttact taaaaatgtc ggaaaaagaa ctttcccgaa actcgacgtc     600
cttggggtta tcatgtcaac agttgggttt ggtagttat tactaggatt tagtaatgct     660
```

```
ggagaccatg attggttaac ttggaaagta gctggattta ttattcttgg tctagtagtg    720
ctaggaatat ttatccgtta tcaaacaagc aacaaagcgc cactgcttaa ctttagagta    780
tttaaatatc ctacatttgc acttacaaca gcaattagtt tctttgtggt aatgggactt    840
tttggcggca tgttattact accaattttc ttcaaacag ttagaggatt ttcacctttg     900
gaatctggat tagttctctt gccaggtgca ctcgtcacgg cgatactttc gcctgtaaca    960
ggggtaatgt ttgaccgttt tggggctaaa tatttatcac ttgtcggctt gattattatg   1020
gcgggatcga ctttcatgtt tacaaatttg gatgaatcca ctacgttaac ttttattatt   1080
atcgtacaaa cgattcgttc tgcagggatg gcgatggtca tgatgccgct acaaacagct   1140
gcccttaatt cacttccatt aaaactagca tcccacggtt cagcgatgtt taacactatg   1200
cgtcaagttg ctggttcaat cgggacagct gcacttataa ccgtcatgtc taagagcgca   1260
gcaagttttg ccactaaact cggaccagct gatgtcattg gcaaaactaa aactgatatt   1320
gccaaccatg tcctcatcca cggaatagaa accgcctttt tagtagcggg aattctttct   1380
gtagtcgctt gtgttctagc actatttata caaaaaaata gaagtgccat ggatccaatt   1440
gttactaaaa cggaaaaagc ataa                                          1464
```

<210> SEQ ID NO 2
<211> LENGTH: 487
<212> TYPE: PRT
<213> ORGANISM: Listeria monocytogenes

<400> SEQUENCE: 2

```
Met Lys Ala Ala Ser Thr Ser Val Lys Arg Asn Gly Ile Leu Ile Val
1               5                   10                  15

Met Leu Met Gly Ala Phe Val Thr Ile Leu Asn Gln Thr Leu Met Asn
            20                  25                  30

Val Ala Leu Pro Ser Ile Met Lys Asp Phe Gly Ile Thr Ala Ser Gln
        35                  40                  45

Gly Gln Trp Leu Ser Thr Gly Phe Met Leu Val Asn Gly Val Met Ile
    50                  55                  60

Pro Met Thr Ala Phe Leu Ile Glu Arg Phe Thr Thr Arg Gln Leu Tyr
65                  70                  75                  80

Leu Phe Ala Met Ile Thr Phe Ala Ile Gly Thr Ala Ile Gly Phe
                85                  90                  95

Ala Thr Asp Tyr Thr Met Leu Ile Ala Gly Arg Met Val Gln Ala Ile
            100                 105                 110

Gly Ala Gly Ile Val Met Pro Leu Leu Thr Val Val Leu Asn Leu
        115                 120                 125

Phe Pro Met Glu Arg Arg Gly Arg Ala Met Gly Leu Ile Gly Leu Ala
    130                 135                 140

Met Asn Phe Ala Pro Ala Ile Gly Pro Thr Leu Ser Gly Trp Ile Val
145                 150                 155                 160

Gln Gln Tyr Asp Trp Arg Asn Leu Phe Ile Ile Pro Phe Ala
                165                 170                 175

Ile Leu Asp Ile Val Val Ala Ile Phe Leu Leu Lys Asn Val Gly Lys
            180                 185                 190

Arg Thr Phe Pro Lys Leu Asp Val Leu Gly Val Ile Met Ser Thr Val
        195                 200                 205

Gly Phe Gly Ser Leu Leu Leu Gly Phe Ser Asn Ala Gly Asp His Asp
    210                 215                 220

Trp Leu Thr Trp Lys Val Ala Gly Phe Ile Ile Leu Gly Leu Val Val
```

```
                225                 230                 235                 240
Leu Gly Ile Phe Ile Arg Tyr Gln Thr Ser Asn Lys Ala Pro Leu Leu
                245                 250                 255

Asn Phe Arg Val Phe Lys Tyr Pro Thr Phe Ala Leu Thr Thr Ala Ile
            260                 265                 270

Ser Phe Val Val Met Gly Leu Phe Gly Met Leu Leu Pro
        275                 280                 285

Ile Phe Leu Gln Thr Val Arg Gly Phe Ser Pro Leu Glu Ser Gly Leu
        290                 295                 300

Val Leu Leu Pro Gly Ala Leu Val Thr Ala Ile Leu Ser Pro Val Thr
305                 310                 315                 320

Gly Val Met Phe Asp Arg Phe Gly Ala Lys Tyr Leu Ser Leu Val Gly
                325                 330                 335

Leu Ile Ile Met Ala Gly Ser Thr Phe Met Phe Thr Asn Leu Asp Glu
            340                 345                 350

Ser Thr Thr Leu Thr Phe Ile Ile Val Gln Thr Ile Arg Ser Ala
        355                 360                 365

Gly Met Ala Met Val Met Met Pro Leu Gln Thr Ala Ala Leu Asn Ser
    370                 375                 380

Leu Pro Leu Lys Leu Ala Ser His Gly Ser Ala Met Phe Asn Thr Met
385                 390                 395                 400

Arg Gln Val Ala Gly Ser Ile Gly Thr Ala Ala Leu Ile Thr Val Met
                405                 410                 415

Ser Lys Ser Ala Ala Ser Phe Ala Thr Lys Leu Gly Pro Ala Asp Val
            420                 425                 430

Ile Gly Lys Thr Lys Thr Asp Ile Ala Asn His Val Leu Ile His Gly
        435                 440                 445

Ile Glu Thr Ala Phe Leu Val Ala Gly Ile Leu Ser Val Val Ala Cys
    450                 455                 460

Val Leu Ala Leu Phe Ile Gln Lys Asn Arg Ser Ala Met Asp Pro Ile
465                 470                 475                 480

Val Thr Lys Thr Glu Lys Ala
            485

<210> SEQ ID NO 3
<211> LENGTH: 1482
<212> TYPE: DNA
<213> ORGANISM: Listeria monocytogenes

<400> SEQUENCE: 3
ttgaatagta cagcagtaga acagcctgtt gatgttaacg ggaaatctta tagtagaagt      60
ttattagtag taacaatgat tattggggca tttgtagcga ttttgaatca gacgttatta    120
gcgacggcgc taccaatgat tatggatgat ttgcatatta cagcagcaac agggcaatgg    180
ttaacgacag ctttcttgct gacaaatggg attatgattc caattacagc acttttaatt    240
gaaaaaatta gttcgaaaac gttatttatt acggcgatga ctgtatttac aattggtaca    300
attattgcat ctgtggcggg ttcattcccg atcttgctta ctggtcgtat tgttcaagcg    360
gcgggtgcgg ggattatgat gccattactt caaacaatct tcttgctaat tttcccgcgt    420
gaaaaacgtg gggcggcaat ggggctgatg ggactcgtta ttgcgtttgc tccagcaatt    480
gggccaactt tgtctggttg gattgtggat tcgtatgatt ggcgcgtatt atttcttatt    540
ttaattccaa tcgcggttat cgatataatt ctagcgttct ttggaatgaa aaaagtagtg    600
aagttaactg atacaaaaat tgattttctt tctattgtaa tgtcttcgat tggttttggg    660
```

```
gcattgctat acggatttag ttcagcgggt aatgatggtt ggggagatac aacggttatc    720
acgatgttga ttgttggtgt cgttgttatt gcactatttg tttggcgcca actagttatt    780
gataatccga tgcttgaact acatgtgttt aaatatccgg tattttcatt gtctgttatt    840
cttggttcaa ttgtaacaat ggcaatgatt ggtgcggaaa ttgtgttacc actttatatt    900
caaacaattc gcggggagtc ggcgcttcaa tcaggtctat tattacttcc gggtgcgatt    960
attatgggga taatgagtcc aattacgggt attattttcg ataaaattgg ggcgaaatgg   1020
ttgacgatta ccggggttac cattttgact atcggtacaa ttccatttat gttcttaacg   1080
atggatacgc cactttggta tattgtagta ttttatgccg tgcggttctt cggtatttca   1140
atggcaatga tgccagtttc gacagcgggt atgaatgcac ttcctaacca cttgattaac   1200
cacggttcgg cagtaaataa tacgattcga caaattgctg gttcaatcgg gactgcggta   1260
cttattactg ttttaacgaa tgtaaccaaa gacaatatgc caggaaaagc gcttatggcg   1320
acggatcctg ctagttttgc tcaaaaagcg caagatgcta gtttggacgg aatgcgtgcg   1380
gcgtttatgg ttgcagcgat ttttgcggct attgggatga tcttaagttt attcctaaaa   1440
accaagaaac aagagccaat cgtcaaagaa tatacgaaat aa                      1482

<210> SEQ ID NO 4
<211> LENGTH: 493
<212> TYPE: PRT
<213> ORGANISM: Listeria monocytogenes

<400> SEQUENCE: 4

Met Asn Ser Thr Ala Val Glu Gln Pro Val Asp Val Asn Gly Lys Ser
1               5                   10                  15

Tyr Ser Arg Ser Leu Leu Val Val Thr Met Ile Ile Gly Ala Phe Val
            20                  25                  30

Ala Ile Leu Asn Gln Thr Leu Leu Ala Thr Ala Leu Pro Met Ile Met
        35                  40                  45

Asp Asp Leu His Ile Thr Ala Ala Thr Gly Gln Trp Leu Thr Thr Ala
    50                  55                  60

Phe Leu Leu Thr Asn Gly Ile Met Ile Pro Ile Thr Ala Leu Leu Ile
65                  70                  75                  80

Glu Lys Ile Ser Ser Lys Thr Leu Phe Ile Thr Ala Met Thr Val Phe
                85                  90                  95

Thr Ile Gly Thr Ile Ile Ala Ser Val Ala Gly Ser Phe Pro Ile Leu
            100                 105                 110

Leu Thr Gly Arg Ile Val Gln Ala Gly Ala Gly Ile Met Met Pro
            115                 120                 125

Leu Leu Gln Thr Ile Phe Leu Leu Ile Phe Pro Arg Glu Lys Arg Gly
    130                 135                 140

Ala Ala Met Gly Leu Met Gly Leu Val Ile Ala Phe Ala Pro Ala Ile
145                 150                 155                 160

Gly Pro Thr Leu Ser Gly Trp Ile Val Asp Ser Tyr Asp Trp Arg Val
                165                 170                 175

Leu Phe Leu Ile Leu Ile Pro Ile Ala Val Ile Asp Ile Ile Leu Ala
            180                 185                 190

Phe Phe Gly Met Lys Lys Val Val Lys Leu Thr Asp Thr Lys Ile Asp
        195                 200                 205

Phe Leu Ser Ile Val Met Ser Ser Ile Gly Phe Gly Ala Leu Leu Tyr
    210                 215                 220
```

```
Gly Phe Ser Ser Ala Gly Asn Asp Gly Trp Gly Asp Thr Thr Val Ile
225                 230                 235                 240

Thr Met Leu Ile Val Gly Val Val Ile Ala Leu Phe Val Trp Arg
            245                 250                 255

Gln Leu Val Ile Asp Asn Pro Met Leu Glu Leu His Val Phe Lys Tyr
                260                 265                 270

Pro Val Phe Ser Leu Ser Val Ile Leu Gly Ser Ile Val Thr Met Ala
            275                 280                 285

Met Ile Gly Ala Glu Ile Val Leu Pro Leu Tyr Ile Gln Thr Ile Arg
290                 295                 300

Gly Glu Ser Ala Leu Gln Ser Gly Leu Leu Leu Pro Gly Ala Ile
305                 310                 315                 320

Ile Met Gly Ile Met Ser Pro Ile Thr Gly Ile Ile Phe Asp Lys Ile
                325                 330                 335

Gly Ala Lys Trp Leu Thr Ile Thr Gly Val Thr Ile Leu Thr Ile Gly
            340                 345                 350

Thr Ile Pro Phe Met Phe Leu Thr Met Asp Thr Pro Leu Trp Tyr Ile
        355                 360                 365

Val Val Phe Tyr Ala Val Arg Phe Phe Gly Ile Ser Met Ala Met Met
370                 375                 380

Pro Val Ser Thr Ala Gly Met Asn Ala Leu Pro Asn His Leu Ile Asn
385                 390                 395                 400

His Gly Ser Ala Val Asn Asn Thr Ile Arg Gln Ile Ala Gly Ser Ile
                405                 410                 415

Gly Thr Ala Val Leu Ile Thr Val Leu Thr Asn Val Thr Lys Asp Asn
            420                 425                 430

Met Pro Gly Lys Ala Leu Met Ala Thr Asp Pro Ala Ser Phe Ala Gln
        435                 440                 445

Lys Ala Gln Asp Ala Ser Leu Asp Gly Met Arg Ala Ala Phe Met Val
            450                 455                 460

Ala Ala Ile Phe Ala Ala Ile Gly Met Ile Leu Ser Leu Phe Leu Lys
465                 470                 475                 480

Thr Lys Lys Gln Glu Pro Ile Val Lys Glu Tyr Thr Lys
            485                 490
```

<210> SEQ ID NO 5
<211> LENGTH: 1416
<212> TYPE: DNA
<213> ORGANISM: Listeria monocytogenes

<400> SEQUENCE: 5

```
atgcaacaag aagcaacagg tgggcagaaa attcggccga taccgattat tgcctcattt      60
ttgatggcgg ggtcattgg gctattcagt gaaactgctc ttaacatggc gcttagtgat     120
ttgattcagg tgtttgatat tagttcagcg acagtgcagt ggcttacgac aggttatttg     180
ctaacgcttg gaatattagt accgatttcg ggattacttt acaatggtt tacgacacga     240
ggtttatttt ttacagcagt gagttttcg attgctggta cgctcattgc ggcgctttcg     300
ccaacgtttg cgatgttaat gattggacgt gtagtgcaag cagtaggtac ggcgctatta     360
ctaccgttaa tgtttaacac gattttactg attttcccag agcataaacg tggctcagca     420
atggggatga tcgggctggt aattatgttt gcaccagcag ttggtccgac gatttcagga     480
cttatttag aaaacttgac ttggaactgg attttctgga tttccttgcc attccttatt     540
attgcgttat tattcggaat gaaatttatg caaaatgttt cggttgttac gaagccgaaa     600
```

```
attgatattt tatcgattat cctttcgacg ctaggttttg gtggagttgt atttgccttt      660
agtagtgcgg gcgaaagtgg ttggggaagc gcgacggtat tagtttcaat tatcgttggt      720
ggacttgcgc ttggactttt tgtttggcgc caactaacaa tggaaaaacc tttgatggac      780
ttgaaagtat ttagataccc aatgttcaca ttaggactta ttttagtatt tatcagcttt      840
atgatgattc tttcaacgat gatttactac cgctttact tgcaaaatag tttagcgctc      900
gcagcatttt cagcgggatt agtattactt ccgggtgggg tgctgaatgg tttaatgtca      960
ccatttactg ggcgtttgtt cgatgcatac ggtccacgcg cacttgttat cccagggttt     1020
atcgtagcgg ttgtggcact attttttctta acgagaatag aagttgggac atctgcatta     1080
accatcatcg tgcttcattc ggtgttaatg attgggattt cgatggtcat gatgccggca     1140
caaacaaacg gattaaacca attaccgcca aaattatatc ctgatggcac ggcgattatg     1200
aacacgttgc aacaagtttc cggcgcgatt ggaacggctg ttgcgattac gatcatgtca     1260
gctggacaaa aagcttatat ggaaacggcg caaggagtag gaccggagca aatggttgct     1320
tcactgacag caggaattca aaatgccttt gtctttggac tgattatggc ttgtattggt     1380
ctgctgtgtt cgctatttat tcgtaaagct aaataa                                1416
```

<210> SEQ ID NO 6
<211> LENGTH: 471
<212> TYPE: PRT
<213> ORGANISM: Listeria monocytogenes

<400> SEQUENCE: 6

```
Met Gln Gln Glu Ala Thr Gly Gly Gln Lys Ile Arg Pro Ile Pro Ile
1               5                   10                  15

Ile Ala Ser Phe Leu Met Ala Gly Phe Ile Gly Leu Phe Ser Glu Thr
            20                  25                  30

Ala Leu Asn Met Ala Leu Ser Asp Leu Ile Gln Val Phe Asp Ile Ser
        35                  40                  45

Ser Ala Thr Val Gln Trp Leu Thr Thr Gly Tyr Leu Leu Thr Leu Gly
    50                  55                  60

Ile Leu Val Pro Ile Ser Gly Leu Leu Leu Gln Trp Phe Thr Thr Arg
65                  70                  75                  80

Gly Leu Phe Phe Thr Ala Val Ser Phe Ser Ile Ala Gly Thr Leu Ile
                85                  90                  95

Ala Ala Leu Ser Pro Thr Phe Ala Met Leu Met Ile Gly Arg Val Val
            100                 105                 110

Gln Ala Val Gly Thr Ala Leu Leu Leu Pro Leu Met Phe Asn Thr Ile
        115                 120                 125

Leu Leu Ile Phe Pro Glu His Lys Arg Gly Ser Ala Met Gly Met Ile
    130                 135                 140

Gly Leu Val Ile Met Phe Ala Pro Ala Val Gly Pro Thr Ile Ser Gly
145                 150                 155                 160

Leu Ile Leu Glu Asn Leu Thr Trp Asn Trp Ile Phe Trp Ile Ser Leu
                165                 170                 175

Pro Phe Leu Ile Ile Ala Leu Leu Phe Gly Met Lys Phe Met Gln Asn
            180                 185                 190

Val Ser Val Thr Lys Pro Lys Ile Asp Ile Leu Ser Ile Ile Leu
        195                 200                 205

Ser Thr Leu Gly Phe Gly Gly Val Val Phe Ala Phe Ser Ser Ala Gly
    210                 215                 220

Glu Ser Gly Trp Gly Ser Ala Thr Val Leu Val Ser Ile Ile Val Gly
```

```
                225                 230                 235                 240
       Gly Leu Ala Leu Gly Leu Phe Val Trp Arg Gln Leu Thr Met Glu Lys
                           245                 250                 255

Pro Leu Met Asp Leu Lys Val Phe Arg Tyr Pro Met Phe Thr Leu Gly
                   260                 265                 270

Leu Ile Leu Val Phe Ile Ser Phe Met Met Ile Leu Ser Thr Met Ile
                   275                 280                 285

Leu Leu Pro Leu Tyr Leu Gln Asn Ser Leu Ala Leu Ala Ala Phe Ser
               290                 295                 300

Ala Gly Leu Val Leu Leu Pro Gly Gly Val Leu Asn Gly Leu Met Ser
       305                 310                 315                 320

Pro Phe Thr Gly Arg Leu Phe Asp Ala Tyr Gly Pro Arg Ala Leu Val
                           325                 330                 335

Ile Pro Gly Phe Ile Val Ala Val Val Ala Leu Phe Phe Leu Thr Arg
                       340                 345                 350

Ile Glu Val Gly Thr Ser Ala Leu Thr Ile Ile Val Leu His Ser Val
                   355                 360                 365

Leu Met Ile Gly Ile Ser Met Val Met Met Pro Ala Gln Thr Asn Gly
               370                 375                 380

Leu Asn Gln Leu Pro Pro Lys Leu Tyr Pro Asp Gly Thr Ala Ile Met
       385                 390                 395                 400

Asn Thr Leu Gln Gln Val Ser Gly Ala Ile Gly Thr Ala Val Ala Ile
                           405                 410                 415

Thr Ile Met Ser Ala Gly Gln Lys Ala Tyr Met Glu Thr Ala Gln Gly
                       420                 425                 430

Val Gly Pro Glu Gln Met Val Ala Ser Leu Thr Ala Gly Ile Gln Asn
                   435                 440                 445

Ala Phe Val Phe Gly Leu Ile Met Ala Cys Ile Gly Leu Leu Cys Ser
               450                 455                 460

Leu Phe Ile Arg Lys Ala Lys
       465                 470

<210> SEQ ID NO 7
<211> LENGTH: 1413
<212> TYPE: DNA
<213> ORGANISM: Listeria monocytogenes

<400> SEQUENCE: 7
atggaacaga cgaataaacg taatacttta gcacttattt caattatgct tggagctttt      60
atttcattat tagatacaac aatcgttaat gtggccttgc ctgatattac gacggcccta     120
catgcgacaa gcgagacgat tgagtgggta atttcaggct atgcgcttgc ttttgggctt     180
gtacttattt tagctggtcg acttgggggat aaatttggcc gaaaaaacat ctacattatc     240
gggattacgc tatttctaat tatgagtgtg acagctggtt ttgcagattc agaaaatagt     300
ctaattattt cccgggtaat acaaggactt gctgccggat tattttttccc gcaaatcaac     360 gccacaatta tggatatgta ttctgggaaa agccttggga aatcttcgg aattcttggc     420 tctgttattg gtgtaggaac tgccatcgga cctcttacag gaggacttttt aattgaactg     480 ttcggagcta caaatggttg gcgcgcagtt ttcttcgtta acgtaccttt tgtgttagta     540
acgctcgtcc tagcaatgct ttatcttccc aaaagaactg tttccacgaa aaaaatcagc     600
ttcgatttac ctggagttgg gctactgaca attgcactct tactattact tttcccactt     660
atttcaaatg gtgcaaatga tttcaaacca gtggattact ttttaatggc gctatctatt     720
```

-continued

```
ccactatttta ttattctttta taaatggagc gtctaccaag aaaagaaagg aaatcagcca      780
ttaattgcac ctaatcttct taaaaacaat caatttgttt caggtatgct cttatcgctt      840
gtttactttg ctgcttttac aagtattttc tttgtcctat ctctaacttg gcaaactggc      900
ttcgaccggt ctgctatttt atctggactt gctattagtc cttttgcatt aggtagtgtg      960
ctcgccgcat ctaatagtta ccggcttatt ccactactcg aagaaaaact cttaatgctt     1020
ggagtcacac tcgttattgt cggtcttggc accgtgtcta ttgttttcca tttgaacgac     1080
ggcgctttct ctgcttggct tttattctta ccctcttca tcgctggcat tggtagtggt     1140
ttgactattg caccattgaa tagttttacc ctttccactg tgactggtat agatcgcggt     1200
ggagctagtg gtatgtttaa tacagcgcag cgaattggtt cgtcctttgg gattgctgtt     1260
gttggctcag tcttcttccg cacacttgga aatactgcca ctacttcaaa agcaagcgcc     1320
ttttccgaca gtttgcaaat gagcatgtat gtcaatattg ttctacttgt tgtttgtttc     1380
ctacttgtat tccggttacc gaaaaatatt taa                                  1413
```

<210> SEQ ID NO 8
<211> LENGTH: 470
<212> TYPE: PRT
<213> ORGANISM: Listeria monocytogenes

<400> SEQUENCE: 8

```
Met Glu Gln Thr Asn Lys Arg Asn Thr Leu Ala Leu Ile Ser Ile Met
1               5                   10                  15

Leu Gly Ala Phe Ile Ser Leu Leu Asp Thr Thr Ile Val Asn Val Ala
            20                  25                  30

Leu Pro Asp Ile Thr Thr Ala Leu His Ala Thr Ser Glu Thr Ile Glu
        35                  40                  45

Trp Val Ile Ser Gly Tyr Ala Leu Ala Phe Gly Leu Val Leu Ile Leu
    50                  55                  60

Ala Gly Arg Leu Gly Asp Lys Phe Gly Arg Lys Asn Ile Tyr Ile Ile
65                  70                  75                  80

Gly Ile Thr Leu Phe Leu Ile Met Ser Val Thr Ala Gly Phe Ala Asp
                85                  90                  95

Ser Glu Asn Ser Leu Ile Ile Ser Arg Val Ile Gln Gly Leu Ala Ala
            100                 105                 110

Gly Leu Phe Phe Pro Gln Ile Asn Ala Thr Ile Met Asp Met Tyr Ser
        115                 120                 125

Gly Lys Ser Leu Gly Lys Ile Phe Gly Ile Leu Gly Ser Val Ile Gly
    130                 135                 140

Val Gly Thr Ala Ile Gly Pro Leu Thr Gly Gly Leu Leu Ile Glu Leu
145                 150                 155                 160

Phe Gly Ala Thr Asn Gly Trp Arg Ala Val Phe Phe Val Asn Val Pro
                165                 170                 175

Phe Val Leu Val Thr Leu Val Leu Ala Met Leu Tyr Leu Pro Lys Arg
            180                 185                 190

Thr Val Ser Thr Lys Lys Ile Ser Phe Asp Leu Pro Gly Val Gly Leu
        195                 200                 205

Leu Thr Ile Ala Leu Leu Leu Leu Phe Pro Leu Ile Ser Asn Gly
    210                 215                 220

Ala Asn Asp Phe Lys Pro Val Asp Tyr Phe Leu Met Ala Leu Ser Ile
225                 230                 235                 240

Pro Leu Phe Ile Ile Leu Tyr Lys Trp Ser Val Tyr Gln Glu Lys Lys
                245                 250                 255
```

```
Gly Asn Gln Pro Leu Ile Ala Pro Asn Leu Leu Lys Asn Asn Gln Phe
            260                 265                 270

Val Ser Gly Met Leu Leu Ser Leu Val Tyr Phe Ala Ala Phe Thr Ser
            275                 280                 285

Ile Phe Phe Val Leu Ser Leu Thr Trp Gln Thr Gly Phe Asp Arg Ser
290                 295                 300

Ala Ile Leu Ser Gly Leu Ala Ile Ser Pro Phe Ala Leu Gly Ser Val
305                 310                 315                 320

Leu Ala Ala Ser Asn Ser Tyr Arg Leu Ile Pro Leu Leu Gly Arg Lys
                325                 330                 335

Leu Leu Met Leu Gly Val Thr Leu Val Ile Val Gly Leu Gly Thr Val
            340                 345                 350

Ser Ile Val Phe His Leu Asn Asp Gly Ala Phe Ser Ala Trp Leu Leu
            355                 360                 365

Phe Leu Pro Leu Phe Ile Ala Gly Ile Gly Ser Gly Leu Thr Ile Ala
        370                 375                 380

Pro Leu Asn Ser Phe Thr Leu Ser Thr Val Thr Gly Ile Asp Arg Gly
385                 390                 395                 400

Gly Ala Ser Gly Met Phe Asn Thr Ala Gln Arg Ile Gly Ser Ser Phe
            405                 410                 415

Gly Ile Ala Val Val Gly Ser Val Phe Phe Arg Thr Leu Gly Asn Thr
            420                 425                 430

Ala Thr Thr Ser Lys Ala Ser Ala Phe Ser Asp Ser Leu Gln Met Ser
            435                 440                 445

Met Tyr Val Asn Ile Val Leu Val Val Cys Phe Leu Leu Val Phe
            450                 455                 460

Arg Leu Pro Lys Asn Ile
465                 470

<210> SEQ ID NO 9
<211> LENGTH: 1401
<212> TYPE: DNA
<213> ORGANISM: Listeria monocytogenes

<400> SEQUENCE: 9
atgacttcaa cagcgtataa aggtacaaat aaactaatcg ttgggattgt tttcggggtt      60
atcacgtttt ggcttttttgc tcaatctatg gtgaatattg ttccggccgt gcaatctgac    120
cttggaattt cctcagattt acttagtatt gccatcagtt taaccgcgct attctcaggt    180 attttttatcg ttgtagcagg tgggatggct gacaaatttg gtcgcgtgaa attaacttat    240
atcggactta ttcttagtat catcggttca ctgctacttg ttgtcactca agggtcgacg    300
ttacttatta tcggccgtat tattcaaggt ctttcagctg cttgtattat gccagcaacc    360
cttgccttaa tgaaaactta ttttgacggg gcagatagac aaagagcact tagttactgg    420
tcaattggct catggggtgg atcaggtatt tgttcgttcg caggtggcgc tatcgcaaca    480
tatatgggct ggcgctggat tttcattatt ccatcgtat tcgcactgct tggaatgcta    540
cttattaaag gtactccaga agtaaagtc gttcaaaata caaaagcaaa atttgattca    600
tttggtcttg ttcttttttgt tatcgcaatg gtttgtttga accttattat tactcgtggc    660
gcaacatttg gctggacaag cccaattact attacaatgc tcgttgtttt cctagttttct    720 gcgggattat tttccgagt ggaactgcga caagcaaacg gatttattga tttctcgttg    780
tttaaaaata aagcttatac aggcgcaaca ctttcgaact tcttgctaaa cgcagcagct    840
```

-continued

```
ggaacactgg ttgtcgcaaa cacttatgtg caaattggtc gcggttttac ggcgttccaa    900
tccggtttac tttctatcgg atatcttgtc tgtgtgctcg gaatgattcg catcggtgaa    960
aaaattcttc aacgtgttgg tgcgcgtaaa ccaatgattt taggctctgg tattacggct   1020
gttggtattg cactaatggc gctgacgttt attccgggaa ccctttatac agtgcttgta   1080
tttatcggtt ttgctttatt cgggattgga cttggcatgt atgcgactcc ttcaacagat   1140
acagccattt ctaatgctcc agaagataaa gtcggagtag catctggtat ttacaaaatg   1200
gcaagttcgc taggtggctc attcggcgtg gcgatatctg ctacgattta tggtgtgatt   1260
gcactttcag gaaatattga tttagccgca atggtggggc ttttaacgaa cgtcggtttt   1320
tgtgtcgttt cacttatttc cgttgctata acaacaccat ctgcgaaaaa agcgctcgaa   1380
ttaaaagccg caaagaata g                                              1401
```

<210> SEQ ID NO 10
<211> LENGTH: 466
<212> TYPE: PRT
<213> ORGANISM: Listeria monocytogenes

<400> SEQUENCE: 10

```
Met Thr Ser Thr Ala Tyr Lys Gly Thr Asn Lys Leu Ile Val Gly Ile
  1               5                  10                  15

Val Phe Gly Val Ile Thr Phe Trp Leu Phe Ala Gln Ser Met Val Asn
             20                  25                  30

Ile Val Pro Ala Val Gln Ser Asp Leu Gly Ile Ser Ser Asp Leu Leu
         35                  40                  45

Ser Ile Ala Ile Ser Leu Thr Ala Leu Phe Ser Gly Ile Phe Ile Val
     50                  55                  60

Val Ala Gly Gly Met Ala Asp Lys Phe Gly Arg Val Lys Leu Thr Tyr
 65                  70                  75                  80

Ile Gly Leu Ile Leu Ser Ile Ile Gly Ser Leu Leu Leu Val Val Thr
                 85                  90                  95

Gln Gly Ser Thr Leu Leu Ile Ile Gly Arg Ile Ile Gln Gly Leu Ser
            100                 105                 110

Ala Ala Cys Ile Met Pro Ala Thr Leu Ala Leu Met Lys Thr Tyr Phe
        115                 120                 125

Asp Gly Ala Asp Arg Gln Arg Ala Leu Ser Tyr Trp Ser Ile Gly Ser
    130                 135                 140

Trp Gly Gly Ser Gly Ile Cys Ser Phe Ala Gly Ala Ile Ala Thr
145                 150                 155                 160

Tyr Met Gly Trp Arg Trp Ile Phe Ile Ile Ser Ile Val Phe Ala Leu
                165                 170                 175

Leu Gly Met Leu Leu Ile Lys Gly Thr Pro Glu Ser Lys Val Val Gln
            180                 185                 190

Asn Thr Lys Ala Lys Phe Asp Ser Phe Gly Leu Val Leu Phe Val Ile
        195                 200                 205

Ala Met Val Cys Leu Asn Leu Ile Ile Thr Arg Gly Ala Thr Phe Gly
    210                 215                 220

Trp Thr Ser Pro Ile Thr Ile Thr Met Leu Val Val Phe Leu Val Ser
225                 230                 235                 240

Ala Gly Leu Phe Phe Arg Val Glu Leu Arg Gln Ala Asn Gly Phe Ile
                245                 250                 255

Asp Phe Ser Leu Phe Lys Asn Lys Ala Tyr Thr Gly Ala Thr Leu Ser
            260                 265                 270
```

```
Asn Phe Leu Leu Asn Ala Ala Ala Gly Thr Leu Val Ala Asn Thr
            275                 280                 285

Tyr Val Gln Ile Gly Arg Gly Phe Thr Ala Phe Gln Ser Gly Leu Leu
        290                 295                 300

Ser Ile Gly Tyr Leu Val Cys Val Leu Gly Met Ile Arg Ile Gly Glu
305                 310                 315                 320

Lys Ile Leu Gln Arg Val Gly Ala Arg Lys Pro Met Ile Leu Gly Ser
                325                 330                 335

Gly Ile Thr Ala Val Gly Ile Ala Leu Met Ala Leu Thr Phe Ile Pro
                340                 345                 350

Gly Thr Leu Tyr Thr Val Leu Val Phe Ile Gly Phe Ala Leu Phe Gly
            355                 360                 365

Ile Gly Leu Gly Met Tyr Ala Thr Pro Ser Thr Asp Thr Ala Ile Ser
370                 375                 380

Asn Ala Pro Glu Asp Lys Val Gly Val Ala Ser Gly Ile Tyr Lys Met
385                 390                 395                 400

Ala Ser Ser Leu Gly Gly Ser Phe Gly Val Ala Ile Ser Ala Thr Ile
                405                 410                 415

Tyr Gly Val Ile Ala Leu Ser Gly Asn Ile Asp Leu Ala Ala Met Val
            420                 425                 430

Gly Leu Leu Thr Asn Val Gly Phe Cys Val Val Ser Leu Ile Ser Val
            435                 440                 445

Ala Ile Thr Thr Pro Ser Ala Lys Lys Ala Leu Glu Leu Lys Ala Ala
            450                 455                 460

Lys Glu
465

<210> SEQ ID NO 11
<211> LENGTH: 1167
<212> TYPE: DNA
<213> ORGANISM: Listeria monocytogenes

<400> SEQUENCE: 11
gtggatatga aaaagtgaa tcctaatttg acacttttag cgctagcaat tagtgcgttt        60
gggattggtt caacagaatt tattagtgtg gggctacttc cactgatttc ttctagtatg      120
ggtgtgtcga ttagcacggc tggtttgaca gtatcgattt atgcgcttgg tgtaatggtc      180
ggagcgccgg ttttaacaac cgtgacggcg aagatgaatc gtaaaaatct gttattatta      240
gtaatgctcg tgtttctaat aggtaatctt gtctctgcat ttgctgtaag ttttggaatg      300
ctccttactg ggcgcgtagt tgcggccttt gcgcacgggg tgtttatgtc gattgcttct      360
gttatcgcag ccgatgtggt tcatccgagt aaacgggcta gtgcaattgc ggtgatgttt      420
acagggctga ctgtggcgac tgtgacaggg gtaccacttg gacgtttat cggtcaacta       480 tttggctggc ggatgtcatt cctgtttatt gttgcgattg gtgtgatagc aattattgct      540 aatttttcc ttgtgccgaa aaacttatct aatggaaaaa gtatttcgtt taaatcgatt       600
gggcaattgt tagttaataa aaaaatcgcg aaggtgttac tcatgacggc gtttggttat      660
ggtggtactt ttgtggttta tacgtattta tcgccgatgt ttagcggaat gggctattcg      720
acaagtatga tagttatttt actgattgct tatggtgtga tggttgcgat tgggaatacg      780
attggtgggc attttgcgaa tgagcgtcct gccaaagcac ttttcattat gtttagctta      840
caaggtgtga cgttgttgtt gcttcaattc acttcaggaa atgccatttt aggtttaatg      900
actattatgc taatgggatt tttcgcgttt atgaatgtgt ctggtttgca actttatgtg      960
```

```
gtgcaattag cagaacggta tttgccagaa acgttagca tggcttctgc gcttaatatt    1020
tctgcgttta atattggaat cgcactcgga gcatttatcg gtggattagt aacagaatat    1080
attggtttaa gttatacacc aattgttgga tttttgatgg ttttcatcgc aattatttta    1140
actttctata tgaaaaaaga taaatag                                       1167
```

<210> SEQ ID NO 12
<211> LENGTH: 388
<212> TYPE: PRT
<213> ORGANISM: Listeria monocytogenes

<400> SEQUENCE: 12

```
Met Asp Met Lys Lys Val Asn Pro Asn Leu Thr Leu Leu Ala Leu Ala
1               5                   10                  15

Ile Ser Ala Phe Gly Ile Gly Ser Thr Glu Phe Ile Ser Val Gly Leu
            20                  25                  30

Leu Pro Leu Ile Ser Ser Met Gly Val Ser Ile Ser Thr Ala Gly
        35                  40                  45

Leu Thr Val Ser Ile Tyr Ala Leu Gly Val Met Val Gly Ala Pro Val
    50                  55                  60

Leu Thr Thr Val Thr Ala Lys Met Asn Arg Lys Asn Leu Leu Leu Leu
65                  70                  75                  80

Val Met Leu Val Phe Leu Ile Gly Asn Leu Val Ser Ala Phe Ala Val
                85                  90                  95

Ser Phe Gly Met Leu Leu Thr Gly Arg Val Val Ala Ala Phe Ala His
            100                 105                 110

Gly Val Phe Met Ser Ile Ala Ser Val Ile Ala Ala Asp Val Val His
        115                 120                 125

Pro Ser Lys Arg Ala Ser Ala Ile Ala Val Met Phe Thr Gly Leu Thr
130                 135                 140

Val Ala Thr Val Thr Gly Val Pro Leu Gly Thr Phe Ile Gly Gln Leu
145                 150                 155                 160

Phe Gly Trp Arg Met Ser Phe Leu Phe Ile Val Ala Ile Gly Val Ile
                165                 170                 175

Ala Ile Ile Ala Asn Phe Phe Leu Val Pro Lys Asn Leu Ser Asn Gly
            180                 185                 190

Lys Ser Ile Ser Phe Lys Ser Ile Gly Gln Leu Leu Val Asn Lys Lys
        195                 200                 205

Ile Ala Lys Val Leu Leu Met Thr Ala Phe Gly Tyr Gly Gly Thr Phe
    210                 215                 220

Val Val Tyr Thr Tyr Leu Ser Pro Met Phe Ser Gly Met Gly Tyr Ser
225                 230                 235                 240

Thr Ser Met Ile Val Ile Leu Leu Ile Ala Tyr Gly Val Met Val Ala
                245                 250                 255

Ile Gly Asn Thr Ile Gly Gly His Phe Ala Asn Glu Arg Pro Ala Lys
            260                 265                 270

Ala Leu Phe Ile Met Phe Ser Leu Gln Gly Val Thr Leu Leu Leu Leu
        275                 280                 285

Gln Phe Thr Ser Gly Asn Ala Ile Leu Gly Leu Met Thr Ile Met Leu
    290                 295                 300

Met Gly Phe Phe Ala Phe Met Asn Val Ser Gly Leu Gln Leu Tyr Val
305                 310                 315                 320

Val Gln Leu Ala Glu Arg Tyr Leu Pro Glu Thr Val Ser Met Ala Ser
                325                 330                 335
```

Ala Leu Asn Ile Ser Ala Phe Asn Ile Gly Ile Ala Leu Gly Ala Phe
                340                 345                 350

Ile Gly Gly Leu Val Thr Glu Tyr Ile Gly Leu Ser Tyr Thr Pro Ile
        355                 360                 365

Val Gly Phe Leu Met Val Phe Ile Ala Ile Ile Leu Thr Phe Tyr Met
    370                 375                 380

Lys Lys Asp Lys
385

<210> SEQ ID NO 13
<211> LENGTH: 1149
<212> TYPE: DNA
<213> ORGANISM: Listeria monocytogenes

<400> SEQUENCE: 13
ttggaaaata agacaagact ttggacgaag gactacgtat ttttattgtt aggcagtgta      60
cttttatata ttggatttat ggtgtttatg cctacgttgc cggcacgcat tattgagcta     120
ggtggaacgc aaatggaagc tagtttggct gttgggctat tctccatcgt agcgctatta     180
atgcgggcga ttgctgggag ttggaatgac aaattcggac cgaaagtact tattatcgtg     240 ggtttttga ttttaatttt aactacagtg aacttttatt ggtcaactgc ggtggcggcc     300
ttacttatat tacggctttt ccacggggct ggctggggta tcggaacaac ttccattgca     360
acaggcgttt ctaaacttgt gccgccaagc agaacgggag aaggtattgg ttttatggg     420 cttacgactg cactcggaat gtcacttgcg ccgattatcg ctattttaat tatgaattat     480
ttttctttcg atgttttagt gacgttttca cttgttttga tggtgtttat tttaattttg     540
atgacacagg tgaaaattcc aaaatcagaa aaattgtac atcaaaaaat gaaattgttt     600
gagaaaacgg ccttgcttcc ggctggattg tgtttattaa tggctattcc gcttggtggg     660
atccagacgt ttatgatggt atatggaaca gaactgggga tttcgacaac gtggatatat     720
tttatcgggc aagcgattat ggttcttgtg agccgtttgt ttgctgggcg gctttatgat     780
acaaagggac accgttttgt tattattcca ggagcgcttt cgatgataat tgggatatta     840
attctttctt ttgcaactgg ggcaatcagt ttgtttatcg catcgctatt ctttgggcta     900
ggttacggga tgtcgcaacc ggcgcttcaa gcactggctg ttgaccgggc tgcaccgcac     960
aataaaggta ccgcgaacgg gacttttctt tcgggaatgg acattggaat ggctgttggt    1020
agttttggtc tgagtatcgt ggcgacttac tataattatg cgatcatgta ccgcacagca    1080
attattgcgc tcatcgtatt ttttgccgtg tattggttta ctttaggacg aaaagtgaaa    1140
aatagctaa                                                            1149

<210> SEQ ID NO 14
<211> LENGTH: 382
<212> TYPE: PRT
<213> ORGANISM: Listeria monocytogenes

<400> SEQUENCE: 14

Met Glu Asn Lys Thr Arg Leu Trp Thr Lys Asp Tyr Val Phe Leu Leu
1               5                   10                  15

Leu Gly Ser Val Leu Leu Tyr Ile Gly Phe Met Val Phe Met Pro Thr
            20                  25                  30

Leu Pro Ala Arg Ile Ile Glu Leu Gly Gly Thr Gln Met Glu Ala Ser
        35                  40                  45

Leu Ala Val Gly Leu Phe Ser Ile Val Ala Leu Leu Met Arg Ala Ile
    50                  55                  60

```
Ala Gly Ser Trp Asn Asp Lys Phe Gly Pro Lys Val Leu Ile Ile Val
 65                  70                  75                  80

Gly Phe Leu Ile Leu Ile Leu Thr Thr Val Asn Phe Tyr Trp Ser Thr
                 85                  90                  95

Ala Val Ala Ala Leu Leu Ile Leu Arg Leu Phe His Gly Ala Gly Trp
            100                 105                 110

Gly Ile Gly Thr Thr Ser Ile Ala Thr Gly Val Ser Lys Leu Val Pro
        115                 120                 125

Pro Ser Arg Thr Gly Glu Gly Ile Gly Phe Tyr Gly Leu Thr Thr Ala
    130                 135                 140

Leu Gly Met Ser Leu Ala Pro Ile Ile Ala Ile Leu Ile Met Asn Tyr
145                 150                 155                 160

Phe Ser Phe Asp Val Leu Val Thr Phe Ser Leu Val Leu Met Val Phe
                165                 170                 175

Ile Leu Ile Leu Met Thr Gln Val Lys Ile Pro Lys Ser Glu Lys Ile
            180                 185                 190

Val His Gln Lys Met Lys Leu Phe Glu Lys Thr Ala Leu Leu Pro Ala
        195                 200                 205

Gly Leu Cys Leu Leu Met Ala Ile Pro Leu Gly Gly Ile Gln Thr Phe
    210                 215                 220

Met Met Val Tyr Gly Thr Glu Leu Gly Ile Ser Thr Thr Trp Ile Tyr
225                 230                 235                 240

Phe Ile Gly Gln Ala Ile Met Val Leu Val Ser Arg Leu Phe Ala Gly
                245                 250                 255

Arg Leu Tyr Asp Thr Lys Gly His Arg Phe Val Ile Ile Pro Gly Ala
            260                 265                 270

Leu Ser Met Ile Ile Gly Ile Leu Ile Leu Ser Phe Ala Thr Gly Ala
        275                 280                 285

Ile Ser Leu Phe Ile Ala Ser Leu Phe Phe Gly Leu Gly Tyr Gly Met
    290                 295                 300

Ser Gln Pro Ala Leu Gln Ala Leu Ala Val Asp Arg Ala Ala Pro His
305                 310                 315                 320

Asn Lys Gly Thr Ala Asn Gly Thr Phe Leu Ser Gly Met Asp Ile Gly
                325                 330                 335

Met Ala Val Gly Ser Phe Gly Leu Ser Ile Val Ala Thr Tyr Tyr Asn
            340                 345                 350

Tyr Ala Ile Met Tyr Arg Thr Ala Ile Ile Ala Leu Ile Val Phe Phe
        355                 360                 365

Ala Val Tyr Trp Phe Thr Leu Gly Arg Lys Val Lys Asn Ser
    370                 375                 380

<210> SEQ ID NO 15
<211> LENGTH: 838
<212> TYPE: DNA
<213> ORGANISM: Homo Sapiens

<400> SEQUENCE: 15
gagtctaact gcaacctttc gaagcctttg ctctggcaca acaggtagta ggcgacactg      60
gtcgtgttgt tgacatgacc aacaagtgtc tcctccaaat tgctctcctg ttgtgcttct     120
ccacgacagc tctttccatg agctacaact tgcttggatt cctacaaaga agcagcaatt     180
gtcagtgtca gaagctcctg tggcaattga atgggaggct tgaatactgc ctcaaggaca     240
ggaggaactt tgacatccct gaggagatta agcagctgca gcagttccag aaggaggacg     300
```

```
ccgcagtgac catctatgag atgctccaga acatctttgc tattttcaga caagattcat    360
cgagcactgg ctggaatgag actattgttg agaacctcct ggctaatgtc tatcatcaga    420
gaaaccatct gaagacagtc ctggaagaaa aactggagaa agaagatttc accagggga     480 aacgcatgag cagtctgcac ctgaaaagat attatgggag gattctgcat acctgaagg     540 ccaaggagga cagtcactgt gcctggacca tagtcagagt ggaaatccta aggaactttt    600
acgtcattaa cagacttaca ggttacctcc gaaactgaag atctcctagc ctgtgcctct    660
gggacgggac aattgcttca gcattcttc aaccagcaga tgctgtttaa gtgactgatg     720
gcgaatgtac tgcatatgaa aggacactag aagattttga aattttttatt aaattatgag   780 gtattttat ttattttaaat tttatttggg aaaataaatt attttggtg caaaagtc       838
```

<210> SEQ ID NO 16
<211> LENGTH: 187
<212> TYPE: PRT
<213> ORGANISM: Homo Sapiens

<400> SEQUENCE: 16

```
Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
                20                  25                  30

Ser Ser Asn Cys Gln Cys Gln Lys Leu Leu Trp Gln Leu Asn Gly Arg
            35                  40                  45

Leu Glu Tyr Cys Leu Lys Asp Arg Arg Asn Phe Asp Ile Pro Glu Glu
        50                  55                  60

Ile Lys Gln Leu Gln Gln Phe Gln Lys Glu Asp Ala Ala Val Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Arg Asn His Leu Lys Thr Val Leu Glu Glu Lys Leu Glu
        115                 120                 125

Lys Glu Asp Phe Thr Arg Gly Lys Arg Met Ser Ser Leu His Leu Lys
    130                 135                 140

Arg Tyr Tyr Gly Arg Ile Leu His Tyr Leu Lys Ala Lys Glu Asp Ser
145                 150                 155                 160

His Cys Ala Trp Thr Ile Val Arg Val Glu Ile Leu Arg Asn Phe Tyr
                165                 170                 175

Val Ile Asn Arg Leu Thr Gly Tyr Leu Arg Asn
            180                 185
```

<210> SEQ ID NO 17
<211> LENGTH: 770
<212> TYPE: DNA
<213> ORGANISM: Mus musculus

<400> SEQUENCE: 17

```
acaccagcct ggcttccatc atgaacaaca ggtggatcct ccacgctgcg ttcctgctgt     60
gcttctccac cacagccctc tccatcaact ataagcagct ccagctccaa gaaaggacga    120
acattcggaa atgtcaggag ctcctggagc agctgaatgg aaagatcaac ctcacctaca    180
gggcggactt caagatccct atggagatga cggagaagat gcagaagagt acactgcct    240 ttgccatcca agagatgctc cagaatgtct tcttgtctt cagaaacaat ttctccagca    300
```

```
ctgggtggaa tgagactatt gttgtacgtc tcctggatga actccaccag cagacagtgt    360
ttctgaagac agtactagag gaaaagcaag aggaaagatt gacgtgggag atgtcctcaa    420
ctgctctcca cttgaagagc tattactgga gggtgcaaag gtaccttaaa ctcatgaagt    480
acaacagcta cgcctggatg gtggtccgag cagagatctt caggaacttt ctcatcattc    540
gaagacttac cagaaacttc caaaactgaa gacctgtcag ttgatgcctc agaatgagtg    600
gtggttgcag gcaacccttta agcatcgag gcggactctg ggactggtag tgaatctact    660
gcatttgaaa ggtcaaagga aaacagagtt tttattaatt tataatttaa attattttct    720 acttttatt taaactttt aacctcagaa aataaaatat ttataataca                  770
```

```
<210> SEQ ID NO 18
<211> LENGTH: 182
<212> TYPE: PRT
<213> ORGANISM: Mus musculus

<400> SEQUENCE: 18

Met Asn Asn Arg Trp Ile Leu His Ala Ala Phe Leu Leu Cys Phe Ser
1               5                   10                  15

Thr Thr Ala Leu Ser Ile Asn Tyr Lys Gln Leu Gln Leu Gln Glu Arg
            20                  25                  30

Thr Asn Ile Arg Lys Cys Gln Glu Leu Leu Glu Gln Leu Asn Gly Lys
        35                  40                  45

Ile Asn Leu Thr Tyr Arg Ala Asp Phe Lys Ile Pro Met Glu Met Thr
    50                  55                  60

Glu Lys Met Gln Lys Ser Tyr Thr Ala Phe Ala Ile Gln Glu Met Leu
65                  70                  75                  80

Gln Asn Val Phe Leu Val Phe Arg Asn Asn Phe Ser Ser Thr Gly Trp
                85                  90                  95

Asn Glu Thr Ile Val Val Arg Leu Leu Asp Glu Leu His Gln Gln Thr
            100                 105                 110

Val Phe Leu Lys Thr Val Leu Glu Glu Lys Gln Glu Glu Arg Leu Thr
        115                 120                 125

Trp Glu Met Ser Ser Thr Ala Leu His Leu Lys Ser Tyr Tyr Trp Arg
    130                 135                 140

Val Gln Arg Tyr Leu Lys Leu Met Lys Tyr Asn Ser Tyr Ala Trp Met
145                 150                 155                 160

Val Val Arg Ala Glu Ile Phe Arg Asn Phe Leu Ile Ile Arg Arg Leu
                165                 170                 175

Thr Arg Asn Phe Gln Asn
            180
```

```
<210> SEQ ID NO 19
<211> LENGTH: 26
<212> TYPE: DNA
<213> ORGANISM: Artificial Sequence
<220> FEATURE:
<223> OTHER INFORMATION: Single strand DNA oligonucleotide

<400> SEQUENCE: 19
tgaatgtgtc tggtttgcaa ctttat                                          26
```

```
<210> SEQ ID NO 20
<211> LENGTH: 21
<212> TYPE: DNA
<213> ORGANISM: Artificial Sequence
<220> FEATURE:
```

```
<223> OTHER INFORMATION: Single strand DNA oligonucleotide

<400> SEQUENCE: 20
aagccatgct aaccgtttct g                                            21

<210> SEQ ID NO 21
<211> LENGTH: 19
<212> TYPE: DNA
<213> ORGANISM: Artificial Sequence
<220> FEATURE:
<223> OTHER INFORMATION: Single strand DNA oligonucleotide

<400> SEQUENCE: 21
ggccgtgcaa tctgacctt                                               19

<210> SEQ ID NO 22
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 22
cctgagaata gcgcggttaa a                                            21

<210> SEQ ID NO 23
<211> LENGTH: 19
<212> TYPE: DNA
<213> ORGANISM: Artificial Sequence
<220> FEATURE:
<223> OTHER INFORMATION: Single strand DNA oligonucleotide

<400> SEQUENCE: 23
cgcaaatcaa cgccacaat                                               19

<210> SEQ ID NO 24
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 24
cagagccaag aattccgaag a                                            21

<210> SEQ ID NO 25
<211> LENGTH: 25
<212> TYPE: DNA
<213> ORGANISM: Artificial Sequence
<220> FEATURE:
<223> OTHER INFORMATION: Single strand DNA oligonucleotide

<400> SEQUENCE: 25
cagcaagtac atcagtgaag cgtaa                                        25

<210> SEQ ID NO 26
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 26
ggtagcgcga cattcatcaa                                              20
```

```
<210> SEQ ID NO 27
<211> LENGTH: 19
<212> TYPE: DNA
<213> ORGANISM: Artificial Sequence
<220> FEATURE:
<223> OTHER INFORMATION: Single strand DNA oligonucleotide

<400> SEQUENCE: 27
ccgtgcggtt cttcggtat                                                  19

<210> SEQ ID NO 28
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 28
tttactgccg aaccgtggtt                                                 20

<210> SEQ ID NO 29
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 29
gcaacaggtg ggcagaaaat                                                 20

<210> SEQ ID NO 30
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 30
gcgccatgtt aagagcagtt t                                               21

<210> SEQ ID NO 31
<211> LENGTH: 27
<212> TYPE: DNA
<213> ORGANISM: Artificial Sequence
<220> FEATURE:
<223> OTHER INFORMATION: Single strand DNA oligonucleotide

<400> SEQUENCE: 31
taaaaacaat gtattagtat accacgg                                         27

<210> SEQ ID NO 32
<211> LENGTH: 22
<212> TYPE: DNA
<213> ORGANISM: Artificial Sequence
<220> FEATURE:
<223> OTHER INFORMATION: Single strand DNA oligonucleotide

<400> SEQUENCE: 32
gattcacaac ttgaatgtct gc                                              22

<210> SEQ ID NO 33
<211> LENGTH: 22
<212> TYPE: DNA
<213> ORGANISM: Artificial Sequence
<220> FEATURE:
<223> OTHER INFORMATION: Single strand DNA oligonucleotide
```

```
<400> SEQUENCE: 33
gcggatgaag aggataatta cg                                        22

<210> SEQ ID NO 34
<211> LENGTH: 24
<212> TYPE: DNA
<213> ORGANISM: Artificial Sequence
<220> FEATURE:
<223> OTHER INFORMATION: Single strand DNA oligonucleotide

<400> SEQUENCE: 34
tagtcaatac gttcttttc tacc                                       24

<210> SEQ ID NO 35
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 35
gtggaacgca aatggaagct                                           20

<210> SEQ ID NO 36
<211> LENGTH: 19
<212> TYPE: DNA
<213> ORGANISM: Artificial Sequence
<220> FEATURE:
<223> OTHER INFORMATION: Single strand DNA oligonucleotide

<400> SEQUENCE: 36
ttccaactcc cagcaatcg                                            19

<210> SEQ ID NO 37
<211> LENGTH: 18
<212> TYPE: DNA
<213> ORGANISM: Artificial Sequence
<220> FEATURE:
<223> OTHER INFORMATION: Single strand DNA oligonucleotide

<400> SEQUENCE: 37
cctggtagtc cacgccgt                                             18

<210> SEQ ID NO 38
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 38
tgcgttagct gcagcactaa g                                         21

<210> SEQ ID NO 39
<211> LENGTH: 23
<212> TYPE: DNA
<213> ORGANISM: Artificial Sequence
<220> FEATURE:
<223> OTHER INFORMATION: Single strand DNA oligonucleotide

<400> SEQUENCE: 39
cgtgaacagc atcatttaat cga                                       23

<210> SEQ ID NO 40
<211> LENGTH: 21
```

```
<212> TYPE: DNA
<213> ORGANISM: Artificial Sequence
<220> FEATURE:
<223> OTHER INFORMATION: Single strand DNA oligonucleotide

<400> SEQUENCE: 40
gtatcgcgtg ccactgaaat c                                              21

<210> SEQ ID NO 41
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 41
ccaactgggc tagggaacat c                                              21

<210> SEQ ID NO 42
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 42
cctccgtcaa aaaggccata                                                20

<210> SEQ ID NO 43

<400> SEQUENCE: 43

000

<210> SEQ ID NO 44
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 44
ccaagaaagg acgaacattc g                                              21

<210> SEQ ID NO 45
<211> LENGTH: 19
<212> TYPE: DNA
<213> ORGANISM: Artificial Sequence
<220> FEATURE:
<223> OTHER INFORMATION: Single strand DNA oligonucleotide

<400> SEQUENCE: 45
ccgccctgta ggtgaggtt                                                 19

<210> SEQ ID NO 46
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 46
ttgtggaagg gctcatgacc                                                20

<210> SEQ ID NO 47
<211> LENGTH: 20
```

<210> SEQ ID NO 48
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 47
tcttctgggt ggcagtgatg                                          20

<210> SEQ ID NO 48
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 48
aggagagccg ggtgacagta                                          20

<210> SEQ ID NO 49
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 49
tcagaatctt cccgttgctt g                                        21

<210> SEQ ID NO 50
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 50
ttccatccag ttgccttctt g                                        21

<210> SEQ ID NO 51
<211> LENGTH: 19
<212> TYPE: DNA
<213> ORGANISM: Artificial Sequence
<220> FEATURE:
<223> OTHER INFORMATION: Single strand DNA oligonucleotide

<400> SEQUENCE: 51
gaaggccgtg gttgtcacc                                           19

<210> SEQ ID NO 52
<211> LENGTH: 33
<212> TYPE: DNA
<213> ORGANISM: Artificial Sequence
<220> FEATURE:
<223> OTHER INFORMATION: Single strand DNA oligonucleotide

<400> SEQUENCE: 52
actatgtcga cgcagtaatc acgttcttgc gca                           33

<210> SEQ ID NO 53
<211> LENGTH: 50
<212> TYPE: DNA
<213> ORGANISM: Artificial Sequence
<220> FEATURE:
<223> OTHER INFORMATION: Single strand DNA oligonucleotide

<400> SEQUENCE: 53
tcggtaaccg aatacaagt aggtattacg tttattcgtc tgttccatga                50

<210> SEQ ID NO 54
<211> LENGTH: 50
<212> TYPE: DNA
<213> ORGANISM: Artificial Sequence
<220> FEATURE:
<223> OTHER INFORMATION: Single strand DNA oligonucleotide

<400> SEQUENCE: 54
tcatggaaca gacgaataaa cgtaatacct acttgtattc cggttaccga                50

<210> SEQ ID NO 55
<211> LENGTH: 33
<212> TYPE: DNA
<213> ORGANISM: Artificial Sequence
<220> FEATURE:
<223> OTHER INFORMATION: Single strand DNA oligonucleotide

<400> SEQUENCE: 55
attacctgca gagcttgctg gcaagtattt ctt                                  33

<210> SEQ ID NO 56
<211> LENGTH: 37
<212> TYPE: DNA
<213> ORGANISM: Artificial Sequence
<220> FEATURE:
<223> OTHER INFORMATION: Single strand DNA oligonucleotide

<400> SEQUENCE: 56
atactggtac cctttgtaat tatctggaat ctccatc                              37

<210> SEQ ID NO 57
<211> LENGTH: 47
<212> TYPE: DNA
<213> ORGANISM: Artificial Sequence
<220> FEATURE:
<223> OTHER INFORMATION: Single strand DNA oligonucleotide

<400> SEQUENCE: 57
gacaagactt tggacgaagg acaatagcta acatctcttg tgaagtg                   47

<210> SEQ ID NO 58
<211> LENGTH: 47
<212> TYPE: DNA
<213> ORGANISM: Artificial Sequence
<220> FEATURE:
<223> OTHER INFORMATION: Single strand DNA oligonucleotide

<400> SEQUENCE: 58
cacttcacaa gagatgttag ctattgtcct tcgtccaaag tcttgtc                   47

<210> SEQ ID NO 59
<211> LENGTH: 32
<212> TYPE: DNA
<213> ORGANISM: Artificial Sequence
<220> FEATURE:
<223> OTHER INFORMATION: Single strand DNA oligonucleotide

<400> SEQUENCE: 59
ataacctgca gtaacgagtc cgccagaagt gg                                   32

<210> SEQ ID NO 60
<211> LENGTH: 33
<212> TYPE: DNA
<213> ORGANISM: Artificial Sequence
<220> FEATURE:
<223> OTHER INFORMATION: Single strand DNA oligonucleotide

<400> SEQUENCE: 60
attatgtcga ctcagaaatg cccgttaggt act                                33

<210> SEQ ID NO 61
<211> LENGTH: 48
<212> TYPE: DNA
<213> ORGANISM: Artificial Sequence
<220> FEATURE:
<223> OTHER INFORMATION: Single strand DNA oligonucleotide

<400> SEQUENCE: 61
agaataacta atgacttcaa cagcgtagcg ctcgaattaa aagccgca                48

<210> SEQ ID NO 62
<211> LENGTH: 48
<212> TYPE: DNA
<213> ORGANISM: Artificial Sequence
<220> FEATURE:
<223> OTHER INFORMATION: Single strand DNA oligonucleotide

<400> SEQUENCE: 62
tgcggctttt aattcgagcg ctacgctgtt gaagtcatta gttattct                48

<210> SEQ ID NO 63
<211> LENGTH: 35
<212> TYPE: DNA
<213> ORGANISM: Artificial Sequence
<220> FEATURE:
<223> OTHER INFORMATION: Single strand DNA oligonucleotide

<400> SEQUENCE: 63
attatgtcga ctctcattta tgcgctagat tatcc                              35

<210> SEQ ID NO 64
<211> LENGTH: 53
<212> TYPE: DNA
<213> ORGANISM: Artificial Sequence
<220> FEATURE:
<223> OTHER INFORMATION: Single strand DNA oligonucleotide

<400> SEQUENCE: 64
aaggcctatt atttgaacta tttatctttt catatccaca ttgtttcccc cta          53

<210> SEQ ID NO 65
<211> LENGTH: 53
<212> TYPE: DNA
<213> ORGANISM: Artificial Sequence
<220> FEATURE:
<223> OTHER INFORMATION: Single strand DNA oligonucleotide

<400> SEQUENCE: 65
tagggggaaa caatgtggat atgaaaagat aaatagttca ataataggc ctt           53

<210> SEQ ID NO 66
<211> LENGTH: 32
<212> TYPE: DNA
<213> ORGANISM: Artificial Sequence
<220> FEATURE:
<223> OTHER INFORMATION: Single strand DNA oligonucleotide

<400> SEQUENCE: 66
attatctgca gtttctagcg ccttatcgag ct                                 32

```
<210> SEQ ID NO 67
<211> LENGTH: 35
<212> TYPE: DNA
<213> ORGANISM: Artificial Sequence
<220> FEATURE:
<223> OTHER INFORMATION: Single strand DNA oligonucleotide

<400> SEQUENCE: 67
attatgtcga ccacggtcag ttgtgtttag cattg                              35

<210> SEQ ID NO 68
<211> LENGTH: 44
<212> TYPE: DNA
<213> ORGANISM: Artificial Sequence
<220> FEATURE:
<223> OTHER INFORMATION: Single strand DNA oligonucleotide

<400> SEQUENCE: 68
tcgctttatt atttagcttt acgacctgtt gcttcttgtt gcat                    44

<210> SEQ ID NO 69
<211> LENGTH: 18
<212> TYPE: DNA
<213> ORGANISM: Artificial Sequence
<220> FEATURE:
<223> OTHER INFORMATION: Single strand DNA oligonucleotide

<400> SEQUENCE: 69
atgcaacaag aagcaaca                                                 18
```